United States Patent [19]

Kamiya et al.

[11] 4,113,940
[45] Sep. 12, 1978

[54] 7-AMINO 2-LOWER ALKYL-2 OR 3-CEPHEM-4-CARBOXYLIC ACID DERIVATIVES AND PROCESSES FOR PREPARATION THEREOF

[75] Inventors: Takashi Kamiya, Suita; Tsutomu Teraji; Masashi Hashimoto, both of Toyonaka; Osamu Nakaguti, Osaka; Teruo Oku, Kyoto, all of Japan

[73] Assignee: Fujisawa Pharmaceutical Co., Ltd., Osaka, Japan

[21] Appl. No.: 640,910

[22] Filed: Dec. 15, 1975

Related U.S. Application Data

[63] Continuation-in-part of Ser. No. 451,159, Mar. 14, 1974, abandoned.

[30] Foreign Application Priority Data

| Mar. 15, 1973 | [JP] | Japan | 48-30718 |
| Mar. 15, 1973 | [JP] | Japan | 48-30719 |
| Mar. 15, 1973 | [JP] | Japan | 48-30720 |
| Aug. 2, 1973 | [JP] | Japan | 48-87852 |
| Aug. 2, 1973 | [JP] | Japan | 48-87853 |
| Oct. 3, 1975 | [GB] | United Kingdom | 40677/75 |

[51] Int. Cl.$^2$ ............ C07D 501/14; C07D 501/16; C07D 501/60; A61K 31/545
[52] U.S. Cl. ............ 544/16; 544/17; 544/18; 544/22; 544/23; 544/29; 424/246
[58] Field of Search ............ 260/243 C, 80-82; 544/16, 17, 23

[56] References Cited

U.S. PATENT DOCUMENTS

| 3,275,626 | 9/1966 | Morin et al. | 260/243 C |
| 3,660,396 | 5/1972 | Wright | 260/243 C |
| 3,719,672 | 3/1973 | Heusler et al. | 260/243 C |
| 3,780,028 | 12/1973 | Naito et al. | 260/243 C |
| 3,792,995 | 2/1974 | Ochiai et al. | 260/243 C X |
| 3,814,754 | 6/1974 | Jackson | 260/243 C |
| 3,926,972 | 12/1975 | Lowe | 260/243 C |

FOREIGN PATENT DOCUMENTS 2,461,933  7/1975  Fed. Rep. of Germany.

OTHER PUBLICATIONS

Scartazzini et al., Chemical Abstracts 76 140680r (1972).
Heusler et al., Chemical Abstracts 76 99, 686g (1972).
Heusler et al., Chemical Abstracts 77 114, 397e (1972).

*Primary Examiner*—Donald G. Daus
*Assistant Examiner*—Diana G. Rivers
*Attorney, Agent, or Firm*—Oblon, Fisher, Spivak, McClelland & Maier

[57] ABSTRACT

A compound of the formula

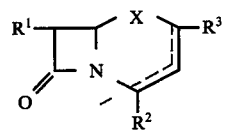

wherein $R^1$ is amino or substituted amino, $R^2$ is carboxy or protected carboxy, $R^3$ is lower alkyl and X is —S— or

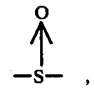

or a pharmaceutically acceptable salt thereof is effective against various microorganisms.

5 Claims, No Drawings

7-AMINO 2-LOWER ALKYL-2 OR 3-CHEPHEM-4-CARBOXYLIC ACID DERIVATIVES AND PROCESSES FOR PREPARATION THEREOF

CROSS-REFERENCE TO RELATED APPLICATIONS

This application is a continuation-in-part of application Ser. No. 451,159, filed Mar. 14, 1974, now abandoned.

BACKGROUND OF THE INVENTION

The present invention relates to 2-lower alkyl-2 or 3-cephem-4-carboxylic acid derivatives. More particularly, it relates to new 2-lower alkyl-2 or 3-cephem-4-carboxylic acid derivatives which have antimicrobial activities and to processes for the preparation thereof, to pharmaceutical composition comprising the same, and to a method of using the same therapeutically in the treatment of infections.

Accordingly, it is one object of this invention to provide the antimicrobially active 2-lower alkyl-2 or 3-cephem-4-carboxylic acid derivatives, which are active against a number of microorganisms.

Another object of the present invention is to provide processes for the preparation of 2-lower alkyl-2 or 3-cephem-4-carboxylic acid derivatives by synthesis.

A further object of the invention is to provide pharmaceutical compositions comprising, as effective antimicrobial agents, said 2-lower alkyl-2 or 3-cephem-4-carboxylic acid derivatives and the salt thereof.

Still a further object of the present invention is to provide a method of treating infectious disease caused by bacteria in humans and animals.

The 2-lower alkyl-2 or 3-cephem-4-carboxylic acid derivatives are novel compounds and comprise a new and unique nucleus in the chemical structure, which has been unexpected to those skilled in the art, and can be represented by the following formula (I)

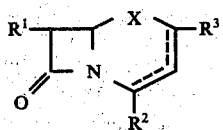

Wherein
$R^1$ is amino or a substituted amino,
$R^2$ is carboxy or a protected carboxy,
$R^3$ is lower alkyl and
X is —S— or

According to the present invention, the 2-lower alkyl-2 or 3-cephem-4-carboxylic acid derivatives can be prepared by various procedures, and the said processes are illustrated collectively for convenience sake by the following scheme, in which the process comprising step, (II) → (I) is a fundamental process and the others are alternative processes.

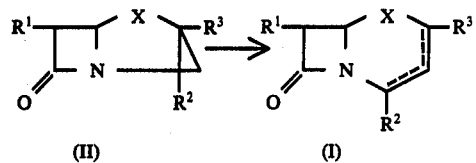

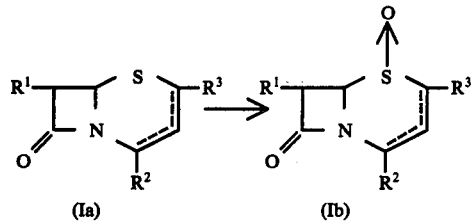

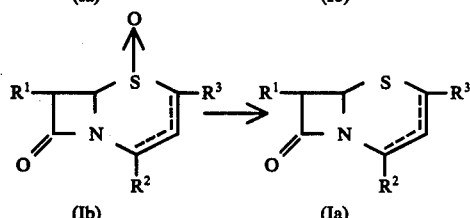

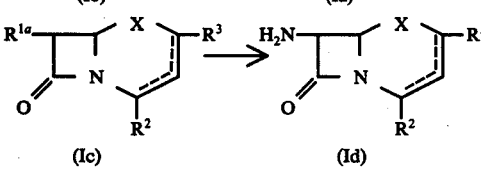

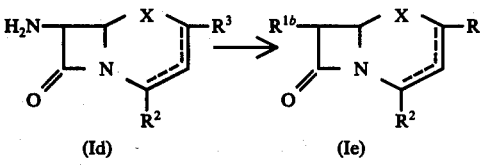

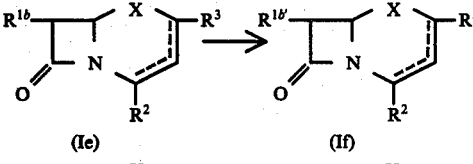

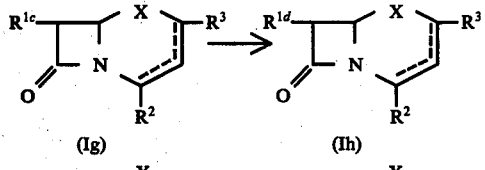

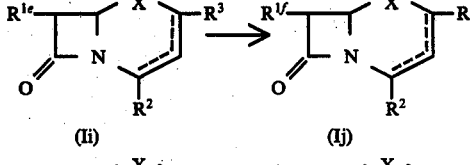

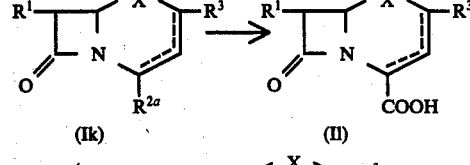

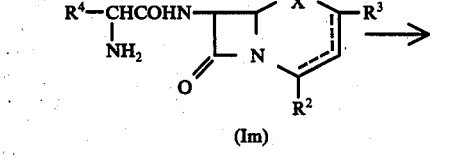

-continued

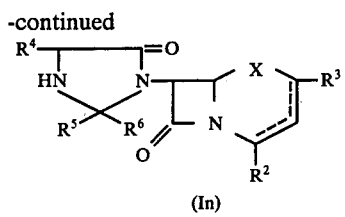

(In)

wherein
R¹ is amino or a substituted amino,
R² is carboxy or a protected carboxy,
R³ is lower alkyl,
R⁴ is aryl,
R⁵ and R⁶ are each lower alkyl,
X is —S— or

R$^{1a}$ is a protected amino,
R$^{1b}$ and R$^{1b'}$ are each acylamino,
R$^{1c}$ is acylamino having a protected amino,
R$^{1d}$ is acylamino having an amino,
R$^{1e}$ is acylamino having a protected hydroxy,
R$^{1f}$ is acylamino having a hydroxy, and
R$^{2a}$ is a protected carboxy.

The starting compound (II) is novel and can be prepared by reacting the corresponding 2-lower alkyl-2-halomethyl-6-substituted penam-3-carboxylic acid or its 1-oxide or derivative at the carboxy group thereof with a base.

In the above and subsequent description, the term "a substituted amino" in R¹ means suitable substituted amino groups which may include hydrazino, mono(or di)-(lower)alkylamino, mono(or di)-(lower)alkenylamino, lower alkylideneamino, phenyl(lower)alkyl-ideneamino, 2,2-di(lower)alkyl-4-phenyl-5-oxoimidazolidin-1-yl, acylamino and amino group substituted by other amino protecting groups than the acyl groups.

In the above suitable substituted amino group, suitable lower alkyl moiety in the mono(or di)-lower alkylamino may include methyl, ethyl, propyl, isopropyl, butyl, etc.; suitable lower alkenyl moiety in the mono(or di)-lower alkenylamino may include, allyl, 2-butenyl, etc.; suitable lower alkylidene moiety in the lower alkylideneamino may include ethylidene, propylidene, butylidene, etc.; suitable phenyl(lower)alkylidene moiety in the phenyl(lower)-alkylidene may include benzylidene, phenethylidene, etc.; suitable 2,2-di(lower)alkyl-4-phenyl-5-oxoimidazolidin-1-yl may include 2,2-dimethyl-4-phenyl-5-oxoimidazolidin-1-yl, 2,2-diethyl-4-phenyl-5-oxoimidazolidin-1-yl, etc.; suitable acyl moiety in the acylamino groups may include carbamoyl, aliphatic acyl groups and acyl groups containing an aromatic or heterocyclic ring, examples of which are illustrated below.

That is, suitable aliphatic acyl groups may include saturated or unsaturated, lower or higher alkanoyl groups which may be branched or which may contain a cyclic ring; such as lower or higher aliphatic acyl groups, for example, lower alkanoyl (e.g., formyl, acetyl, propionyl, butyryl, isobutyryl, valeryl, isovaleryl, oxalyl, succinyl, pivaloyl, etc.), higher alkanoyl (e.g., octanoyl, lauroyl, palmitoyl, etc.), lower alkenoyl (e.g., acryloyl, crotonoyl, etc.), lower alkynoyl (e.g., propynoyl, etc.), lower or higher cycloalkanecarbonyl (e.g., cyclopentanecarbonyl cyclohexanecarbonyl, cycloheptanecarbonyl, etc.), lower or higher cycloalkyl(lower)alkanoyl (e.g., cyclopentylacetyl, cyclohexylacetyl, cycloheptylacetyl, cyclohexylpropionyl, cycloheptylpropionyl, etc.), lower or higher cycloalkadiene carbonyl (e.g., dihydrobenzoyl, etc.), lower or higher cycloalkadienyl(lower)alkanoyl (e.g., dihydrophenylacetyl, dihydrophenylpropionyl, etc.), etc.; and lower or higher aliphatic acyl groups containing a oxygen or sulfur atom, for example, lower alkoxy(lower)alkanoyl (e.g., methoxyacetyl, ethoxyacetyl, methoxypropionyl, etc.), lower alkylthio(lower)alkanoyl (e.g., methylthioacetyl, ethylthioacetyl, methylthiopropionyl, etc.), lower alkenylthio(lower)alkanoyl (e.g., allylthioacetyl, allylthiopropionyl, etc.), lower or higher cycloalkylthio(lower)alkanoyl (e.g., cyclopentylthioacetyl, cyclohexylthiopropionyl, cycloheptylthioacetyl, etc.), lower or higher cycloalkoxy(lower)alkanoyl (e.g., cyclopentyloxyacetyl, cyclohexyloxypropionyl, etc.), lower or higher cycloalkanedienyloxy(lower)alkanoyl (e.g., dihydrophenoxy-acetyl, dihydrophenoxypropionyl, etc.), lower or higher cycloalkanedienylthio(lower)alkanoyl (e.g., dihydrophenylthioacetyl, dihydrophenylthiopropionyl, etc.), lower alkoxycarbonyl (e.g., methoxycarbonyl, ethoxycarbonyl, propoxycarbonyl, 1-cyclopropylethoxycarbonyl, isopropoxycarbonyl, butoxycarbonyl, tertiarybutoxycarbonyl, etc.), lower or higher cycloalkyloxycarbonyl (e.g., cyclopentyloxycarbonyl, cyclohexyloxycarbonyl, cycloheptyloxycarbonyl, etc.), lower or higher cycloalkanedienyloxycarbonyl (e.g., dihydrophenoxycarbonyl, etc.), etc.

Suitable acyl groups containing an aromatic ring such as benzene, naphthalene and the like may include, for example, phenylcarbamoyl, benzoyl, toluoyl, naphthoyl, α-methylnaphthoyl, phthaloyl, benzenesulfonyl, tetrahydronaphthoyl, indancarbonyl, ar(lower)alkanoyl (e.g., phenylacetyl, phenylpropionyl, phenylbutyryl, tolylacetyl, xylylacetyl, naphthylacetyl, tetrahydronaphthylacetyl, indanylacetyl, etc.), and the carbon atom in the alkyl moiety of said ar(lower)alkanoyl group may be replaced by an oxygen or sulfur atom or carbonyl group, example of which are phenoxy(lower)alkanoyl (e.g., phenoxyacetyl, phenoxypropionyl, phenoxybutyryl, etc.), xylyloxyacetyl, phenoxycarbonyl, xylyloxycarbonyl, naphthyloxycarbonyl, indanyloxycarbonyl, phenyl(lower)alkoxycarbonyl (e.g., benzyloxycarbonyl, phenethyloxycarbonyl, etc.), phenylthio(lower)alkanoyl (e.g., phenylthioacetyl, phenylthiopropionyl, etc.), phenylglyoxyloyl, etc.

Suitable acyl groups containing an heterocyclic ring may include heterocyclic carbonyl or heterocyclic lower alkanoyl; and the heterocyclic ring in the heterocyclic carbonyl or heterocyclic lower alkanoyl may be saturated or unsaturated, monocyclic or polycyclic and may contain at least one heteroatom, such as an oxygen, sulfur, nitrogen atom or the like, examples of which are illustrated by unsaturated 3 to 8-membered heteromonocyclic containing a sulphur atom (e.g., thienyl, etc.), unsaturated condensed-heterocyclic containing a sulfur atom (e.g., benzothienyl, etc.), unsaturated 3 to 8-membered heteromonocyclic containing an oxygen atom (e.g., furyl, 2(or 4)-pyranyl, dihydropyranyl, etc.), unsaturated 3 to 8-membered heteromonocyclic containing 1 to 4 nitrogen atom(s) (e.g., pyrrolyl, 2(or 3)H-pyrrolyl, 2(or 3)pyrrolinyl, imidazolyl, pyrazolyl, pyridyl, pyrimidyl, pyrazinyl, pyridazinyl, 1H-tetrazolyl, 2H-tetrazolyl, etc.), saturated 3 to 8-membered heteromonocyclic containing 1 to 2 nitrogen atom(s) (e.g., pyrrolidinyl, imidazolidinyl, piperidino, piperadinyl, etc.), unsaturated condensed-heterocyclic containing 1 to 3 nitrogen atom(s) (e.g., indolyl, isoindolyl, indolizinyl, benzimidazolyl, quinolyl, isoquinolyl, 1(or 2)H-indazolyl, 1(or 2)H-benzotriazolyl, etc.), unsaturated 3 to 8-membered heteromonocyclic containing an oxygen atom(s) and 1 to 3 nitrogen atom(s) (e.g., oxazolyl, isoxazolyl, oxadiazolyl, etc.), saturated 3 to 8-membered heteromonocyclic containing 1 to 2 oxygen atom(s) and 1 to 2 nitrogen atom(s) (e.g., sydnonyl, etc.), unsaturated 3 to 8-membered heteromonocyclic containing a sulfur atom and 1 to 3 nitrogen atom(s) (e.g., thiazolyl, thiadiazolyl, etc.), unsaturated condensed-heterocyclic containing an oxygen atom and 1 to 2 nitrogen atom(s) (e.g., benzoxazolyl, benzoxadiazolyl, etc.) and unsaturated condensed-heterocyclic containing a sulfur atom and 1 to 2 nitrogen atom(s) (e.g., benzothiazolyl, benzothiadiazolyl, etc.), etc. And, the carbon atom in the lower alkyl moiety in said heterocyclic lower alkanoyl as mentioned above may be replaced by an oxygen or sulfur atom examples of which are heterocyclic lower alkoxycarbonyl, heterocyclicoxycarbonyl, heterocyclic-oxy(lower)alkanoyl and heterocyclic-thio(lower)alkanoyl.

Further, the carbamoyl, the aliphatic acyl groups and the acyl groups containing an aromatic or heterocyclic ring as mentioned above may have 1 to 10 appropriate, substituent(s) such as lower alkyl (e.g., methyl, ethyl, propyl, isopropyl, etc.), lower alkenyl (e.g., 1-propenyl, allyl, etc.), lower or higher cycloalkyl (e.g., cyclopropyl, cyclopentyl, cyclohexyl, cycloheptyl, etc.), lower alkoxy (e.g., methoxy, ethoxy, propoxy, isopropoxy, etc.), lower alkylthio (e.g., methylthio, ethylthio, etc.), phenyl, xylyl, tolyl, indanyl, phenyl(lower)-alkyl (e.g., benzyl, phenethyl, etc.), halogen (e.g., chlorine, bromine, fluorine, etc.), halophenyl (e.g., chlorophenyl, bromophenyl, etc.), halophenoxy (e.g., chlorophenoxy, bromophenoxy, etc.), cyano, lower alkylsulfinyl (e.g., methylsulfinyl, ethylsulfinyl, etc.), lower alkanesulfonyl (e.g., methanesulfonyl, ethanesulfonyl, etc.), lower alkoxycarbonyl(lower)alkoxy (e.g., methoxycarbonylmethoxy, ethoxycarbonylethoxy, 1-cyclopropylethoxycarbonylmethoxy, tertiarybutoxycarbonylmethoxy, etc.), nitro, sulfo, amino, azido, mercapto, carboxy, hydroxy, hydroxyamino, mono(or di)alkylamino (e.g., mono(or di)methylamino, mono(or di)ethylamino, mono(or di)propylamino, mono(or di)isopropylamino, etc.), imino, carboxy(lower)alkoxy (e.g., carboxymethyl, etc.), etc.

The acyl group as mentioned above may have a functional group, such as amino, hydroxy, mercapto, carboxy, etc., and the functional group may also be protected by an appropriate protective group. Suitable protective group for the amino group may include any of the conventional protective group, for example, the acyl groups or other groups than the acyl groups such as trityl, 2-nitrophenylthio, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcyclohexylidene, 2-ethoxycarbonylcyclopentylidene, 2-acetylcyclohexylidene, 3,3-dimethyl-5-oxocyclohexylidene(among these, 1-methoxycarbonyl-2-propylidene and 2-ethoxycarbonylcyclohexylidene groups may be representable as 1-methoxycarbonyl-1-propene-2-yl and 2-ethoxycarbonyl-1-cyclohexenyl group, respectively), mono(or di)silyl, etc.; suitable protective groups for hydroxy or mercapto groups may include any of the conventional protective groups for hydroxy or mercapto groups, for example, the acyl groups or other groups than the acyl group such as benzyl, trityl, methoxymethyl, 2-nitrophenylthio, 2,4-dinitrophenylthio, etc.; and suitable protective groups for the carboxy group may include any of those conventional protective groups used for protecting a carboxy group, for example, lower alkyl ester (e.g., methyl ester, ethyl ester, propyl ester, butyl ester, 1-cyclopropylethyl ester, tertiarybutyl ester, etc.), mono(or di or tri)halo(lower)alkyl ester (e.g., chloromethyl ester, 2,2,2-trichloroethyl ester, 3,3-dibromopropyl ester, etc.), phenyl ester, nitrophenyl ester, indanyl ester, mono(or di or tri)phenyl(lower)alkyl ester(e.g., benzyl ester, diphenylmethyl ester, triphenylmethyl ester etc.), p-nitrobenzyl ester, p-bromobenzyl ester, tri(lower)alkylsilyl ester (e.g., trimethylsilyl ester, triethylsilyl ester, etc.), etc.

Further, as the amino protective group other than an acyl group which is mentioned in the above paragraph for explanation of the term "a substituted amino", there may be also illustrated the same amino protective groups as those which are examplified as the protective groups for the amino radical in the acyl group as mentioned above.

Particularly suitable examples of the acyl groups may be illustrated as follows:
(1) lower alkoxycarbonyl (e.g., methoxycarbonyl, ethoxycarbonyl, propoxycarbonyl, 1-cyclopropylethoxycarbonyl, butoxycarbonyl, tertiarybutoxycarbonyl, etc.),
(2) phenyl(lower)alkoxycarbonyl (e.g., benzyloxycarbonyl, phenethyloxycarbonyl, etc.),
(3) phenylcarbamoyl,
(4) phenylglyoxyloyl,
(5) lower alkoxyphenylglyoxyloyl (e.g., 2-[2-(or 3- or 4-)methoxyphenyl]glyoxyloyl, 2-[2-(or 3- or 4-)ethoxyphenyl]glyoxyloyl, etc.), (6) phenylthiocarbonyl,
(7) cyano(lower)alkanoyl (e.g., 2-cyanoacetyl, 3-cyanopropionyl, 4-cyanobutyryl, etc.),
(8) lower alkylthio(lower)alkanoyl (e.g., 2-methyl-thioacetyl, 2-methylthiobutyryl, 2-ethylthioacetyl, 3-methylthiopropionyl, etc.),
(9) lower alkenylthio(lower)alkanoyl (e.g., 2-allylthioacetyl, 3-allylthiopropionyl, etc.),
(10) phenylthio(lower)alkanoyl (e.g., 2-phenylthioacetyl, 3-phenylthiopropionyl, etc.),
(11) phenoxy(lower)alkanoyl (e.g., 2-phenoxyacetyl, 3-phenoxypropionyl, 4-phenoxybutyryl, etc.),
(12) phenyl(lower)alkanoyl (e.g., 2-phenylacetyl, 3-phenylpropionyl, 4-phenylbutyryl, etc.),
(13) halophenyl(lower)alkanoyl (e.g., 2-[2-(or 3- or 4-)chlorophenyl]acetyl, 2-[2-(or 3- or 4-)bromophenyl]acetyl, 3-[2-(or 3- or 4-)chlorophenyl]-propionyl, etc.),
(14) phenyl and amino substituted lower alkanoyl (e.g., phenylglycyl, 3-amino-3-phenylpropionyl, etc.),
(15) phenyl and lower alkoxycarbonylamino substituted lower alkanoyl (e.g., N-methoxycarbonylphenylglycyl, N-ethoxycarbonylphenylglycyl, N-(1-cyclopropylethoxy)-carbonyl-phenylglycyl, N-tertiarybutoxycarbonylphenylglycyl, 2-(1-cyclopropylethoxy)-carbonylamino-3-phenylpropionyl, etc.),

(16) phenyl and trihalo(lower)alkoxycarbonylamino substituted lower alkanoyl (e.g., N-trichloroethoxycarbonylphenylglycyl, 3-trichloroethoxycarbonylamino-3-phenylpropionyl, N-tribromoethoxycarbonylphenylglycyl, etc.),

(17) phenyl and nitrophenoxy(lower)alkanoylamino substituted lower alkanoyl (e.g., N-[2-[2-(or 3- or 4-)nitrophenoxy]acetyl]phenylglycyl, etc.),

(18) phenyl and thiadiazolylthio(lower)alkanoylamino substituted lower alkanoyl (e.g., N-(1,3,4-thiadiazol-2-yl)thioacetylphenylglycyl, 2-[3-(1,3,4-thiadiazol-2-yl)thiopropionyl]amino-3-phenylpropionyl, etc.),

(19) hydroxyphenyl and amino substituted lower alkanoyl (e.g., 2-amino-2-[2-(or 3- or 4-)hydroxyphenyl]acetyl, 2-amino-3-[2-(or 3- or 4-)hydroxyphenyl]propionyl, etc.),

(20) hydroxyphenyl and lower alkoxycarbonylamino substituted lower alkanoyl (e.g., 2-methoxycarbonylamino-2-[2-(or 3- or 4-)hydroxyphenyl]acetyl, 2-(1-cyclopropylethoxy)carbonylamino-2-[2-(or 3- or 4-)hydroxyphenyl]acetyl, 2-tertiarybutoxycarbonylamino-2-[2-(or 3- or 4-)hydroxyphenyl]acetyl, etc.),

(21) lower alkoxyphenyl and amino substituted lower alkanoyl (e.g., 2-amino-2-[2-(or 3- or 4-)methoxyphenyl]acetyl, 2-amino-3-[2-(or 3- or 4-)methoxyphenyl]acetyl, etc.),

(22) lower alkoxyphenyl and lower alkoxycarbonylamino substituted lower alkanoyl (e.g., 2-methoxycarbonylamino-2-[2-(or 3- or 4-)methoxyphenyl]acetyl, 2-(1-cyclopropylethoxy)carbonylamino-2-[2-(or 3- or 4-)methoxyphenyl]acetyl, 2-tertiarybutoxycarbonylamino-2-[2-(or 3- or 4-)methoxyphenyl]acetyl, etc.),

(23) lower alkylthiophenyl and amino substituted lower alkanoyl (e.g., 2-amino-2-[2-(or 3- or 4-)-methylthiophenyl]acetyl, 2-amino-3-[2-(or 3- or 4-)ethylthiophenyl]-propionyl, etc.),

(24) lower alkylthiophenyl and lower alkoxycarbonylamino substituted lower alkanoyl (e.g., 2-methoxycarbonylamino-2-[2-(or 3- or 4-)methylthiophenyl]-acetyl, 2-(1-cyclopropylethoxy)carbonylamino-2-[2-(or 3- or 4-)methylthiophenyl]acetyl, 2-tertiary-butoxycarbonylamino-2-[2-(or 3- or 4-)methylthiophenyl]acetyl, 2-tertiarybutoxycarbonylamino-3-[2-(or 3- or 4-)ethylthiophenyl]propionyl, etc.),

(25) lower alkylsulfinylphenyl and amino substituted lower alkanoyl (e.g., 2-amino-2-[2-(or 3- or 4-)methylsulfinylphenyl]acetyl, 2-amino-3-[2-(or 3- or 4-)ethylsulfinylphenyl]propionyl, etc.),

(26) lower alkylsulfinylphenyl and lower alkoxycarbonylamino substituted lower alkanoyl (e.g., 2-methoxycarbonylamino-2-[2-(or 3- or 4-)methylsulfinylphenyl]acetyl, 2-(1-cyclopropylethoxy)carbonylamino3-[2-(or 3- or 4-)ethylsulfinylphenyl]propionyl, 2-tertiarybutoxycarbonylamino-2-[2-(or 3- or 4-)methylsulfinylphenyl]acetyl, etc.),

(27) carboxy(lower)alkoxyphenyl and amino substituted lower alkanoyl (e.g., 2-amino-2-[2-(or 3- or 4-)carboxymethoxyphenyl]acetyl, 2-amino-3-[2-(or 3- or 4-)carboxymethoxyphenyl]propionyl, etc.),

(28) lower alkoxycarbonyl(lower)alkoxyphenyl and lower alkoxycarbonylamino substituted lower alkanoyl (e.g., 2-methoxycarbonylamino-2-[2-(or 3- or 4-)-methoxycarbonylmethoxyphenyl]acetyl, 3-(1-cyclopropylethoxy)carbonylamino-3-[2-(or 3- or 4-)ethoxycarbonylmethoxyphenyl]propionyl, 2-tertiarybutoxycarbonylamino-2-[2-(or 3- or 4-)tertiarybutoxycarbonylmethoxyphenyl]acetyl, etc.),

(29) lower alkanesulfonamidophenyl and lower alkoxycarbonylamino substituted lower alkanoyl (e.g., 2-methoxycarbonylamino-2-[2-(or 3- or 4-)methanesulfonamidophenyl]acetyl, 3-(1-cyclopropylethoxy)carbonylamino-3-[2-(or 3- or 4-)ethanesulfonamidophenyl]propionyl, 2-tertiarybutoxycarbonylamino-2-[2-(or 3- or 4-)methanesulfonamidophenyl]acetyl, etc.),

(30) dihydrophenyl and amino substituted lower alkanoyl (e.g., 2-amino-2-(2,5-dihydrophenyl)acetyl, 2-amino-3-(2,5-dihydrophenyl)propionyl, etc.),

(31) dihydrophenyl and lower alkoxycarbonylamino substituted lower alkanoyl (e.g., 2-methoxycarbonylamino-2-(2,5-dihydrophenyl)acetyl, 2-(1-cyclopropylethoxy)carbonylamino-2-(2,5-dihydrophenyl)acetyl, 2-tertiarybutoxycarbonylamino-3-(2,5-dihydrophenyl)propionyl, etc.),

(32) phenyl and azido substituted lower alkanoyl (e.g., 2-azido-2-phenylacetyl, 3-azido-3-phenylpropionyl, etc.),

(33) phenyl and hydroxy substituted lower alkanoyl (e.g., 2-hydroxy-2-phenylacetyl, 2-hydroxy-3-phenylpropionyl, etc.),

(34) phenyl and lower alkanoyloxy substituted lower alkanoyl (e.g., 2-formyloxy-2-phenylacetyl, 2-acetoxy-2-phenylacetyl, 3-propionyloxy-3-phenylpripionyl, etc.),

(35) phenyl and pyridylcarbonyloxy substituted lower alkanoyl (e.g., 2-nicotinoyloxy-2-phenylacetyl, 2-isonicotinoyloxy-2-phenylacetyl, etc.),

(36) phenyl and sulfo substituted lower alkanoyl (e.g., 2-phenyl-2-sulfoacetyl, 3-phenyl-3-sulfopropionyl, etc.),

(37) phenyl and indanyloxycarbonyl substituted lower alkanoyl (e.g., 2-(5-indanyloxy)carbonyl-2-phenylacetyl, 3-(5-indanyloxy)carbonyl-3-phenylacetyl, etc.),

(38) thienyl(lower)alkanoyl (e.g., 2-(2-thienyl)acetyl, 3-(2-thienyl)propionyl, etc.),

(39) thienyl and amino substituted lower alkanoyl (e.g., 2-amino-2-(2-thienyl)acetyl, 2-amino-3-(2-thienyl)propionyl, etc.),

(40) thienyl and lower alkoxycarbonylamino substituted lower alkanoyl (e.g., 2-methoxycarbonylamino2-(2-thienyl)acetyl, 2-(1-cyclopropylethoxy)carbonylamino-2-(2-thienyl)acetyl, 2-tertiarybutoxycarbonylamino-2-(2-thienyl)acetyl, 3-tertiarybutoxycarbonylamino-3-(2-thienyl)propionyl, etc.),

(41) thienyl and hydroxy substituted lower alkanoyl (e.g., 2-hydroxy-2-(2-thienyl)acetyl, 3-hydroxy-3-(2-thienyl)propionyl, etc.),

(42) dihydropyranyl and amino substituted lower alkanoyl (e.g., 2-amino-2-(5,6-dihydro-2H-pyran-3-yl)acetyl, 2-amino-3-(5,6-dihydro-2H-pyran-3-yl)propionyl, etc.),

(43) dihydropyranyl and lower alkoxycarbonylamino substituted lower alkanoyl (e.g., 2-methoxycarbonylamino-2-(5,6-dihydro-2H-pyran-3-yl)acetyl, 2-(1-cyclopropylethoxy)carbonylamino-2-(5,6-dihydro-2H-pyran-3-yl)acetyl, 2-tertiarybutoxycarbonylamino-2-(5,6-dihydro-2H-pyran-3-yl)acetyl, 2-tertiarybutoxycarbonylamino-3-(5,6-dihydro-2H-pyran-3-yl)-propionyl, etc.),

(44) pyridyl substituted lower alkanoyl (e.g., 2-(3-pyridyl)acetyl, 3-(3-pyridyl)propionyl, etc.),

(45) thiadiazolyl(lower)alkanoyl (e.g., 2-(1,2,5-thiadiazol-3-yl)acetyl, 2-(1,3,4-thiadiazol-2-yl)-acetyl, 3-(1,2,5-thiadiazol-3-yl)propionyl, etc.),
(46) lower alkylthiadiazolyloxy(lower)alkanoyl (e.g., 2-(5-methyl-1,3,4-thiadiazol-2-yloxy)acetyl, 2-(4-methyl-1,2,5-thiadiazol-3-yloxy)acetyl, 2-(5-ethyl-1,3,4-thiadiazol-2-yloxy)propionyl, etc.),
(47) thiadiazolylthio(lower)alkanoyl (e.g., 2-(1,3,4-thiadiazol-2-ylthio)acetyl, 2-(1,2,5-thiadiazol-3-ylthio)acetyl, 3-(1,3,4-thiadiazol-2-ylthio)propionyl, etc.),
(48) tetrazolyl(lower)alkanoyl (e.g., 2-(1H-tetrazol-1-yl)acetyl, 3-(1H-tetrazol-1-yl)propionyl, 4-(1H-tetrazol-1-yl)butyryl, etc.),
(49) 3-halophenyl-5-lower alkylisoxazol-4-ylcarbonyl (e.g., 3-[2-(or 3- or 4-)chlorophenyl]-5-methylisoxazol-4-ylcarbonyl, 3-[2-(or 3- or 4-)bromophenyl]-5-ethylisoxazol-4-ylcarbonyl, etc.),
(50) halobenzotriazolyl(lower)alkanoyl (e.g., 2-[4-(or 5- or 6- or 7-)chloro-1H-benzotriazol-1-yl]-acetyl, 2-[4-(or 5- or 6- or 7-)bromo-1H-benzotriazol-1-yl]acetyl, 3-[4-(or 5- or 6- or 7-)fluoro-2H-benzotriazol-2-yl]propionyl, etc.),
(51) sydnonyl(lower)alkanoyl (e.g., 2-(sydnon-3-yl)acetyl, 3-(sydnon-3-yl)propionyl, etc.),
(52) phthaloyl,
(53) lower alkanoylaminobenzenesulfonyl (e.g., 2-(or 3- or 4-)acetamidobenzenesulfonyl, 2-(or 3- or 4-)propionamidobenzenesulfonyl, etc.),
(54) phenyl and halophenoxy substituted lower alkanoyl (e.g., 2-phenyl-2-[2-(or 3- or 4-)chlorophenoxy]acetyl, 2-phenyl-2-[2-(or 3- or 4-)bromophenoxy]acetyl, etc.),
(55) aminothiazolyl(lower)alkanoyl (e.g., 2-(2-aminothiazolyl)acetyl, 3-(2-aminothiazolyl)propionyl, etc.),
(56) imino-2,3-dihydrothiazolyl(lower)alkanoyl (e.g., 2-(2-imino-2,3-dihydrothiazolyl)acetyl, etc.), etc.

The term "a protected amino" in $R^{1a}$ and in the acylamino having a protected amino for $R^{1c}$ may include acylamino and amino group substituted by other amino protecting groups than the acyl groups as illustrated above.

The term "a protected hydroxy" in the acylamino having a protected hydroxy may include hydroxy protected by the same conventional protective groups for hydroxy as illustrated above.

The term "acylamino" in $R^{1b}$, $R^{1b'}$, the acylamino having a protected amino for $R^{1c}$, the acylamino having an amino for $R^{1d}$, the acylamino having a protected hydroxy for $R^{1e}$ and the acylamino having a hydroxy for $R^{1f}$ may include the same acylamino as illustrated above:

The term "a protected carboxy group" in $R^2$ and $R^{2a}$ may include ester, acid amide, acid anhydride, etc.

Suitable esters may include silyl esters, aliphatic esters and esters containing an aromatic or heterocyclic ring. The suitable silyl esters may be illustrated by examples tri(lower)alkylsilyl (e.g., trimethylsilyl, triethylsilyl, etc.) esters, etc. The suitable aliphatic esters may include saturated or unsaturated, lower or higher alkyl esters which may be branched or which may contain a cyclic ring, such as lower or higher aliphatic esters, for example, lower alkyl (e.g., methyl, ethyl, propyl, isopropyl, 1-cyclopropylethyl, butyl, tertiarybutyl, etc.) esters, higher alkyl (e.g., octyl, nonyl, undecyl, etc.) esters, lower alkenyl (e.g., vinyl, 1-propenyl, allyl, 3-butenyl, etc.) esters, lower alkynyl (e.g., 3-butynyl, 4-pentynyl, etc.) esters, lower or higher cycloalkyl (e.g., cyclopentyl, cyclohexyl, cycloheptyl, etc.) esters, etc., and lower or higher aliphatic esters containing a nitrogen, sulfur or oxygen atom, for example, lower alkoxy(lower)alkyl (e.g., methoxymethyl, ethoxyethyl, methoxyethyl, etc.) esters, lower alkylthio(lower)alkyl (e.g., methylthiomethyl, ethylthioethyl, methylthiopropyl, etc.) esters, di(lower)alkylamino (e.g., dimethylamino, diethylamino, dipropylamino, etc.) esters, lower alkylideneamino (e.g., ethylideneamino, propylideneamino, isopropylideneamino, etc.) esters, lower alkylsulfenyl(lower)alkyl (e.g., methylsulfenylmethyl, ethylsulfenylmethyl, etc.) esters, etc.

The suitable esters containing an aromatic ring may include, for example, phenyl ester, xylyl ester, tolyl ester, naphthyl ester, indanyl ester, dihydroanthryl ester, phenyl(lower)alkyl (e.g., benzyl, phenethyl, etc.) esters, phenoxy(lower)alkyl (e.g., phenoxymethyl, phenoxyethyl, phenoxypropyl, etc.) esters, phenylthio(lower)alkyl (e.g., phenylthiomethyl, phenylthioethyl, phenylthiopropyl, etc.) esters, phenylsulfenyl(lower)alkyl (e.g., phenylsulfenylmethyl, phenylsulfenylethyl, etc.) esters, benzoyl(lower)alkyl (e.g., benzoylmethyl, benzoyl ethyl, etc.) esters, phthalimido ester, etc.;

The suitable esters containing an heterocyclic ring may include, for example, heterocyclic esters, heterocyclic lower alkyl esters, etc.; in which the suitable heterocyclic esters may include, for example, saturated or unsaturated, condensed or uncondensed 3 to 8-membered heterocyclic containing 1 to 4 hetero-atom(s) such as an oxygen, sulfur and nitrogen atom (e.g., pyridyl, piperidino, 2-pyridon-1-yl, tetrahydropyranyl, quinolyl, pyrazolyl, etc.) esters, etc., and the suitable heterocyclic lower alkyl esters may include, for example, saturated or unsaturated, condensed or uncondensed 3 to 8-membered heterocyclic containing 1 to 4 hetero-atom(s) such as an oxygen, sulfur and nitrogen atom (e.g., pyridyl, piperidino, 2-pyridon-1-yl, tetrahydropyranyl, quinolyl, pyrazolyl, etc.) substituted lower alkyl (e.g., methyl, ethyl, propyl, etc.) esters, etc.;

The silyl esters, the aliphatic esters and the esters containing an aromatic or heterocyclic ring as mentioned above may have 1 to 10 appropriate substituent(s) such as lower alkyl (e.g., methyl, ethyl, propyl, isopropyl, butyl, tertiarybutyl, etc.), lower alkoxy (e.g., methoxy, ethoxy, propoxy, isopropoxy, butoxy, tertiarybutoxy, etc.), lower alkylthio (e.g., methylthio, ethylthio, propylthio, etc.), lower alkylsulfinyl (e.g., methylsulfinyl, ethylsulfinyl, propylsulfinyl, etc.), lower alkanesulfonyl (e.g., methanesulfonyl, ethanesulfonyl, etc.), phenylazo, halogen (e.g., chlorine, bromine, fluorine, etc.), cyano, nitro, etc., examples of which are illustrated by mono(or di or tri)halo(lower)alkyl (e.g., chloromethyl, bromoethyl, dichloromethyl, 2,2,2-trichloroethyl, 2,2,2-tribromoethyl, etc.) esters, cyano(lower)alkyl (e.g., cyanomethyl, cyanoethyl, etc.) esters, mono(or di or tri or tetra or penta)halophenyl (e.g., 4-chlorophenyl, 3,5-dibromophenyl, 2,4,5-trichlorophenyl, 2,4,6-trichlorophenyl, pentachlorophenyl, etc.) esters, lower alkanesulfonylphenyl (e.g., 4-methanesulfonylphenyl, 2-ethanesulfonylphenyl, etc.) esters, 2-(or 3- or 4-)phenylazophenyl esters, mono(or di or tri)nitrophenyl (e.g., 4-nitrophenyl, 2,4-dinitrophenyl, 3,4,5-trinitrophenyl, etc.) esters, mono(or di or tri or tetra or penta)halophenyl(lower)alkyl (e.g., 2-chlorobenzyl, 2,4-dibromobenzyl, 3,4,5-trichlorobenzyl, pentachlorobenzyl, etc.) esters, mono(or di or tri)nitrophenyl(lower)alkyl (e.g., 2-nitrobenzyl, 2,4-dinitrobenzyl, 3,4,5-trinitrobenzyl, etc.) esters, mono(or di or tri) (lower)alkoxyphenyl(lower)alkyl, (e.g., 2-methoxybenzyl, 3,4- dimethoxybenzyl, 3,4,5-trimethoxybenzyl, etc.) esters, hydroxy and di(lower)alkylphenyl(lower)alkyl (e.g., 3,5-dimethyl-4-hydroxybenzyl, 3,5-ditertiarybutyl-4-hydroxybenzyl, etc.) esters, lower alkanoyloxy(lower)alkyl (e.g., acetoxymethyl, propionyloxyethyl, pivaloyloxymethyl, etc) esters, etc.

The suitable acid amides may include, for example, N-lower alkyl acid amide (e.g., N-methyl acid amide, N-ethyl acid amide, etc.), N,N-di(lower)alkyl acid amide (e.g., N,N-dimethyl acid amide, N,N-diethyl acid amide, N-methyl-N-ethyl acid amide, etc.), N-phenyl acid amide, or an acid amide with pyrazole, imidazole, 4-lower alkylimidazole (e.g., 4-methylimidazole, 4-ethylimidazole, etc.), etc.

The suitable acid anhydrides include, for example, an acid anhydride with a di(lower)alkyl phosphate (e.g., dimethyl phosphate, diethyl phosphate, etc.), dibenzylphosphate, phosphoric acid halide (e.g., phosphoric acid chloride, phosphoric acid bromide, etc.), di(lower)alkyl phosphite (e.g., dimethyl phosphite, diethyl phosphite, etc.), sulfurous acid, thiosulfuric acid, sulfuric acid, lower alkyl carbonate (e.g., methyl carbonate, ethyl carbonate, etc.), hydrazoic acid, hydrohalogenic acid (e.g., hydrochloric acid, hydrobromic acid, etc.), saturated or unsaturated lower aliphatic carboxylic acid (e.g., pivalic acid, pentanoic acid, isopentanoic acid, 2-ethylbutanoic acid, crotonic acid, valeric acid, propionic acid, etc.), saturated or unsaturated halo(lower)aliphatic carboxylic acid (e.g., chloroacetic acid, 3-chloro-2-pentenoic acid, 3-bromo-2-butenoic acid, etc.), substituted lower aliphatic carboxylic acid (e.g., phenylacetic acid, phenoxyacetic acid, furanacetic acid, thiopheneacetic acid, etc.), aromatic carboxylic acid (e.g., benzoic acid, etc.), or a symmetric acid anhydride, etc.

The term "lower alkyl" in $R^3$, $R^5$ and $R^6$ means the one having straight, branched or cyclic to 1 to 6 carbon chain such as methyl, ethyl, propyl, isopropyl, butyl, tert-butyl, cyclohexyl, etc.:

The term "aryl" in $R^4$ means, for example, phenyl, naphthyl, etc.

In the above and subsequent description, the term "lower" means one to six carbon chain and the term "higher" means seven to sixteen carbon chain, which may be branched or may contain a cyclic ring.

The object compound (I) in the present invention can be prepared by reacting the starting compound (II) with a Lewis acid.

Suitable Lewis acid used in this reaction includes, for example, boron halide (e.g., boron trichloride, boron tribromide, boron trifluoride, etc.), titanium halide (e.g., titanium tetrachloride, titanium tetrabromide, etc.), zirconium halide (e.g., zirconium tetrachloride, ziroconium tetrabromide, etc.) stannic halide (e.g., stannic chloride, stannic bromide, etc.), antimony halide (e.g., antimony trichloride, antimony pentachloride, etc.), bismuth chloride, aluminum halide (e.g., aluminum chloride, aluminum bromide, etc.), zinc chloride, ferric chloride, toluenesulfonic acid, polyphosphoric acid ester, sulfuric acid, trichloroacetic acid, trifluoroacetic acid, zinc sulfate, ferric sulfate, etc.

This reaction is usually carried out in the presence of a solvent.

Suitable solvent used in the present invention includes any solvent which does not adversely influence the reaction, for example, methylenechloride, chloroform, benzene, tetrahydrofuran, dimethylformamide, carbondisulfide, etc.

There is no particular limitation to the present reaction temperature, and the reaction can be usually carried out under mild conditions such as under cooling to at ambient temperature.

In the present reaction, the object compound (I) is sometimes obtained as a mixture of 2-cephem compound and 3-cephem compound and/or the 3-cephem stereomers at two position of the cephem ring, and, if necessary, these mixtures can be separated by conventional methods such as recrystallization.

The present invention includes, within its scope, the cases the carboxy group is changed into the protected carboxy group and the protected carboxy group is changed into the other protected carboxy groups or into the free carboxy group and the protected amino group is changed into the free amino group during the reaction or post-treating in the present reaction.

When the object compound (I) is used in the next step, it can be used with or without isolation and/or purification, i.e., it can be used as a mixture of 2-cephem compound and 3-cephem compound and/or the 3-cephem stereomers at two position of the cephem ring.

The object compound (Ib) can be prepared by oxidizing the compound (Ia). The present oxidizing reaction is carried out under conditions so that the —S— group can be changed into the

group.

Oxidation in the present reaction is conducted by a conventional method such as a method of using a oxidizing agent, for example, halogen (e.g., chlorine, bromine, etc.), halogen compound (e.g., isocyanuroylchloride, phenyliododichloride, etc.), ozone, inorganic per acid (e.g., periodic acid, persulfuric acid, etc.), organic per acid (e.g., perbenzoic acid, m-chloroperbenzoic acid, performic acid, peracetic acid, chloroperacetic acid, trifluoroperacetic acid, etc.), a metal salt of the inorganic or organic peracid, hydrogen peroxide, urea-hydrogen peroxide, etc.

The present reaction is preferably carried out in the presence of a compound comprising a Group Vb or VIb metal in the Periodic Table, for example, tungstic acid, molybdic acid, vanadic acid, or the like, or an alkali metal (e.g., sodium, potassium, etc.), alkaline earth metal (e.g., calcium, magnesium, etc.), ammonium salt thereof, or vanadium pentoxide.

The present oxidizing reaction is usually carried out in the presence of a solvent such as water, acetic acid, chloroform, methylene chloride, lower alcohol (e.g., methanol, ethanol, etc.), tetrahydrofuran, dioxane, dimethylformamide or any other solvent which does not adversely influence the present reaction.

There is no particular limitation to the reaction temperature, and the present reaction is usually carried out at ambient temperature or under cooling.

The present invention includes, within its scope, the cases that the carboxy group is changed into the protected carboxy group and the protected carboxy group is changed into the other protected carboxy group or into the free carboxy group and the protected amino group is changed into the free amino group during the reaction or post-treating in the present reaction.

The object compound (Ia) can be prepared by reducing the object compound (Ib).

The reducing reaction is carried out under conditions so that the

group can be changed into the —S— group.

Reduction in the present reaction is conducted by a conventional method such as a method of using stannous chloride or metal thiosulfate (e.g., sodium thiosulfate, potassium thiosulfate, etc.), or a combination of acid chloride and said stannous chloride or metal thiosulfate; or phosphorus trichloride, phosphrus pentachloride, silicon trichloride, etc. and a method described in Japanese patent official gazette No. 21111/1972.

The present reaction is usually carried out in a solvent which does not adversely influence the reaction, for example, dimethylformamide, acetonitrile, acetoacetic acid ester, tetrahydrofuran, chloroform, methylene chloride, dioxane, etc.

There is no limitation to the present reaction temperature, and it may be suitably selected according to the compound (Ib) and reduction method to be used in the reaction.

The present invention includes, within its scope, the cases that the carboxy group is changed into the protected carboxy group and the protected carboxy group is changed into the other protected carboxy group or into the free carboxy group and the protected amino group is changed into the free amino group during the reaction or post-treating in the present reaction.

The object compound (Id) can be prepared by subjecting the compound (Ic) to elimination reaction of the protective group of the amino and the object compound (Ih) can be prepared by subjecting the compound (Ig) to elimination reaction of the protective group of the amino, respectively.

The present elimination reaction is carried out in accordance with a conventional method such as hydrolysis, using an acid, treatment with hydrazine, reduction, and the like. These methods may be selected depending on kind of the protective groups to be eliminated. When the protective group is an acyl group, it may also be eliminated by treating with an iminohalogenating agent and then with an iminoesterifying agent, if necessary, followed by hydrolysis.

The elimination reaction with the acid is one of the most commonly applied methods for eliminating the protective groups such as benzyloxycarbonyl substituted benzyloxycarbonyl, alkoxycarbonyl, substituted alkoxycarbonyl, aralkoxycarbonyl, adamantyloxycarbonyl, trityl, substituted phenylthio, substituted aralkylidene, substituted alkylidene, substituted cycloalkylidene, etc. Suitable acid may include, for example, formic acid, trifluoroacetic acid, benzenesulfonic acid, p-toluenesulfonic acid, and the like, and the most suitable acid is an acid which can be easily distilled off under reduced pressure, for example, formic acid, trifluoroacetic acid, etc. The acid suitable for the reaction can be selected according to the protected group to be eliminated and other factors. When the elimination reaction is conducted with the acid, it can be carried out in the presence or absence of a solvent. Suitable solvent includes a hydrophilic organic solvent, water or a mixed solvent thereof. The elimination reaction with hydrazine is commonly applied for eliminating, for example, phthaloyl. The reduction is generally applied for eliminating, for example, trichloroethoxycarbonyl, benzyloxycarbonyl, substituted benzyloxycarbonyl, 2-pyridylmethoxycarbonyl, etc. The reduction applicable for the elimination reaction of the present invention may include, for example, reduction with a metal (e.g., tin, zinc, iron, etc.) or a combination of metallic compound (e.g., chromous chloride, chromous acetate, etc.) and an organic or inorganic acid (e.g., acetic acid, propionic acid, hydrochloric acid, etc.), and reduction in the presence of a metallic catalyst for catalytic reduction. The metallic catalyst for catalytic reduction may include, for example, Raney-nickel, platinum oxide, palladium carbon and other conventional catalysts.

The protective group, trifluoroacetyl can be usually eliminated by treating with water in the presence or absence of the base, and halogen substituted-alkoxycarbonyl and 8-quinolyloxycarbonyl are usually eliminated by treating with a heavy metal such as copper, zinc, etc.

When the protective group is acyl, the acyl can be eliminated by reacting with the iminohalogenating agent and then with the iminoetherifying agent, if necessary, followed by hydrolysis. Suitable iminohalogenating agents may include, for example, phosphorus trichloride, phosphrus pentachloride, phosphorus tribromide, phosphorus pentabromide, phosphorus oxychloride, thionyl chloride, phosgene, etc. Reaction temperature in iminohalogenation is not critical and the reaction sufficiently proceeds at ambient temperature or cooled one. Suitable iminoetherifying agents, with which the resultant in the iminohalogenating reaction is reacted, may include an alcohol such as an alkanol (e.g., methanol, ethanol, propanol, isopropanol, butanol, tertiary butanol, etc.) or the corresponding alkanol having alkoxy (e.g., methoxy, ethoxy, propoxy, isopropoxy, buthoxy, etc.) as substituent(s) at the alkyl moiety thereof, and a metal alkoxide such as alkali metal alkoxide (e.g., sodium alkoxide, potassium alkoxide, etc.) or alkaline earth metal alkoxide (e.g., calcium alkoxide, barium alkoxide, etc.), each of which is derived from the said alcohol. Reaction temperature in iminoetherification is also not limitative and the reaction sufficiently proceeds at ambient temperature or cooled one. Thus obtained reaction product is, if necessary, hydrolyzed. The hydrolysis sufficiently proceeds by pouring the reaction mixture to water or a mixture of water and a hydrophilic solvent such as methanol, ethanol, etc. In this hydrolysis, water may contain a base such as alkali metal bicarbonate, trialkylamine, etc. or an acid such as dilute hydrochloric acid, acetic acid, etc. When the protective group is acyl, the acyl can be also eliminated by hydrolysis as mentioned above or by the other conventional hydrolysis.

The reaction temperature is not limitative and may be suitably selected in accordance with the protective group for amino and the elimination method as mentioned above, and the present reaction is preferably carried out under a mild condition such as under cooling or slightly warming.

The present invention includes, within its scope, the cases that the protected carboxy group is changed into the other protected carboxy group or into the free carboxy group during the reaction or post-treating in the present reaction.

Thus obtained compounds (Id) and (Ih) can be converted to a desirable acid addition salt thereof by a conventional method, if necessary.

The object compound (Ie) can be prepared by reacting the compound (Id) or a salt thereof with an acylating agent.

Suitable salt of the compound (Id) may include organic acid salt (e.g., acetate, maleate, tartrate, benzenesulfonate, toluenesulfonate, etc.) and inorganic acid salt (e.g., hydrochloride, sulfate, phosphate, etc.), and the like.

As acylating agents in the present reaction, there may be exemplified an aliphatic, aromatic and heterocyclic carboxylic acid, and the corresponding sulfonic acid, carbonic acid ester, carbamic acid and thio acid, and the reactive derivatives of the above acids.

As the reactive derivatives, there may be exemplified and acid anhydride, an activated amide, an activated ester, an isocyanate and an isothiocyanate, etc., examples of which are illustrated by an acid azide, an mixed acid anhydride with an acid such as dialkylphosphoric acid, phenylphosphoric acid, diphenylphosphoric acid, dibenzylphosphoric acid, halogenated phosphoric acid, dialkylphosphorous acid, sulfurous acid, thiosulfuric acid, hydrohalogenic acid (e.g., hydrochloric acid, sulfuric acid, monoalkyl carbonate, aliphatic carboxylic acid (e.g., acetic acid, pivalic acid, pentanoic acid, isopentanoic acid, 2-ethylbutyric acid or trichloroacetic acid), aromatic carboxylic acid (e.g., benzoic acid), or symmetrical acid anhydride, an acid amide with pyrazole, imidazole, 4-substituted imidazole, dimethylpyrazole, triazole or tetrazole, an ester (e.g., cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or ester with N,N-dimethylhydroxylamine, 1-hydroxy-2-(1H)-pyridone, N-hydroxysuccinimide or N-hydroxyphthalimide).

The above reactive derivatives are selected according to the kind of the acid to be used. In the acylating reaction, when free acid is used, there may be preferably added a condensing agent such as N,N'-dicyclohexylcarbodiimide, N-cyclohexyl-N'-morpholinoethylcarbodiimide, N-cyclohexy-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonyldi-(2-methylimidazole), pentamethyleneketene-N-cyclohexylimide, diphenylketene-N-cyclohexylimine, alkoxyacetylene, 1-alkoxyl-1-chloroethylene, trialkyl phosphite, ethyl polyphosphate, isopropyl polyphosphate, phosphorus oxychloride, phosphorus trichloride, thionylchloride, oxalyl chloride, triphenylphosphine, 2-ethyl-7-hydroxybenzisoxazolium salt, 2-ethyl-5-(m-sulfophenyl)isoxazolium hydroxide intramolecular salt, (chloromethylene)-dimethylammonium chloride, 2,2,4,4,6,6-hexachloro-2,2,4,4,6,6-hexahydro-1,3,5,2,4,6-triazatriphosphorine, or a mixed condensing agent such as triphenylphosphine and a carbon tetrahalide (e.g., carbon tetrachloride, carbon tetrabromide, etc.) or a halogen (e.g., chlorine, bromine, etc.), and the like.

The example of an acyl group to be introduced into the amino group in the compound (Id) by the above acylating agent may be a group dehydroxylated from each of an aliphatic, aromatic and heterocyclic carboxylic acid, and the corresponding sulfonic acid, carbonic acid ester, carbamic acid and thio acid, etc., and more particular acyl group may be the same acyl group as illustrated in the explanation of the acyl group in the acylamino group for $R^1$.

The present acylating reaction is usually carried out in a solvent which does not adversely influence the reaction, for example, water, acetone, dioxane, acetonitrile, chloroform, methylene chloride, ethane dichloride, tetrahydrofuran, ethyl acetate, dimethylformamide, pyridine, etc., and the hydrophilic solvent mentioned above can be used as a mixed solvent with water.

The present acylating reaction can be carried out in the presence of a base such as inorganic base (e.g., alkali metal bicarbonate, etc.) and an organic base such as trialkylamine (e.g., trimethylamine, triethylamine, tributylamine, etc.), N-methylmorpholine, N-methylpiperidine, N,N-dialkyl-aniline (e.g., N,N-dimethylaniline, N,N-diethylaniline, etc.), N,N-dialkylbenzylamine (e.g., N,N-dimethylbenzylamine, N,N-diethylbenzylamine, etc.), pyridine, picoline, lutidine, 1,5-diazabicyclo[4,3,0]non-5-ene, 1,4-diazabicyclo[2,2,2]octane, 1,8-diazabicyclo[5,4,0]undecene-7, etc.

In the present reaction, a liquid base or liquid condensing agent can be also used as a solvent.

There is no limitation to the present reaction temperature, and the present reaction can be carried out at cooled or at ambient temperature.

The present invention may include the cases that the free carboxy group is changed into the protected carboxy group and the protected carboxy is changed into the other protected carboxy group or into the free carboxy group in the present reaction or post-treating in the present reaction.

The object compound (If) can be prepared by reacting the compound (Ie) with a trialkyloxoniumhaloborate or an iminohalogenating agent and an iminoetherifying agent, and then reacting the resulting compound with an acylating agent, if necessary, followed by hydrolysis.

Suitable trialkyloxoniumhaloborate includes, for example, trimethyloxoniumchloroborate, trimethyloxoniumfluoroborate, triethyloxoniumfluoroborate, etc.

Suitable iminohalogenating agents may include, for example, phosphorus trichloride, phosphorus pentachloride, phosphorus tribromide, phosphorus pentabromide, phosphorus oxychloride, thionyl chloride, phosgene, etc.

Suitable iminoetherifying agents, with which the resultant in the iminohalogenating reaction is reacted, may include an alcohol such as an alkanol (e.g., methanol, ethanol, propanol, isopropanol, butanol, tertiary butanol, etc.) or the corresponding alkanol having alkoxy (e.g., methoxy, ethoxy, propoxy, isopropoxy, buthoxy, etc.) as substituent(s) at the alkyl moiety thereof and a metal alkoxide such as alkali metal alkoxide (e.g., sodium alkoxide, potassium alkoxide, etc.) or alkaline earth metal akoxide (e.g., calcium alkoxide, barium alkoxide, etc.) derived from the said alcohol.

These reactions are usually carried out in a solvent which does not give bad influence to these reactions, for example, chloroform, methylene chloride, tetrahydrofuran, dioxane, etc.

There are no particular limitation to these reaction temperature, and these reactions are often carried out at ambient or cooled temperature.

The acylating reaction can be carried out under the similar conditions as described in the acylating reaction of the compound (Id).

Thus obtained reaction product is, if necessary, hydrolyzed. The hydrolysis sufficiently proceeds by pouring the reaction mixture to water or a mixture of water and a hydrophilic solvent such as methanol, ethanol, etc. In this hydrolysis, water may contain a base such as alkali metal bicarbonate, trialkylamine, etc. or an acid such as dilute hydrochloric acid, acetic acid, etc.

In the above reactions, the acylamino group $R^{1b}$ in the compound (Ie) is changed to the other acylamino group for $R^{1b'}$ in the compound (If) which is derived from the acylating agent.

The present invention may include the cases that the free carboxy group is changed into the protected carboxy group and the protected carboxy is changed into the other protected carboxy group or into the free carboxy group in these reactions and post-treating in these reactions.

The object compound (Ij) can be prepared by subjecting the compound (Ii) to elimination reaction of the protective group of hydroxy.

The present elimination reaction is carried out in accordance with a conventional method such as a method of using an acid or a base, reduction, and the like. These methods may be selected depending on kind of the protective groups to be eliminated. The elimination reaction with the acid is one of the most commonly applied methods for eliminating the protective groups such as benzyloxycarbonyl substituted benzyloxycarbonyl, alkoxycarbonyl, substituted alkoxycarbonyl, aralkoxycarbonyl, adamantyloxycarbonyl, trityl, substituted phenylthio, etc. Suitable acid may include, for example, formic acid, trifluoroacetic acid, benzenesulfonic acid, p-toluenesulfonic acid, and the like, and the most suitable acid is an acid which can be easily distilled off under reduced pressure, for example, formic acid, trifluoroacetic acid, etc. The acid suitable for the reaction can be selected according to the protected group to be eliminated and other factors. When the elimination reaction with the acid may be carried out in the presence of a solvent, such as a hydrophilic organic solvent, water or a mixed solvent thereof. The elimination reaction with the base is applied for eliminating acyl group.

Suitable base may include, for example, an inorganic base such as alkali metal (e.g., sodium, potassium, etc.), alkaline earth metal (e.g., magnesium, calcium, etc.), the hydroxide or carbonate or bicarbonate thereof, and the like, or an organic base such as trialkylamine (e.g., trimethylamine, triethylamine, etc.), picoline, N-methylpyrrolidine, N-methyl morpholine, 1,5-diazobicyclo[4,3,0]non-5-ene, 1,4-diazabicyclo[2,2,2]octane, 1,8-diazabicyclo[5,4,0]undecene-7, and the like. The elimination reaction with the base is often carried out in water or a hydrophilic organic solvent or a mixed solvent thereof.

The reduction is generally applied for eliminating, for example, trichloroethoxycarbonyl, benzyloxycarbonyl, substituted benzyloxycarbonyl, 2-pyridylmethoxycarbonyl, etc.

The reduction applicable for the elimination reaction of the present invention may include, for example, reduction using a metal (e.g., tin, zinc, iron, etc.) or a combination of metalic compound (e.g., chromous chloride, chromous acetate, etc.) and an organic or inorganic acid (e.g., acetic acid, propionic acid, hydrochloric acid, etc.), and reduction in the presence of a metallic catalyst for catalytic reduction. The metallic catalysts for catalytic reduction may include, for example, Raney-nickel, platinum oxide, palladium carbon and other conventional catalysts. The protective group, trifluoroacetyl can be usually eliminated by treating with water in the presence or absence of the base, and halogen substituted-alkoxycarbonyl and 8-quinolyloxycarbonyl are usually eliminated by treating with a heavy metal such as copper, zinc, etc.

When the protective group is trifluoroacetyl, it can be eliminated by treating with water or water in the presence of a base, and when the protective group is halogen substituted alkoxycarbonyl or 8-quinolyloxycarbonyl, those can be eliminated by treating with a heavy metal such as copper, lead, and the like.

When the protective group is acyl, the acyl can be eliminated by hydrolysis as mentioned above or by other conventional hydrolysis.

The reaction temperature is not limitative and may suitably selected in accordance with the protective group for hydroxy and the elimination method, and the present reaction is preferably carried out under a mild condition such as under cooling or slightly warming.

The present invention includes, within its scope, the case that the protected carboxy group is changed into the other protected carboxy group or into the free carboxy group during the reaction or post-treati treating in the present reaction.

The present invention also include, within its scope, the case that when the compound (Ii) possesses furthermore one or more protected amino, protected carboxy and/or, protected mercapto groups in the acylamino group at 7 position on cephem ring, said groups are changed into corresponding free groups during the reaction.

The object compound (Il) can be prepared by subjecting the compound (Ik) to elimination reaction of the protective group of the carboxy.

In the present elimination reaction, conventional methods used in the elimination reaction, conventional methods used in the elimination reaction of the protected carboxy, for example, reduction, hydrolysis, etc. can be applicable. When the protected group is an active ester, active amide or acid anhydride, those can be eliminated by hydrolysis, usually eliminated under mild hydrolysis conditions such as by contacting with water. The reduction can be applicable for eliminating, for example, 2-iodoethyl ester, 2,2,2-trichloroethyl ester, benzyl ester, etc. The elimination reaction with an acid can be applicable for eliminating the protected groups such as p-methoxybenzyl ester, tert-butyl ester, tert-pentyl ester, trityl ester, diphenylmethyl ester, bis(methoxyphenyl)methyl ester, 3,4-dimethoxybenzyl ester, 1-cyclopropylethyl ester, and the like. The elimination reaction with an anhydrous basic catalyst can be applicable for eliminating the protective groups such as ethynyl ester, 4-hydroxy-3,5-di(tert-butyl)benzyl ester, and the like. The reduction applicable for the elimination reaction of the present invention may include, for exam example, reduction using a combination of a metal (e.g., zinc, zinc amalgam, etc.) or a chrome salt compound (e.g., chromous chloride, chromous acetate, etc.) and an organic or inorganic acid (e.g., acetic acid, propionic acid, hydrochloric acid, etc.), and reduction in the presence of a metallic catalytic reduction. The metallic catalysts for catalytic reduction include, for example, platinum catalyst (e.g., platinum wire, spongy platinum, platinum black, platinum colloid, etc.), palladium catalyst (e.g., palladium spongy, palladium black, palladium oxide, palladium on barium sulfate, palladium on barium carbonate, palladium on charcoal, palladium on silica gel, palladium colloid, etc.), nickel catalyst (e.g., reduced nickel, nickel oxide, Raney nickel, Urushibara nickel, etc.), etc. Suitable acid used for the elimination reaction may include, for example, formic acid, trihaloacetic acid (e.g., trichloroacetic acid, trifluoroacetic acid, etc.), hydrochloric acid, hydrofluoric acid, p-toluenesulfonic acid, trifluoromethanesulfonic acid, mixed acid of hydrochloric acid and acetic acid, etc.), etc. Suitable anhydrous basic catalyst for the elimination reaction may include, for example, sodium thiophenolate, $(CH_3)_2LiCu$, etc. When the protective group is eliminated by treating with water or a liquid acid in the reaction, the present reaction can be carried out without solvent. In the present reaction, can be used any solvent which does not adversely influence the present reaction, for example, dimethylformamide, methylene chloride, chloroform, tetrahydrofuran, acetone, methanol, ethanol and the like. There is no particular limitation to the reaction temperature, and it may suitably selected according to the starting compound and an elimination method to be practically applied. The present invention includes the case that a protected carboxy, hydroxy, mercapto or amino group contained in the starting compound is changed into each free carboxy, hydroxy, mercapto or amino group, respectively, during the present reaction or post-treating in the present reaction. Thus obtained compound (Il) can be converted to a desirable metal (e.g., sodium, potassium, etc.) salt or an organic base salt thereof, if necessary.

The object compound (In) can be prepared by reacting the compound (Im) or a salt thereof with a lower alkanone of the general formula: $R^5—CO—R^6$ in which $R^5$ and $R^6$ are each lower alkyl.

Suitable salt of the compound (Im) may include organic acid salt (e.g., acetate, maleate, tartrate, benzenesulfonate, toluenesulfonate, etc.) and inorganic acid salt (e.g., hydrochloride, sulfate, phosphate, etc.), and the like.

Suitable lower alkanone of the general formula: $R^5$-CO-$R^6$ may include, for example, acetone, 2-butanone, 2-pentanone, 3-hexanone, etc.

The present reaction can be preferably carried out in the presence of an base, for example, an inorganic base such as alkali metal (e.g., lithium, sodium, potassium, etc.), and alkaline earth metal (e.g., magnesium, calcium, etc.), and the corresponding hydroxide, carbonate, bicarbonate, and the like; an organic base such as tertiary amine (e.g., trimethylamine, triethylamine, tripropylamine, triisopropylamine, tributylamine, dimethylbenzylamine, triphenethylamine, pyrrolidine, picoline, α-picoline, N-methylpiperidine, N-methylmorpholine, N,N'-dimethylpiperazine, 1,5-diazabicyclo[4,3,0]-non-5-ene, 1,4-diazabicyclo[2,2,2]octane, 1,8-diazabicyclo[5,4,0]undecene-7, etc.); quaternary ammoniumhydroxide compound, and the like.

The present reaction can be carried out with or without solvent.

Suitable solvent include any solvent which does not adversely influence the reaction, for example, dimethylformamide, dimethylsulfoxide, hexamethylphosphoramide, tetramethylurea, tetrahydrofuran, methylene chloride, dioxane, glyme, diglyme, acetonitrile, phosphate buffer, etc.

There is no particular limitation to the present reaction temperature, and the present reaction proceeds satisfactorily at room temperature or under cooling and may be hastened by heating.

The present invention may include the cases that the free carboxy group is changed into the protected carboxy group and the protected carboxy group is changed into other protected carboxy group or into the free carboxy group during the present reaction and post-treating in the present reaction.

The obtained compound (In) can be converted to a desirable acid salt, for example, an organic acid salt (e.g., acetate, maleate, tartrate, benzenesulfonate, toluenesulfonate, etc.) and an inorganic acid salt (e.g., hydrochloride, sulfate, phosphate, etc.).

The present invention may include situations wherein 2-cephem compounds, 3-cephem compounds and 3-cephem stereomers at the two position of the 3-cephem ring are sometimes interconvertible during the above mentioned reactions in alternative processes or in post treatment processes thereof.

When the object compound (I) has free carboxy group(s), it can be converted to a metal (e.g., sodium, potassium, magnesium, etc.) salt or an organic amine (e.g., methylamine, diethylamine, trimethylamine, triethylamine, aniline, pyridine, picoline, N,N'-dibenzylethylenediamine, etc.) salt by a conventional method, and when the object compound (I) has free amino group(s), it can be converted to an organic acid salt (e.g., hydrochloride, sulfate, etc.) or an organic acid salt (e.g., acetate, maleate, tartrate, etc.) by a conventional method.

The object compounds (I) of this invention have antimicrobial activities against various pathogenic microorganisms and may be useful for treatment of diseases infected by such microorganisms in human and animals.

With regard to representative object compounds of this invention, antimicrobial activities are illustrated for reference in the following. The MIC values (mcg/ml) against Staphylococcus aureus 209-P JC-1 and Bacillus subtilis ATCC-6633 of the object compounds (I) are shown below.

Method for estimation of antimicrobial activity in vitro:

In vitro antimicrobial activity was determined by the two-fold agar-plate dilution method as described below. One loopful of an overnight culture of each test strain in Trypticase-soy broth ($10^8$ viable cells per ml) was streaked on heart infusion agar (HIagar) containing graded concentration of antibiotics, and the minimum inhibitory concentration (MIC) was expressed in terms of mcg/ml after incubation at 37° C. for 20 hours.

(1) 2-Methyl-7-[N-[2-(1,3,4-thiadiazol-2-ylthio)acetyl]-phenylglycyl]amino-3-cephem-4-carboxylic acid S. aureus: 1.56; B. subtilis: 3.13

(2) 2-Methyl-7-[2-hydroxy-2-(2-thienyl)acetamido]-3-cephem-4-carboxylic acid

S. aureus: 0.78; B. subtilis: 0.78

(3) 2-Methyl-7-[2-(5-indanyloxy)carbonyl-2-phenyl-acetamido]-3-cephem-4-carboxylic acid S. aureaus: 1.56; B. subtilis: 6.25

(4) 2-Methyl-7-(2-isonicotinoyloxy-2-phenylacetamido)-3-cephem-4-carboxylic acid S. aureaus: 0.39; B. subtilis: 0.78

(5) 2-Methyl-7-[2-(2-thienyl)acetamido]-3-cephem-4-carboxylic acid

S. aureaus: 0.78; B. subtilis: 0.39

(6) 2-Methyl-7-[2-(3-chlorophenyl)acetamido]-3-cephem-4-carboxylic acid

S. aureaus: 0.1; B. subtilis: 0.2

(7) 2-Methyl-7-(2-hydroxy-2-phenylacetamido)-3-cephem-4-carboxylic acid

S. aureaus: 0.78; B. subtilis: 0.39

(8) 2-Methyl-7-(2-phenylacetamido)-3-cephem-4-carboxylic acid

S. aureaus: 0.78; B. subtilis: 0.2

(9) 2-Methyl-7-(2-phenylthioacetamido)-3-cephem-4-carboxylic acid

S. aureaus: 0.2; B. subtilis: 0.2

(10) 2-Methyl-7-(2-azido-2-phenylacetamido)-3-cephem-4-carboxylic acid

S. aureaus: 1.56; B. subtilis: 0.39

(11) 2-Methyl-7-[2-(1,3,4-thiadiazol-2-ylthio)acetamido]-3-cephem-4-carboxylic acid S. aureaus: 1.56; B. subtilis: 0.78

(12) 2-Methyl-7-[2-(1,2,5-thiadiazol-3-yl)acetamido]-3-cephem-4-carboxylic acid

S. aureaus: 3.13; B. subtilis: 1.56

(13) 2-Methyl-7-(2-cyanoacetamido)-3-cephem-4-carboxylic acid

S. aureaus: 3.13; B. subtilis: 3.13

(14) 2-Methyl-7-[2-(allylthio)acetamido]-3-cephem-4-carboxylic acid

S. aureaus: 1.56; B. subtilis: 1.56

(15) 2-Methyl-7-[2-(3-pyridyl)acetamido]-3-cephem-4-carboxylic acid

S. aureaus: 3.13; B. subtilis: 0.78

(16) 2-Methyl-7-[2-amino-2-(4-methylthio phenyl)acetamido]-3-cephem-4-carboxylic acid S. aureaus: 3.13; B. subtilis: 6.25

The object compound (I) of the present invention may be formulated for administration in any convenient way by analogy with other antibiotic substances.

Thus, the composition comprising the compounds (I) can be used in the form of pharmaceutical preparations, for example, in solid, semisolid or liquid form, which contain the active object compound (I) in admixture with a pharmaceutical or inorganic carrier or excipient suitable for external or parenteral applications. The active ingredient may be compounded, for example, with the usual carriers for tablets, pellets, capsules, suppositories, solutions, emulsions, aqueous suspensions and other form suitable for use. The carriers which can be used are glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid or liquid form, and in addition auxiliary, stabilizing, thickening and coloring agents can be contained in the compositions of this invention. The compositions of this invention can also contain preservative or bacteriostatic agents thereby keeping the active ingredient in the desired preparations stable in activity. The active object compound (I) is included in the compositions of this invention in an amount sufficient to produce the desired therapeutic effect upon the bacterially infected process or condition. While the dosage or therapeutically effective quantity of the compound varies from and also depends upon the age and condition of each individual patient being treated, a daily dose of about 0.5–5 g., preferably 1–2 g/day of the active ingredient is generally given for treating diseases against which the object compound (I) is useful.

Having now generally described in the invention, a further understanding can be attained by reference to certain specific examples which are provided herein for purposes of illustration only and are not intended to be construed as limiting unless otherwise so indicated.

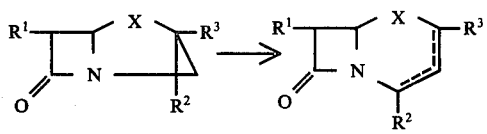

EXAMPLE 1

A solution of aluminum bromide (3.4 g.) in dried dichloromethane (20 ml.) was dropwise added at −10° C. over about 10 minutes to a solution of 2,2,2-trichloroethyl 2-methyl-2,3-methylene-6-(2-phenylacetamido)penam-3-carboxylate (4.6 g.) in dried dichloromethane (30 ml.). After addition, the reaction mixture was stirred for 4.5 hours at room temperature, washed in turn with 2% hydrochloric acid (30 ml.) three times, a saturated sodium bicarbonate aqueous solution and a saturated sodium chloride aqueous solution. After drying over magnesium sulfate, the solvent was distilled off and the residue was washed with ether and collected by filtration to give 2,2,2-trichloroethyl 2-methyl-7-(2-phenylacetamido)-3cephem-4-carboxylate (3.3 g.). This compound was recrystallized from ethanol to give crystals, mp 175° to 178° C.

EXAMPLE 2

A solution of aluminum bromide (0.4 g.) in dried dichloromethane (5 ml.) was dropwise added under ice-cooling to a suspension of 2,2,2-trichloroethyl 2-methyl-2,3-methylene-6-{2-(1H-tetrazol-1-yl)acetamido}penam-3-carboxylate (0.46 g.) in dried dichloromethane (10 ml.). After stirring for 4 hours at room temperature, the reaction mixture was washed in turn with 2% hydrochloric acid three times, a saturated sodium bicarbonate aqueous solution and a saturated sodium chloride aqueous solution and then dried over magnesium sulfate. After drying, the solvent was distilled off and the residue was crystallized from ethanol to give 2,2,2-trichloroethyl 2-methyl-7-{2-(1H-tetrazol-1-yl)acetamido}-3-cephem-4-carboxylate (0.24 g.), mp 168° to 170° C.

EXAMPLE 3

Titanium tetrachloride (0.19 g.) was added to a solution of 2,2,2-trichloroethyl 2-methyl-2,3-methylene-6-(2-phenylacetamido)penam-3-carboxylate (0.46 g.) in dried dichloromethane (5 ml.) and the mixture was stirred for 2.5 hours. After the reaction, the reaction mixture was washed in turn with 2% hydrochloric acid three times, a saturated sodium bicarbonate aqueous solution and a saturated sodium chloride aqueous solution and then dried over magnesium sulfate. After the solvent was distilled off the residue (0.43 g.) was purified by column chromatography on silica gel (10 g.) using chloroform as developing solvent to give 2,2,2-trichloroethyl 2-methyl-7-(2-phenylacetamido)-2-cephem-4-carboxylate (0.1 g.), mp 136° to 137° C.

EXAMPLE 4

Aluminum chloride (2.66 g.) was added under ice-cooling to a solution of 2,2,2-trichloroethyl 2-methyl-2,3-methylene-6-(2-phenylacetamido)penam-3-carboxylate (9.2 g.) in dried dichloromethane (100 ml.) and the mixture was stirred for 7 hours at room temperature. After the reaction, the reaction mixture was washed in turn with 2% hydrochloric acid three times, a saturated sodium bicarbonate aqueous solution and a saturated sodium chloride aqueous solution and then dried over magnesium sulfate. After drying, the solvent was distilled off and the residue was purified by column chromatography on silica gel (200 g.) using chloroform as developing solvent to give 2,2,2-trichloroethyl 2-methyl-7-(2-phenylacetamido)-3-cephem-4-carboxylate (2.4 g.), mp 175° to 178° C.

EXAMPLE 5

A solution of 2,2,2-trichloroethyl 2-methyl-2,3-methylene-6-(benzyloxycarboxamido)penam-3-carboxylate (0.58 g.) in dried dichloromethane (10 ml.) was dropwise added at −15° to −12° C. to a solution of aluminum bromide (0.5 g.) in dried dichloromethane (10 ml.), and the mixture was stirred for 20 minutes at the same temperature and then for 1.5 hours at room temperature. After the reaction, the reaction mixture was washed in turn with 5% hydrochloric acid, water, 5% sodium bicarbonate aqueous solution and water, dried and the solvent was distilled off to give oily substance. The oily substance was dissolved in ethanol, allowed to stand, after which precipitated crystals were collected by filtration and dried to give 2,2,2-trichloroethyl 2-methyl-7-benzyloxycarboxamido-3-cephem-4-carboxylate, mp 143° to 144° C.

EXAMPLE 6

A solution of 2,2,2-trichloroethyl 2-methyl-2,3-methylene-6-{2-(3-chlorophenyl)acetamido}penam-3-carboxylate (3.4 g.) in dried dichloromethane (50 ml.) was dropwise added at −15° C. to a solution of aluminum bromide (2.8 g.) in dried dichloromethane (20 ml.) and the mixture was stirred for 3 hours at room temperature. After the reaction, the reaction mixture was washed in turn with 5% hydrochloric acid, water, 5% sodium bicarbonate aqueous solution and water and then dried. After the solvent was distilled off, the residue was crystallized from ether to give 2,2,2-trichloroethyl 2-methyl-7-{2-(3-chlorophenyl)acetamido}3-cephem-4-carboxylate (2.9 g.), mp 144° to 145.5° C. (dec.).

EXAMPLE 7

A solution of 2,2,2-trichloroethyl 2-methyl-2,3-methylene-6-{2-(2-thienyl)acetamido}penam-3-carboxylate (1.74 g.) in dried dichloromethane (20 ml.) was dropwise added at −15° C. to a solution of aluminum bromide (2.14 g.) in dried dichloromethane (10 ml.) and the mixture was stirred for 4 hours at room temperature. After the reaction, the reaction mixture was washed in turn with 5% hydrochloric acid, water, 5% sodium bicarbonate aqueous solution and water and then dried. After the solvent was distilled off, the residue (powder) was recrystallized from ethanol to give 2,2,2-trichloroethyl 2-methyl-7-{2-(2-thienyl)acetamido}-3-cephem-4-carboxylate (1.46 g.), mp 161° to 162° C. (dec.).

EXAMPLE 8

A solution of 2,2,2-trichloroethyl 2-methyl-2,3-methylene-6-{2-(1,2,5-thiadiazol-3-yl)acetamido}-penam-3-carboxylate (16.5 g.) in dried dichloromethane (100 ml.) was gradually dropwise added to a solution of aluminum bromide (17.5 g.) in dichloromethane (100 ml.) at below −10° C. Then, the mixture was stirred for 2 hours at below 0° C. and stirred for further 2 hours at room temperature. After the reaction, the reaction mixture was washed in turn with 2% hydrochloric acid (100 ml.) twice, a saturated sodium bicarbonate aqueous solution and a saturated sodium chloride aqueous solution and then dried over magnesium sulfate. After drying, the solvent was distilled off to give powdery 2,2,2-trichloroethyl 2-methyl-7-{2-(1,2,5-thiadiazol-3-yl)acetamido}-3-cephem-4-carboxylate (13.2 g.), mp 180° to 185° C. (dec.).

EXAMPLE 9

A solution of methyl 2-methyl-2,3-methylene-6-(2-phenoxyacetamido)-penam-3-carboxylate (2.1 g.) in dried dichloromethane (11 ml.) was dropwise added over 8 minutes at −10° C. to a solution of aluminum bromide (2.32 g.) in dried dichloromethane (23 ml.) and the reaction temperature was gradually elevated to room temperature, after which the mixture was stirred for 4.4 hours at room temperature. After the reaction, the reaction mixture was poured into ice-water (150 ml.) and the dichloromethane layer was separated, after which the aqueous layer was once extracted with chloroform. The combined dichloromethane and chloroform extract was washed in turn with water, 2% hydrochloric acid, water, a dilute sodium bicarbonate aqueous solution and water, and then dried over magnesium sulfate. After the solvent was distilled off, the obtained yellow oil was purified by column chromatography on silica gel (15 g.) using chloroform as developing solvent to give orange oil of methyl 2-methyl-7-(2-phenoxyacetamido)-3-cephem-4-carboxylate (0.7 g.).

Infrared Absorption Spectrum (chloroform) 3400, 1785, 1726, 1689 cm$^{-1}$

EXAMPLE 10

A solution of 2,2,2-trichloroethyl 2-methyl-2,3-methylene-6-(2-phenoxyacetamido)penam-3-carboxylate (1.39 g.) in dried dichloromethane (7 ml.) was dropwise added over 10 minutes at −10° C. to a solution of aluminum bromide (1.16 g.) in dried dichloromethane (12 ml.), and the reaction temperature was gradually elevated to room temperature, after which the mixture was stirred for 4 hours at room temperature. After the reaction, the reaction mixture was poured into ice-water (70 ml.) and the dichloromethane layer was separated, after which the aqueous layer was once extracted with chloroform. The combined dichloromethane and chloroform layer was washed in turn with water, 2% hydrochloric acid, water, a dilute sodium bicarbonate aqueous solution and water, and then dried over magnesium sulfate. After the solvent was distilled off, the obtained pale brown oil (1.2 g.) was crystallized by adding ether and a small amount of isopropyl ether. The crystals were collected by filtration, followed by washing with isopropyl ether and recrystallized from a mixture of benzene: isopropyl ether (1:3) to give colorless granules of 2,2,2-trichloroethyl 2-methyl-7-(2-phenoxyacetamido)-3-cephem-4-carboxylate (0.9 g.), mp 118° to 120° C.

EXAMPLE 11

A solution of 2,2,2-trichloroethyl 2-methyl-2,3-methylene-6-(2-phenylacetamido)penam-3-carboxylate (0.92 g.) in dried dichloromethane (5 ml.) was dropwise added at −10° C. over about 5 minutes to a solution of aluminum bromide (0.8 g.) in dried dichloromethane (10 ml.) and the mixture was stirred for 2 hours at room temperature. After the reaction was completed, the reaction mixture was washed in turn with 2% hydrochloric acid, a sodium bicarbonate aqueous solution and a saturated sodium chloride aqueous solution and then dried over magnesium sulfate, after which the solvent was distilled off under reduced pressure. The residual crystals were washed with ether and dried to give 2,2,2-trichloroethyl 2-methyl-7-(2-phenylacetamido)3-cephem-4-carboxylate (0.74 g.), mp 175° to 178° C. And the residue obtained by concentrating the ether washing was purified by column chromatography on silica gel to give 2,2,2-trichloroethyl 2-methyl-7-(2-phenylacetamido)-3-cephem-4-carboxylate (0.05 g.), mp 118° to 120° C., which is a stereoisomer at 2 position of the above obtained 2,2,2-trichloroethyl 2-methyl-7-(2-phenylacetamido)-3-cephem-4-carboxylate, mp 175° to 178° C., and 2,2,2-trichloroethyl 2-methyl-7-(2-phenylacetamido)-2-cephem-4-carboxylate (0.05 g.), mp 136° to 137° C. The above obtained 2,2,2-trichloroethyl 2-methyl-7-(2-phenylacetamido)-3-cephem-4-carboxylate, mp 118° to 120° C., was recrystallized from benzene to give crystals, mp 120° to 123° C.

EXAMPLE 12

A solution of aluminum bromide (1.7 g.) in carbon disulfide (40 ml.) was dropwise added under stirring at room temperature to a suspension of 2-methyl-2,3-methylene-6-(2-phenylacetamido)penam-3-carboxylic acid (0.66 g.) in carbon disulfide (70 ml.) and the mixture was stirred for 20 hours at the same temperature. After the reaction was completed, the reaction mixture was poured into 5% hydrochloric acid (200 ml.) and the hydrochloric acid layer was separated and then extracted with ethyl acetate. The extract was washed with water and dried, after which the solvent was distilled off. The residue was recrystallized from acetonitrile to give 2-methyl-7-(2-phenylacetamido)-3-cephem-4-carboxylic acid (0.33 g.), mp 109° C. (dec.).

The following compounds were obtained by using a similar manner as those of the Examples 1 to 12.
(1) 2-Methyl-7-{N-(1-cyclopropylethoxy)-carbonyl-phenylglycyl}amino-3-cephem-4-carboxylic acid, mp 168° to 169° C.
(2) 2-Methyl-7-{2-(1H-tetrazol-1-yl)acetamido}-3-cephem-4-carboxylic acid, mp 202° to 203° C. (dec.).
(3) 2-Methyl-7-{2-(2-thienyl)acetamido}-3-cephem-4-carboxylic acid, mp 175° C. (dec.).
(4) 2-Methyl-7-benzyloxycarboxamido-3-cephem-4-carboxylic acid, mp 167° to 169° C. (dec.).
(5) 2-Methyl-7-(2-phenylthioacetamido)-3-cephem-4-carboxylic acid, mp 168° to 171° C. (dec.).
(6) 2-Methyl-7-{2-(3-chlorophenyl)acetamido}-3-cephem-4-carboxylic acid, mp 173° to 174° C. (dec.).
(7) 2-Methyl-7-{3-(N-tert.-butoxycarbonylamino)-3-(2-thienyl)propionamido}-3-cephem-4-carboxylic acid, mp 167° to 170° C. (dec.).
(8) 2-Methyl-7-(2-cyanoacetamido)-3-cephem-4-carboxylic acid, mp 162° to 166° C.
(9) 2-Methyl-7-(3-phenylureido)-3-cephem-4-carboxylic acid, mp 148° to 151° C.
(10) 2-Methyl-7-{2-(1,3,4-thiadiazol-2-ylthio)acetamido}-3-cephem-4-carboxylic acid, mp 197° to 199° C.
(11) 2-Methyl-7-{N-tert.-butoxycarbonyl-2-(2-thienyl)-glycyl}amino-3-cephem-4-carboxylic acid, powder.
(12) 2-Methyl-7-{2-(5-methyl-1,3,4-thiadiazol-2-yloxy)acetamido}-3-cephem-4-carboxylic acid, mp 113° to 116° C.
(13) 2-Methyl-7-{3-(2-chlorophenyl)-5-methylisoxazol-4-yl}carboxamido-3-cephem-4-carboxylic acid, mp 202° to 203° C.
(14) 2-Methyl-7-(2-methylthioacetamido)-3-cephem-4-carboxylic acid, mp 181° to 183° C. (dec.).
(15) 2-Methyl-7-(2-allylthioacetamido)-3-cephem-4carboxylic acid, mp 121° to 123° C.
(16) 2-Methyl-7-(2-formyloxy-2-phenylacetamido)3-cephem-4-carboxylic acid, powder.
(17) 2-Methyl-7-(1-cyclopropylethoxy)carboxamido-3-cephem-4-carboxylic acid, mp 158.5° to 160° C. (dec.).
(18) 2,2,2-Trichloroethyl 2-methyl-7-{N-(1-cyclopropylethoxy)carbonylphenylglycyl}amino-3-cephem-4carboxylate, mp 165° to 167.5° C.
(19) 2,2,2-Trichloroethyl 2-methyl-7-(2-phenylthioacetamido)-3-cephem-4-carboxylate, mp 140° to 142° C.
(20) 2,2,2-Trichloroethyl 2-methyl-7-{3-(N-tert.-butoxycarbonylamino)-3-(2-thienyl)propionamido}-3-cephem-4-carboxylate, mp 188° to 192° C.
(21) 2,2,2-Trichloroethyl 2-methyl-7-(2-cyanoacetamido)-3-cephem-4-carboxylate, mp 160° to 165° C. (dec.).
(22) 2,2,2-Trichloroethyl 2-methyl-7-(3-phenylureido)-3-cephem-4-carboxylate, mp 172° to 174° C.
(23) 2,2,2-Trichloroethyl 2-methyl-7-{2-(1,3,4-thiadiazol-2-ylthio)acetamido}-3-cephem-4-carboxylate, mp 130° to 140° C. (dec.).
(24) 2,2,2-Trichloroethyl 2-methyl-7-{N-tert.-butoxycarbonyl-2-(2-thienyl)glycyl}amino-3-cephem-4-carboxylate, powder.
(25) 2,2,2-Trichloroethyl 2-methyl-7-{2-(5-methyl-1,3,4-thiadiazol-2-yloxy)acetamido}-3-cephem-4-carboxylate, amorphous.
(26) 2,2,2-Trichloroethyl 2-methyl-7-{3-(2-chlorophenyl)-5-methylisoxazol-4-yl}carboxamido-3-cephem-4-carboxylate, amorphous.
(27) 2,2,2-Trichloroethyl 2-methyl-7-(2-methylthioacetamido)-3-cephem-4-carboxylate, mp 151° to 153° C.
(28) 2,2,2-Trichloroethyl 2-methyl-7-(2-allylthioacetamido)-3-cephem-4-carboxylate, mp 96° C.
(29) 2,2,2-Trichloroethyl 2-methyl-7-(2-formyloxy-2-phenylacetamido)-3-cephem-4-carboxylate, powder.
(30) 2,2,2-Trichloroethyl 2-methyl-7-(1-cyclopropylethoxy)carboxamido-3-cephem-4-carboxylate, colorless powder.
(31) 2,2,2-Trichloroethyl 2-methyl-7-{N-tert.-butoxycarbonyl-2-(4-hydroxyphenyl)-D-glycyl}amino-3-cephem-4-carboxylate, mp 130° to 135° C. (dec.).

(32) 2,2,2-Trichloroethyl 2-methyl-7-{N-tert.-butoxycarbonyl-2-(4-methylthiophenyl)glycyl}amino-3-cephem-4-carboxylate, mp 115° to 120° C.

(33) 2,2,2-Trichloroethyl 2-methyl-7-{N-tert.-butoxycarbonyl-2-(4-methoxyphenyl)glycyl}amino-3-cephem-4-carboxylate, mp 92° to 95° C. (dec.).

(34) 2,2,2-Trichloroethyl 2-methyl-7-{N-tert.-butoxycarbonyl-2-(2,5-dihydrophenyl)glycyl}amino-3-cephem-4-carboxylate, mp 104° to 111° C. (dec.).

(35) 2,2,2-Trichloroethyl 2-methyl-7-(2-sulfo-2-phenylacetamido)-3-cephem-4-carboxylate, mp 150° C. (dec.).

(36) 2,2,2-Trichloroethyl 2-methyl-7-{N-(1-cyclopropylethoxy)carbonyl-2-(5,6-dihydro-2H-pyran-3-yl)glycyl}amino-3-cephem-4-carboxylate, mp 118° to 120° C. (dec.).

(37) 2,2,2-Trichloroethyl 2-methyl-7-{N-tert.-butoxycarbonyl-2-(4-tert.-butoxycarbonylmethoxyphenyl)glycyl}amino-3-cephem-4-carboxylate, powder.

(38) 2,2,2-Trichloroethyl 2-methyl-7-{N-(1,3,4-thiadiazol-2-yl)thiomethylcarbonyl-2-phenylglycyl}·amino-3-cephem-4-carboxylate, mp 148° to 150° C. (dec.).

(39) 2,2,2-Trichloroethyl 2-methyl-7-{N-tert.-butoxycarbonyl-2-(4-methylsulfinylphenyl)glycyl}amino-3-cephem-4-carboxylate, mp 115° to 125° C.

(40) 2,2,2-Trichloroethyl 2-methyl-7-(2-isonicotinoyloxy-2-phenylacetamido)-3-cephem-4-carboxylate, mp 100° to 115° C. (dec.).

(41) 2,2,2-Trichloroethyl 2-methyl-7-{2-(5-indanyl)oxycarbonyl-2-phenylacetamido}-3-cephem-4-carboxylate, mp 165° to 170° C.

(42) 2-Methyl-7-{D-2-(4-hydroxyphenyl)glycyl}amino-3-cephem-4-carboxylic acid, powder.

(43) 2-Methyl-7-{2-(5,6-dihydro-2H-Pyran-3-yl)glycyl}-amino-3-cephem-4-carboxylic acid, mp 125° to 128° C. (dec.)

(44) 2-Methyl-7-{2-(3-methanesulfonamidophenyl)-glycyl}-amino-3-cephem-4-carboxylic acid, mp 192° to 193° C. (dec.).

(45) 2-Methyl-7-{2-(4-carboxymethoxyphenyl)glycyl}-amino-3-cephem-4-carboxylic acid, powder.

(46) 2-Methyl-7-{2-(4-methylthiophenyl)glycyl}amino-3-cephem-4-carboxylic acid, mp 165° to 175° C.

(47) 2-Methyl-7-{2-(4-methoxyphenyl)glycyl}amino-3-cephem-4-carboxylic acid, mp 165° to 168° C.

(48) 2-Methyl-7-{2-(2,5-dihydrophenyl)glycyl}amino-3-cephem-4-carboxylic acid, mp 168° C. (dec.)

(49) 2-Methyl-7-{2-(4-methylsulfinylphenyl)glycyl}·amino-3-cephem-4-carboxylic acid, powder.

(50) 2,2,2-Trichloroethyl 2-methyl-7-{2-(5,6-dihydro-2H-pyran-3-yl)acetamido}-3-cephem-4-carboxylate, mp 149.5° to 150.5° C.

(51) 2-Methyl-7-{2-(5,6-dihydro-2H-pyran-3-yl)acetamido}-3-cephem-4-carboxylic acid, mp 172.5° to 173.5° C. (dec.).

(52) 2,2,2-Trichloroethyl 2-methyl-7-{N-tert.-butoxycarbonyl-2-(3-methanesulfonamidophenyl)glycyl}-amino-3-cephem-4-carboxylate, amorphous.

(53) 2-Methyl-7-{N-tert.-butoxycarbonyl-2-(3-methanesulfonamidophenyl)glycyl}amino-3-cephem-4-carboxylic acid, oil.

(54) 2-Methyl-7-(4-methoxyphenyl)glyoxylamido-3-cephem-4-carboxylic acid, mp 188° to 189° C. (dec.).

(55) 2-Methyl-7-(N-tert.-butoxycarbonylphenyl-D-glycyl)-amino-3-cephem-4-carboxylic acid, mp 125° to 127° C. (dec.).

(56) 2-Methyl-7-[N-{2-(2-nitrophenoxy)acetyl}phenylglycyl]-amino-3-cephem-4-carboxylic acid, mp 135° to 137° C. (dec.).

(57) 2,2,2-Trichloroethyl 2-methyl-7-(N-tert.-butoxycarbonylphenyl-D-glycyl)amino-3-cephem-4-carboxylate, mp 115° to 116° C. (dec.).

(58) 2-Methyl-7-[2-(2-aminothiazol-4-yl)acetamido]-3-cephem-4-carboxylic acid, which can be represented as 2-methyl-7-[2-(2-imino-2,3-dihydrothiazol-4-yl)acetamido]-3-cephem-4-carboxylic acid, mp 250° to 255° C. (dec.).

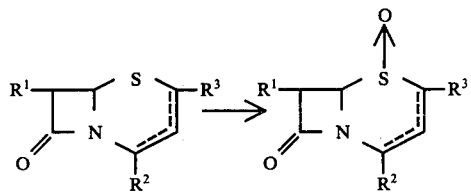

EXAMPLE 13

A solution of 3-chloroperbenzoic acid (0.44 g.) in chloroform (5 ml.) was dropwise added under ice-cooling to a solution of 2,2,2-trichloroethyl 2-methyl-7-(2-phenylacetamido)-3-cephem-4-carboxylate (0.92 g.) in chloroform (10 ml.) and the mixture was stirred for 1.5 hours at the same temperature. After the reaction, the precipitating crystals were filtered off and the filtrate was washed in turn with a sodium bicarbonate aqueous solution and a saturated sodium chloride aqueous solution, followed by drying over magnesium sulfate, and then the solvent was distilled off. The residue was crystallized using a small amount of ether to give 2,2,2-trichloroethyl 2-methyl-7-(2-phenylacetamido)-3-cephem-4-carboxylate-1-oxide, mp 173° to 175° C.

EXAMPLE 14

A solution of 3-chloroperbenzoic acid (0.40 g.) in dichloromethane (10 ml.) was dropwise added to a solution of 2,2,2-trichloroethyl 2-methyl-7-(2-phenylacetamido)-2-cephem-4-carboxylate (0.92 g.) in dichloromethane (10 ml.) and the mixture was stirred for 1 hour. After the reaction was completed, the reaction mixture was filtered and the filtrate was washed in turn with a sodium bicarbonate aqueous solution and a saturated sodium chloride aqueous solution, dried over magnesium sulfate, after which the solvent was distilled off under reduced pressure. The residue was recrystallized from ethanol to give 2,2,2-trichloroethyl 2-methyl-7-(2-phenylacetamido)-3-cephem-4-carboxylate-1-oxide (0.56 g.), mp 173° to 175° C.

And the above recrystallization mother liquid was concentrated and the residue was crystallized using ether to give 2,2,2-trichloroethyl 2-methyl-7-(2-phenylacetamido)-3-cephem-4-carboxylate-1-oxide (0.34 g.), mp 160° C., which is a stereoisomer at 2 position of the above obtained 2,2,2-trichloroethyl 2-methyl-7-(2-phenylacetamido)-3-cephem-4-carboxylate-1-oxide, mp 173° to 175° C.

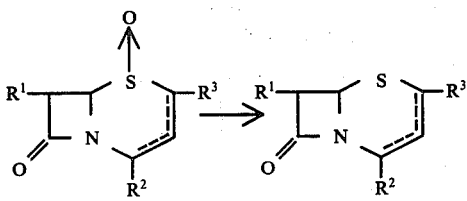

EXAMPLE 15

Phosphorus trichloride (0.5 ml.) was dropwise added under ice-cooling to a solution of 2,2,2-trichloroethyl 2-methyl-7-(2-phenylacetamido)-3-cephem-4-carboxylate-1-oxide (0.72 g.) in dimethylformamide (5 ml.) and the mixture was stirred for 1 hour at the same temperature. After the reaction, the reaction mixture was poured into a mixture of ethyl acetate (40 ml.) and ice-water (40 ml.), and the ethyl acetate layer was separated. The aqueous layer was further extracted with ethyl acetate (10 ml.), and the ethyl acetate layer was combined. The combined solution was washed in turn with 5% hydrochloric acid, a sodium bicarbonate aqueous solution and a saturated sodium chloride aqueous solution, and dried over magnesium sulfate. The dried solution was treated with activated charcoal and the solvent was distilled off. The residue was crystallized with a small amount of ether to give 2,2,2-trichloroethyl 2-methyl-7-(2-phenylacetamido)-3-cephem-4-carboxylate (0.43 g.), mp 175° to 178° C.

The following compounds were obtained by using the similar procedure as that of the Example 15.

(1) 2,2,2-Trichloroethyl 2-methyl-7-{2-(1H-tetrazol-1-yl)acetamido}-3-cephem-4-carboxylate, mp 168° to 170° C.

(2) 2,2,2-Trichloroethyl 2-methyl-7-benzyloxycarboxamido-3-cephem-4-carboxylate, mp 143° to 144° C.

(3) 2,2,2-Trichloroethyl 2-methyl-7-{2-(3-chlorophenyl)acetamido}-3-cephem-4-carboxylate, mp 144° to 145.5° C. (dec.).

(4) 2,2,2-Trichloroethyl 2-methyl-7-{2-(2-thienyl)acetamido}-3-cephem-4-carboxylate, mp 161° to 162° C. (dec.).

(5) 2,2,2-Trichloroethyl 2-methyl-7-{2-(1,2,5-thiadiazol-3-yl)acetamido}-3-cephem-4-carboxylate, mp 180° to 185° C. (dec.).

(6) Methyl 2-methyl-7-(2-phenoxyacetamido)-3-cephem-4-carboxylate, oil.

(7) 2,2,2-Trichloroethyl 2-methyl-7-(2-phenoxyacetamido)-3-cephem-4-carboxylate, mp 118 to 120° C.

(8) 2-Methyl-7-{N-(1-cyclopropylethoxy)carbonylphenylglycyl}-amino-3-cephem-4-carboxylic acid, mp 168° to 169° C.

(9) 2-Methyl-7-{2-(1H-tetrazol-1-yl)-acetamido}-3-cephem-4-carboxylic acid, mp 202 to 203° C. (dec.).

(10) 2-Methyl-7-{2-(2-thienyl)acetamido}-3-cephem-4-carboxylic acid, mp 175° C. (dec.).

(11) 2-Methyl-7-benzyloxycarboxamido-3-cephem-4-carboxylic acid, mp 167° to 169° C. (dec.).

(12) 2-Methyl-7-(2-phenylthioacetamido)-3-cephem-4-carboxylic acid, mp 168° to 171° C. (dec.).

(13) 2-Methyl-7-{2-(3-chlorophenyl)acetamido}-3-cephem-4-carboxylic acid, mp 173° to 174° C. (dec.).

(14) 2-Methyl-7-{3-(N-tert.-butoxycarbonylamino)-3-(2-thienyl)propionamido}-3-cephem-4-carboxylic acid, mp 167° to 170° C. (dec.).

(15) 2-Methyl-7-(2-cyanoacetamido)-3-cephem-4-carboxylic acid, mp 162° to 166° C.

(16) 2-Methyl-7-(3-phenylureido)-3-cephem-4-carboxylic acid, mp 148° to 151° C.

(17) 2-Methyl-7-{2-(1,3,4-thiadiazol-2-ylthio)acetamido}-3-cephem-4-carboxylic acid, mp 197° to 199° C.

(18) 2-Methyl-7-(N-tert.-butoxycarbonyl-2-thienylglycyl)amino-3-cephem-4-carboxylic acid, powder.

(19) 2-Methyl-7-{2-(5-methyl-1,3,4-thiadiazol-2-yloxy)acetamido}-3-cephem-4-carboxylic acid, mp 113° to 116° C.

(20) 2-Methyl-7-{3-(2-chlorophenyl)-5-methylisoxazol-4-yl}carboxamido-3-cephem-4-carboxylic acid, mp 202° to 203° C.

(21) 2-Methyl-7-(2-methylthioacetamido)-3-cephem-4-carboxylic acid, mp 181° to 183° C. (dec.).

(22) 2-Methyl-7-(2-allylthioacetamido)-3-cephem-4-carboxylic acid, mp 121° to 123° C.

(23) 2-Methyl-7-(2-formyloxy-2-phenylacetamido)-3-cephem-4-carboxylic acid, powder.

(24) 2-Methyl-7-(1-cyclopropylethoxy)carboxamido-3-cephem-4-carboxylic acid, mp 158.5° to 160° C. (dec.).

(25) 2,2,2-Trichloroethyl 2-methyl-7-{N-(1-cyclopropylethoxy)carbonylphenylglycyl}amino-3-cephem-4-carboxylate, mp 165° to 167.5° C.

(26) 2,2,2-Trichloroethyl 2-methyl-7-(2-phenylthioacetamido)-3-cephem-4-carboxylate, mp 140° to 142° C.

(27) 2,2,2-Trichloroethyl 2-methyl-7-{3-(N-tert.-butoxycarbonylamino)-3-(2-thienyl)propionamido}-3-cephem-4-carboxylate, mp 188° to 192° C.

(28) 2,2,2-Trichloroethyl 2-methyl-7-(2-cyanoacetamido)-3-cephem-4-carboxylate, mp 160° to 165° C. (dec.).

(29) 2,2,2-Trichloroethyl 2-methyl-7-(3-phenylureido)-3-cephem-4-carboxylate, mp 172° to 174° C.

(30) 2,2,2-Trichloroethyl 2-methyl-7-{2-(1,3,4-thiadiazol-2-ylthio)acetamido}-3-cephem-4-carboxylate, mp 130° to 140° C. (dec.).

(31) 2,2,2-Trichloroethyl 2-methyl-7-(N-tert.-butoxycarbonyl-2-thienylglycyl)amino-3-cephem-4-carboxylate, powder.

(32) 2,2,2-Trichloroethyl 2-methyl-7-{2-(5-methyl-1,3,4-thiadiazol-2-yloxy)acetamido}-3-cephem-4-carboxylate, amorphous.

(33) 2,2,2-Trichloroethyl 2-methyl-7-{3-(2-chlorophenyl)-5-methylisoxazol-4-yl}carboxamido-3-cephem-4-carboxylate, amorphous.

(34) 2,2,2-Trichloroethyl 2-methyl-7-(2-methylthioacetamido)-3-cephem-4-carboxylate, mp 151° to 153° C.

(35) 2,2,2-Trichloroethyl 2-methyl-7-(2-allylthioacetamido)-3-cephem-4-carboxylate, mp 96° C.

(36) 2,2,2-Trichloroethyl 2-methyl-7-(2-formyloxy-2-phenylacetamido)-3-cephem-4-carboxylate, powder.

(37) 2,2,2-Trichloroethyl 2-methyl-7-(1-cyclopropylethoxy)carboxamido-3-cephem-4-carboxylate, mp 181° to 183° C.

(38) 2-Methyl-7-(phenylglycyl)amino-3-cephem-4-carboxylic acid, mp 168.5° to 171° C.

(39) 2-Methyl-7-{3-amino-3-(2-thienyl)-propionamido}-3-cephem-4-carboxylic acid, mp 218° to 221° C. (dec.).

(40) 2-Methyl-7-{2-(2-thienyl)glycyl}amino-3-cephem-4-carboxylic acid, mp 145° to 149° C. (dec.).

(41) 2-Methyl-7-(2-hydroxy-2-phenylacetamido)-3-cephem-4-carboxylic acid, mp 172° to 173° C.

(42) 2,2,2-Trichloroethyl 2-methyl-7-amino-3-cephem-4-carboxylate hydrochloride, mp 185° to 187° C. (dec.).

(43) 2-Methyl-7-amino-3-cephem-4-carboxylic acid, mp 220° C. (dec.).

(44) 2-Methyl-7-[2-(2-aminothiazol-4-yl)acetamido]-3-cephem-4-carboxylic acid, which can be represented as 2-methyl-7-[2-(2-imino-2,3-dihydrothiazol-4-yl)acetamido]-3-cephem-4-carboxylic acid, mp 250° to 255° C. (dec.).

(45) Pivaloyloxymethyl 2-methyl-7-[2-(2-aminothiazol-4-yl)acetamido]-3-cephem-4-carboxylate hydrochloride, which can be represented as pivaloyloxymethyl 2-methyl-7-[2-(2-imino-2,3-dihydrothiazol-4-yl)acetamido]-3-cephem-4-carboxylate hydrochloride, mp 185° to 190° C. (dec.).

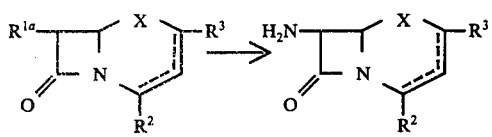

EXAMPLE 16

A solution of 2-methyl-7-(1-cyclopropylethoxy)carboxamido-3-cephem-4-carboxylic acid (0.5 g.) in formic acid (5 ml.) was stirred for 2 hours at room temperature. Ether (20 ml.) was added under icecooling to the reaction mixture, and the supernatant was removed by decantation which procedure was repeated three times. The precipitate was collected by filtration, washed with ether. The precipitate was added under ice-cooling to a mixture of acetonitrile (5 ml.) and water (1 ml.). The mixture was stirred for 1 hour at the same temperature, and the insoluble material was collected by filtration, and dried to give 2-methyl-7-amino-3-cephem-4-carboxylic acid (0.24 g.), mp 222° C. (dec.).

EXAMPLE 17

Pyridine (0.55 g.) and phosphorus pentachloride (1.43 g.) were added in turn under cooling at −5 to −10° C. to a suspension of 2,2,2-trichloroethyl 2-methyl-7-(2-phenylacetamido)-3-cephem-4-carboxylate (2.14) in dried dichloromethane (20 ml.), and the mixture was stirred. After dissolution of the starting material, the reaction temperature was elevated to at room temperature, and stirred for 4 hours. To this solution was dropwise added absolute methanol (1.47 g.) under cooling at −10° to −15° C. After stirring for 1 hour at the same temperature and 1.5 hours at 2° to 3° C., the precipitated crystals were collected by filtration, washed with a small amount of dichloromethane and ether, and dried to give colorless crystals of 2,2,2-trichloroethyl 2-methyl-7-amino-3-cephem-4-carboxylate hydrochloride (1.26 g.), mp 185° to 187° C. (dec.). Similar results were obtained by using the following compounds as a starting compound instead of 2,2,2-trichloroethyl 2-methyl-7-(2-phenylacetamido)-3-cephem-4-carboxylate.

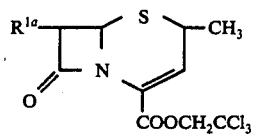

| No. | $R^{1a}$ | Property |
|---|---|---|
| 1 | ⌬—CH(NHCOOCHCH₃-cyclopropyl)CONH— | mp 165 to 167.5° C |
| 2 | (tetrazolyl: N=N, N=CH)N—CH₂CONH— | mp 168 to 170° C |
| 3 | (thienyl)—CH₂CONH— | mp 161 to 162° C (dec.) |
| 4 | ⌬—S—CH₂CONH— | mp 140 to 142° C |
| 5 | ⌬—CH₂OCONH— | mp 143 to 144° C |
| 6 | (thienyl)—CHCH₂CONH—, NHCOOC(CH₃)₃ | mp 188 to 192° C |
| 7 | NC—CH₂CONH— | mp 160 to 165° C (dec.) |
| 8 | ⌬—NHCONH— | mp 172 to 174° C |
| 9 | (thiadiazolyl: N—N, S)—S—CH₂CONH— | mp 130 to 140° C (dec.) |
| 10 | (thienyl)—CHCONH—, NHCOOC(CH₃)₃ | Amorphous |
| 11 | $N_3C$—(thiadiazolyl: N—N, S)—OCH₂CONH— | Amorphous |
| 12 | (2-Cl-phenyl)-isoxazolyl(CH₃)—CONH— | Amorphous |
| 13 | CH₃—S—CH₂CONH— | mp 151 to 153° C |
| 14 | CH₂=CHCH₂SCH₂CONH— | mp 96° C |
| 15 | ⌬—CHCONH—, OCHO | mp 142 to 147° C |

-continued

| No. | R¹ᵃ | Property |
|---|---|---|
| 16 | 3-Cl-C₆H₄-CH₂CONH— | mp 144 to 145.5° C (dec.) |
| 17 | (1,2,4-thiadiazol-3-yl)-CH₂CONH— | mp 180 to 185° C (dec.) |
| 18 | C₆H₅-O-CH₂CONH— | mp 118 to 120° C (dec.) |

(structure: R¹ᵃ—β-lactam-cephem with COOCH₂CCl₃)

EXAMPLE 18

Trimethylchlorosilane (55 ml.) was added to a suspension of 2-methyl-7-(2-phenylacetamido)-3-cephem-4-carboxylic acid (18.15 g.) in dichloromethane (400 ml.), and the mixture was stirred for 10 minutes.

To the mixture was added dimethylaniline (41.5 ml.), and the mixture was refluxed for 1 hour. After the mixture was cooled at −30° to −40° C., to a mixture was added phosphorus pentachloride (16.6 g.), and the mixture was stirred for 2 hours at the same temperature, after which methanol (185 ml.) was added to the solution and the mixture was stirred for 1 hour at the same temperature. Water (250 ml.) was added to the reaction mixture and this solution was stirred for 30 minutes at −10° to 0° C., after which the aqueous layer was separated. The aqueous layer was adjusted to pH 3 to 4 with 1N sodium hydroxide aqueous solution at 0° to 10° C., and the precipitated crystals were collected by filtration, washed in turn with water, acetone and ether, and then dried to give white crystals of 2-methyl-7-amino-3-cephem-4-carboxylic acid (6.9 g.), mp 222° C. (dec.).

Similar results were obtained by using the following compounds as a starting compound instead of 2-methyl-7-(2-phenylacetamido)-3-cephem-4-carboxylic acid.

(structure: R¹ᵃ—β-lactam-cephem with COOH)

| No. | R¹ᵃ | Property |
|---|---|---|
| 1 | C₆H₅-CH(NHCOOCH-cyclopropyl)CONH— | mp 168 to 169° C |
| 2 | (1,2,3-triazol-1-yl)-CH₂CONH— | mp 202 to 203° C (dec.) |
| 3 | (2-thienyl)-CH₂CONH— | mp 175° C (dec.) |
| 4 | C₆H₅-S-CH₂CONH— | mp 168 to 171° C |
| 5 | C₆H₅-CH₂OCONH— | mp 167 to 169° C (dec.) |
| 6 | (2-thienyl)-CH(NHCOOC(CH₃)₃)CH₂CONH— | mp 167 to 170° C (dec.) |
| 7 | NC-CH₂CONH— | mp 162 to 166° C |
| 8 | C₆H₅-NHCONH— | mp 148 to 151° C |
| 9 | (1,3,4-thiadiazol-2-yl)-S-CH₂CONH— | mp 197 to 199° C |
| 10 | (2-thienyl)-CH(NHCOOC(CH₃)₃)CONH— | Amorphous |
| 11 | (5-azido-1,3,4-thiadiazol-2-yl)-OCH₂CONH— | mp 113 to 116° C |
| 12 | 2-Cl-C₆H₄-(5-methylisoxazol-4-yl)-CONH— | mp 202 to 203° C |
| 13 | CH₃-S-CH₂CONH— | mp 181 to 183° C (dec.) |
| 14 | CH₂=CHCH₂SCH₂CONH— | mp 121 to 123° C |
| 15 | C₆H₅-CH(OCHO)CONH— | Amorphous |
| 16 | 3-Cl-C₆H₄-CH₂CONH— | mp 173 to 174° C (dec.) |
| 17 | (3-pyridyl)-CH₂CONH— | mp 147 to 149° C (dec.) |
| 18 | 4-HO-C₆H₄-CH(NHCOOC(CH₃)₃)CONH— | Powder |

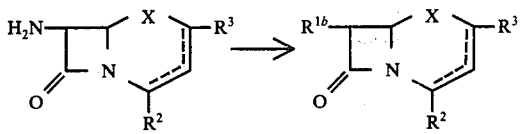

EXAMPLE 19

A solution of N-(1-cyclopropylethoxycarbonyl)-phenylglycine (1.63 g), triethylamine (0.60 g) and dimethylbenzylamine (2 drops) in dried dichloromethane (10 ml) was dropwise added at −10° C. to a solution of ethyl chloroformate (0.67 g) in dried dichloromethane (15 ml), and the mixture was stirred for 1 hour. The mixture was cooled at −10° to 15° C. and to the mixture was dropwise added over 10 minutes a solution of 2,2,2-trichloroethyl 2-methyl-7-amino-3-cephem-4-carboxylate hydrochloride (2.2 g) and triethylamine (0.55 g) in dried dichloromethane (20 ml), after which the mixture was stirred for 2.5 hours at the same temperature. After the reaction, the reaction mixture was in turn washed with water, 2% hydrochloric acid, a saturated sodium bicarbonate aqueous solution and a saturated sodium chloride aqueous solution and then dried over magnesium sulfate. After the solvent was distilled off under reduced pressure, the residue was pulverized by adding isopropyl ether, after which the powder was collected by filtration and dried to give 2,2,2-trichloroethyl 2-methyl-7-[N-(1-cyclopropylethoxy)carbonylphenylglycyl]amino-3-cephem-4-carboxylate (3.0 g), mp 165° to 167.5° C.

EXAMPLE 20

A solution of 2-(1H-tetrazol-1-yl)acetic acid (1.08 g), triethylamine (0.96 g) and dimethylbenzylamine (2 drops) in dried dichloromethane (10 ml) was dropwise added over 10 minutes at −10° C. to a solution of pivaloyl chloride (1.20 g) in dried dichloromethane (20 ml), and the mixture was stirred for 1 hour at the same temperature. A solution of 2,2,2-trichloroethyl 2-methyl-7-amino-3-chephem-4-carboxylate hydrochloride (3.05 g) and triethylamine (0.8 g) in dried dichloromethane (20 ml) was dropwise added over 10 minutes to the mixture, and the mixture was stirred for 3 hours. After the reaction, the reaction mixture was in turn washed with water, 5% hydrochloric acid, a saturated sodium becarbonate aqueous solution and a saturated sodium chloride aqueous solution, and then dried over magnesium solfate. After the solvent was distilled off, the obtained residue was washed with ether and collected by filtration to give colorless crystals of 2,2,2-trichloroethyl 2-methyl-7-[2-(1H-tetrazol-1-yl)acetamido]-3-cephem-4-carboxylate (2.34 g), mp 168° to 170° C.

EXAMPLE 21

2,2,2-Trichloroethyl 2-methyl-7-amino-3-cephem-4-carboxylate hydrochloride (3.0 g) was suspended in dried dichloromethane (50 ml) and then dissolved by adding triethylamine (0.72 g) and dimethylaniline (1.9 g) under cooling at −15° C. To a solution was dropwise added a solution of (2-thienyl)acetyl chloride (2.0 g) in dried dichloromethane (10 ml) under stirring and cooling at the same temperature, and the mixture was stirred for 1.5 hours at the same temperature. After the reaction, the reaction mixture was in turn washed with 5% hydrochloric acid, water, 5% sodium bicarbonate aqueous solution and water and then dried. After the solvent was distilled off, the residue was dissolved in ether, allowed to stand, after which the precipitated crystals were collected by filtration and dried to give crystals of 2,2,2-trichloroethyl 2-methyl-7-[2-(2-thienyl)acetamido]-3-cephem-4-catboxylate (3.2 g), mp 161° to 162° C. (dec.).

EXAMPLE 22

2,2,2-Trichloroethyl 2-methyl-7-amino-3-cephem-4-carboxylate hydrochloride (3.0 g) was suspended in dried dichloromethane (50 ml) and then dissolved by adding triethylamine (0.72 g) and dimethylamiline (1.9 g) under cooling at −15° C. To a mixture was dropwise added a solution of phenylthioacetyl chloride (2,2 g) in dried dichloromethane (10 ml) under stirring, and the mixture was stirred for 1.5 hours at the same temperature. After the reaction, the reaction mixture was in turn washed with 5% hydrochloric acid, water, 5% sodium bicarbonate aqueous solution and water and then dried. After the solvent was distilled off, ether was added to the residue, after which the precipitated crystals were collected by filtration and dried to give 2,2,2-trichloroethyl 2-methyl-7-(2-phenylthioacetamido)-3-cephem-4-carboxylate (3.4 g), mp 140° to 142° C.

EXAMPLE 23

A solution of 2,2,2-trichloroethyl 2-methyl-7-amino-3-cephem-4-carboxylate hydrochloride (3.0 g, triethylamine (0.72 g) and dimethylaniline (1.9 g) in dried dichloromethane (50 ml) was dropwise added at −15° C. over 1.5 hours to a solution of benzyl chloroformate (2.2 g) in dried dichloromethane (10 ml), and the mixture was stirred for 1 hour at the same temperature. After the reaction, the reaction mixture was in turn washed with 5% hydrochloric acid, water, 5% sodium bicarbonate aqueous solution and water and then dried. After the solvent was distilled off, the residue was dissolved in ethanol, after which the precipitated crystals were collected by filtration and dried to give crystals of 2,2,2-trichloroethyl 2-methyl-7-benzyloxycarboxamido-3-cephem-4-carboxylate (3.2 g), mp 143° to 144° C.

EXAMPLE 24

A solution of 3-(N-tert.-butoxycarbonylamino)-3-(2-thienyl)propionic acid (795 mg) and triethylamine (240 mg) in dichloromethane (10 ml) was dropwise added under cooling at −15° to −10° C. over about 20 minutes to a solution of isobutyl chloroformate (330 mg) in dried dichloromethane (10 ml). The mixture was further stirred for 1 hour at the same temperature to give the solution of the mixed anhydride. A solution which was prepared by adding triethylamine (160 mg) and dimethylaniline (50 mg) to a solution of 2,2,2-trichloroethyl 2-methyl-7-amino-3-cephem-4-carboxylate hydrochloride (760 mg) in dichloromethane was added at −15° to −10° C. to the above mentioned mixed anhydride solution, after which the mixture was stirred for 3 hours at the same temperature and further 3 hours at room temperature. After the reaction, dichloromethane was distilled off. The residue was dissolved in ethyl acetate (150 ml), and the solution was in turn washed with 5% hydrochloric acid (20 ml), 5% sodium bicarbonate aqueous solution and a saturated sodium chloride aqueous solution and then dried over magnesium sulfate. The solvent was distilled off under reduced pressure to give 2,2,2-trichloroethyl 2-methyl-7-[3-(N-tert.-butoxycarbonylamino)-3-(2-thiehyl)-propionamido]-3-cephem-4-carboxylate (1.17 g), mp 188° to 192° C.

EXAMPLE 25

A solution of triethylamine (0.9 g) and dimethylaniline (0.15 g) in dichloromethane (20 ml) was added under stirring and ice-cooling to a suspension of 2,2,2-trichloroethyl 2-methyl-7-amino-3-cephem-4-carboxylate hydrochloride (3.82 g) in dried dichloromethane (80 ml). To the mixture were added cyanoacetic acid (0.85 g) and dicyclohexylcarbodiimide (2.25 g), and the mixture was stirred for 1 hour under ice-cooling. To the mixture was added 5% hydrochloric acid (50 ml), and the mixture was stirred for 30 minutes, after which the organic layer was separated, washed in turn with 5% hydrochloric acid, a saturated sodium bicarbonate aqueous solution and a saturated sodium chloride aqueous solution and then dried over magnesium sulfate. The solvent was distilled off to give colorless powder of 2,2,2-trichloroethyl 2-methyl-7-(2-cyanoacetamido)-3-cephem-4-carboxylate (3.5 g), mp 160° to 165° C. (dec.).

EXAMPLE 26

2,2,2-Trichloroethyl 2-methyl-7-amino-3-cephem-4-carboxylate hydrochloride (3.82 g) was suspended in dichloromethane (30 ml), and then dissolved by adding triethylamine (0.9 g) and dimethylaniline (0.1 g). To the solution was added phenylisocyanate (1.2 g) under stirring and ice-cooling, and the mixture was stirred for 5 hours. 10% Hydrochloric acid was added to the reaction mixture, and the mixture was stirred for 10 minute. The reaction mixture was filtered, and the dichloromethane layer was separated from the filtrate, washed in turn with a saturated sodium bicarbonate aqueous solution and a saturated sodium chloride aqueous solution and dried over magnesium sulfate. The solvent was distilled off to give 2,2,2-trichloroethyl 2-methyl-7-(3-phenylureido)-3-cephem-4-carboxylate (4.2 g), mp 172° to 174° C.

EXAMPLE 27

2,2,2-Trichloroethyl 2-methyl-7-amino-3-cephem-4-carboxylate hydrochloride (3.82 g) was suspended in dried dichloromethane (80 ml) and dissolved by adding under stirring and ice-cooling a solution of triethylamine (0.9 g) and dimethylaniline (0.15 g) in dichloromethane (20 ml). To the solution were added (1,3,4-thiadiazol-2-ylthio)acetic acid (1.8 g) and dicyclohexylcarbodiimide (2.25 g) under stirring and ice-cooling, and the mixture was stirred for 1 hour under ice-cooling. To the reaction mixture, was added 5% hydrochloric acid (50 ml), and the mixture was stirred for 30 minutes, after which the organic layer was separated, washed in turn with 5% hydrochloric acid, a saturated sodium bicarbonate aqueous solution and a saturated sodium chloride aqueous solution, and then dried over magnesium sulfate. The solvent was distilled off to give pale brown powder of 2,2,2-trichloroethyl 2-methyl-7-[2-(1,3,4-thiadiazol-2-ylthio)acetamido]-3-cephem-4-carboxylate (4.5 g), mp 130° to 140° C. (dec.).

EXAMPLE 28

[N-Tert.-butoxycarbonyl-2-(2-thienyl)]-glycine (930 mg) was added to dried dichloromethane (15 ml) and dissolved, by adding triethylamine (360 mg). To a solution was dropwise added a solution of pivaloyl chloride (400 mg) in dichloromethane (1 ml) under stirring and cooling at −10° to −15° C., and the mixture was stirred for 2 hours at the same temperature to give the solution of mixed anhydride. 2,2,2-Trichloroethyl 2-methyl-7-amino-3-cephem-4-carboxylate hydrochloride (1.15 g) was suspended in dichloromethane (10 ml) and dissolved by stirring for several minutes after addition of 2,6-lutidine (0.64 g) under stirring and ice-cooling. This solution cooled at −10° C. was at once added to the above-mentioned mixed anhydride solution, and the mixture was stirred for 1.5 hours at −15° C. and for 0.5 hour at room temperature. After the reaction, the reaction mixture was concentrated under reduced pressure, and the residue was extracted by adding ethyl acetate and 2 to 3% sulfuric acid. The ethyl acetate layer was in turn washed with water, a saturated sodium bicarbonate aqueous solution and water and dried over magnesium sulfate. After the solvent was removed under reduced pressure, the residue was pulverized by adding a mixture of ether and petroleum ether, collected by filtration and dried to give 2,2,2-trichloroethyl 2-methyl-7-(N-tert.-butoxycarbonyl-2-thienylglycyl)amino-3-cephem-4-carboxylate (1.77 g). Infrared Absorption Spectrum (Nujol) 3320, 1790, 1740, 1710, 1690, 1680, 1632 cm$^{-1}$

EXAMPLE 29

A solution of pivaloyl chloride (2.0 g) in dichloromethane (5 ml) was dropwise added under stirring and cooling at −15° C. to a solution of (5-methyl-1,3,4-thiadiazol-2-yloxy)acetic acid (3.13 g) and triethylamine (1.80 g) in dried dichloromethane (50 ml), and the mixture was stirred for 2 hours at the same temperature to give the mixed anhydride solution. While, 2,2,2-trichloroethyl 2-methyl-7-amino-3-cephem-4-carboxylate hydrochloride (5.75 g) was suspended in dichloromethane (40 ml) and dissolved by stirring for 10–20 minutes after addition of 2,6-lutidine (2.0 g) under ice-cooling and then cooling at −15° C., and then this solution was at once added to the above-mentioned mixed anhydride solution. The mixture was stirred for 1.5 hours at the same temperature and for 30 minutes at room temperature. After the reaction, the reaction mixture was in turn washed with 5% sulfuric acid, water, a saturated sodium bicarbonate aqueous solution and water and dried over magnesium sulfate. The solvent was removed under reduced pressure to give colorless amorphous 2,2,2-trichloroethyl 2-methyl-7-[2-(5-methyl-1,3,4-thiadiazol-2-yloxy)acetamido]-3-cephem-4-carboxylate (7.23 g). Infrared Absorption Spectrum (Chloroform) 3420, 1790, 1740, 1700, 1635 cm$^{-1}$

EXAMPLE 30

Thionyl chloride (5 ml) was added to [3-(2chlorophenyl)-5-methylisoxazol-4-yl]carboxylic acid (855 mg), and the mixture was refluxed for 2 hours, and then thionyl chloride was removed under reduced pressure. Thus obtained [3-(2-chlorophenyl)-5-methylisoxazol-4-yl]-carbonyl chloride was dissolved in dried dichloromethane (3 to 4 ml). 2,2,2-Trichloroethyl 2-methyl-7-amino-3-cephem-4-carboxylate hydrochloride (1.15 g) was suspended in dichloromethane (10 ml) and dissolved by adding triethylamine (250 mg) and 2,6-lutidine (0.64 g), after which the solution was ice-cooled. To this solution was dropwise added the above-mentioned acid chloride solution, and the mixture was stirred for 1 hour under ice-cooling. After the reaction, the reaction mixture was concentrated under reduced pressure, and the residue was extracted by adding ethylacetate and 2% sulfuric acid. The extract was in turn washed with water, a saturated sodium bicarbonate aqueous solution and water, and dried over magnesium sulfate. The solvent was distilled off under reduced pressure to give amorphous 2,2,2-trichloroethyl 2-methyl-7-[3-(2-chlorophenyl)-5-methylisoxazol-4-yl]carboxamido-3-cephem-4-carboxylate (1.82 g). Infrared Absorption Spectrum (Nujol) 3340, 1790, 1740, 1675 cm$^{-1}$

EXAMPLE 31

Methylthioacetic acid (0.42 g) was added to thionyl chloride (5 ml), and the mixture was allowed to stand for 40 minutes at room temperature and for 5 minutes at 40 to 50° C., after which thionyl chloride was removed under reduced pressure. To the residue was added benzene (5 ml), and then removed under reduced pressure to give methylthioacetyl chloride (0.47 g). 2,2,2-Trichloroethyl 2-methyl-7-amino-3-cephem-4-carboxylate hydrochloride (0.764 g) was suspended in dichloromethane (8 ml), and then dissolved by adding a solution of triethylamine (0.18 g) in dichloromethane (2 ml) and a solution of dimethylaniline (0.266 g) in dichloromethane (2 ml) at −30° C. To this solution was added at −30° C. the above obtained methylthioacetyl chloride (0.38 g), and the mixture was stirred for 30 minutes at the same temperature, after which the reaction temperature was gradually elevated to −10° C. over 1 hour under stirring. After the reaction, the reaction mixture was in turn washed with 5% hydrochloric acid, water, a saturated sodium bicarbonate aqueous solution and a saturated sodium chloride aqueous solution, and dried over magnesium sulfate. After the solvent was distilled off, the crystalline residue (0.81 g) was recrystallized from ethanol to give colorless needless of 2,2,2-trichloroethyl 2-methyl-7-[(2-methylthio)acetamido]-3-cephem-4-carboxylate (0.62 g), mp 151° to 153° C.

EXAMPLE 32

To a suspension of 2,2,2-trichloroethyl 2-methyl-7-amino-3-cephem-4-carboxylate hydrochloride (0.764 g) in dried dichloromethane (8 ml) were added at −30° C. a solution of triethylamine (0.18 g) in dichloromethane (2 ml) and then a solution of dimethylaniline (0.27 g) in dichloromethane (2 ml). While, allylthioacetic acid (0.528 g) was added to thionyl chloride (5 ml) and the mixture was allowed to stand for 20 minutes at room temperature and 5 minutes at 50° C., after which thionyl chloride was removed under reduced pressure, and the residue was added a small amount of benzene, and then removed under reduced pressure to give allylthioacetyl chloride (0.527 g). A solution of thus obtained allylthioacetyl chloride (0.452 g) in dichloromethane (3 ml) was dropwise added to −30° C. over 5 minutes to the above-mentioned solution of 2,2,2-trichloroethyl 2-methyl-7-amino-3-cephem-4-carboxylate, and the mixture was stirred for 1 hour at −20° C. After the reaction, the reaction mixture was in turn washed twice with 5% hydrochloric acid, once with water, twice with a saturated sodium bicarbonate aqueous solution and once with a saturated sodium chloride aqueous solution, and dried over magnesium sulfate. After the solvent was distilled off, the residue (0.82 g) was recrystallized from a mixture of ether and isopropyl ether to give 2,2,2-trichloroethyl 2-methyl-7-(2-allylthioacetamido)-3-cephem-4-carboxylate (0.71 g), mp 96° C.

EXAMPLE 33

A solution of dicyclohexylcarbodiimide (0.99 g) in tetrahydrofuran (5 ml) was dropwise added under stirring and cooling at −20° C. to a solution of (2-formyloxy)phenylacetic acid (0.864 g) in tetrahydrofuran (15 ml), and the mixture was stirred for 30 minutes at the same temperature. To the solution was dropwise added at −20° C. a solution which was prepared by adding 2,2,2-trichloroethyl 2-methyl-7-amino-3-cephem-4-carboxylate hydrochloride (1.53 g) and triethylamine (0.4 g) at −20° C. to dichloromethane (20 ml). The reaction temperature of the mixture was gradually elevated to 0° C. over 1.5 hours under stirring. The reaction mixture was stirred for additional 1.5 hours at 0° C., followed by filtration of the precipitates, and the filtrate was concentrated to dryness under reduced pressure. A small amount of ethyl acetate was added to the residue, followed by filtration of the insoluble material, and the filtrate was in turn washed with 5% hydrochloric acid, water, a saturated sodium bicarbonate aqueous solution and a saturated sodium chloride aqueous solution, and dried over magnesium sulfate. After the solution was filtered by passing through silicagel (about 2 g), the solvent was distilled off, after which the residue was pulverized by adding ether, collected by filtration, and dried to give 2,2,2-trichloroethyl 2-methyl-7-(2-formyloxy-2-phenyl-acetamido)-3-cephem-4-carboxylate (1.72 g), mp 142° to 147° C.

EXAMPLE 34

Triethylamine (1.02 g) was added to a suspension which was prepared by suspending 2,2,2-trichloroethyl 2-methyl-7-amino-3-cephem-4-carboxylate hydrochloride (1.92 g) in tetrahydrofuran (20 ml) under cooling at −10° C. And then the mixture was vigorously stirred. To the solution, was dropwise added over about 10 minutes a solution of 1-cyclopropylethyl chloroformate (5.5m mole) in tetrahydrofuran (20 ml), and the mixture was stirred for 1.5 hours at the same temperature. After the reaction was completed, the reaction mixture was filtered, and the filtrate was concentrated below room temperature. The residue was dissolved in ethyl acetate (30 ml), and this solution was in turn washed with 5% hydrochloric acid, a sodium bicarbonate aqueous solution and a saturated sodium chloride aqueous solution, and dried over magnesium sulfate, after which the solvent was distilled off. The residue was pulverized by adding a small amount of isopropyl ether. The powder was collected by filtration and dried to give 2,2,2-trichloroethyl 2-methyl-7-(1-cyclopropylethoxy)carboxamido-3-cephem-4-carboxylate (1.4 g), mp 181° to 183° C.

EXAMPLE 35

A mixture of 2-methyl-7-amino-3-cephem-4-carboxylic acid (0.214 g), bis(trimethylsilyl)acetamide (0.40 g) and dichloromethane (4 ml) was homogenized by stirring for 30 to 40 minutes at room temperature, and to this solution was dropwise added over about 15 minutes under stirring and cooling at −15° to −20° C. a solution of triethylamine salt of mixed anhydride of 2-sulfo-2-phenylacetic acid with ethoxycarbonic acid (0.389 g) in dried dichloromethane (4 ml), after which the mixture was stirred for 2 hours at −10° to −15° C. After the reaction, dichloromethane was removed. To the residue was added ethyl acetate, and the mixture was allowed to stand, after which the precipitate was extracted with water. The extract was washed with ethyl acetate and lyophilized. The residual powder was dissolved in a small quantity of water, and the solution was adjusted to pH 6 to 7 by adding sodium bicarbonate.

After water was distilled off, the residue was washed with ethanol and pulverized to give disodium salt of 2-methyl-7-(2-sulfo-2-phenylacetamido)-3-cephem-4-carboxylic acid (0.1 g) mp 265° C. (dec.). This compound was treated according to the conventional manner to give 2-methyl-7-(2-sulfo-2-phenylacetamido)-3-cephem-4-carboxylic acid, 115° C. (vesication), 200° to 220° C. (dec.).

EXAMPLE 36

A suspension of 2,2,2-trichloroethyl-2-methyl-7-amino-3-cephem-4-carboxylate hydrochloride (6.9 g) in dried dichloromethane (70 ml) was homogenized by adding triethylamine (1.48 g) and N,N-dimethylaniline (0.44 g) under stirring and ice-cooling and by stirring for 30 minutes at room temperature. A solution of triethylamine salt of mixed anhydride of 2-sulfo-2-phenylacetic acid with ethoxycarbonic acid (8.5 g) in dried dichloromethane (60 ml) was dropwise added over about 30 minutes under stirring and cooling at −20° to −25° C. to the above-mentioned solution, and the mixture was stirred for 1.5 hours at −10° to −15° C. and for 1 hour at room temperature. After the reaction, dichloromethane was removed at low temperature, and the residue was dissolved in ethyl acetate, after which the solution was washed with cooled 5% hydrochloric acid and three times with water, and then dried. The solvent was distilled off at low temperature to give 2,2,2-trichloroethyl 2-methyl-7-(2-sulfo-2-phenylacetamido)-3-cephem-4-carboxylate (11.5 g), amorphous.

EXAMPLE 37

A mixture of dimethylformamide (0.805 g) and thionyl chloride (1.55 g) was warmed for 30 minutes at 50° C. with enough shaking, and then excess thionyl chloride was removed under reduced pressure. The residual crystals were washed twice with a small amount of absolute ether, and then ether was removed under reduced pressure. The residual crystals were dissolved in dried dichloromethane (40 ml), and to the solution was added at 0° C. thienylglycolic acid (0.95 g). The mixture was cooled at −50° C., and to the mixture was dropwise added over 30 minutes a solution of triethylamine (1.11 g) in dried dichloromethane (10 ml), after which the mixture was stirred for 30 minutes at the same temperature. To the solution was dropwise added over 30 minutes at −50° C. a solution which was prepared by stirring a mixture of 2-methyl-7-amino-3-cephem-4-carboxylic acid (1.075 g), bis(triethylsilyl)acetamide (2.04 g) and dried dichloromethane (25 ml) for 2 hours at room temperature. The mixture was stirred for 2 hours at the same temperature and for 1 hour at −20° to −30° C. After the reaction, water (10 ml) was added at 0° C. to the reaction mixture, and then dichloromethane was removed under reduced pressure. To the residue was added water (40 ml), after which the solution was extracted twice with ethyl acetate (50 ml). The extract was extracted three times with a sodium bicarbonate aqueous solution (50 ml), and the aqueous extract was washed with ethyl acetate (50 ml), adjusted to pH2 with 5% sulfuric acid and extracted three times with ethyl acetate (30 ml), after which the extract was washed with water and dried. After the solvent was distilled off, the residue was pulverized by adding isopropyl ether to give pale yellow powder of 2-methyl-7-[2-hydroxy-2-(2-thienyl)-acetamido]-3-cephem-4-carboxylic acid (1.32 g), mp 91° to 96° C. (dec.).

The following compounds were obtained in the similar manners as described in the above mentioned Examples.

(1) 2,2,2-Trichloroethyl 2-methyl-7-(2-phenylacetamido)-3-cephem-4-carboxylate, mp 175° to 178° C.

(2) 2,2,2-Trichloroethyl 2-methyl-7-(2-phenylacetamido)-2-cephem-4-carboxylate, mp 136° to 137° C.

(3) 2,2,2-Trichloroethyl 2-methyl-7-[2-(3-chlorophenyl)acetamido]-3-cephem-4-carboxylate, mp 144° to 144.5° C. (dec.).

(4) 2,2,2-Trichloroethyl 2-methyl-7-[2-(1,2,5-thiadiazol-3-yl)acetamido]-3-cephem-4-carboxylate, mp 180° to 185° C. (dec.).

(5) Methyl 2-methyl-7-(2-phenoxyacetamido)-3-cephem-4-carboxylate, oil.

(6) 2,2,2-Trichloroethyl 2-methyl-7-(2-phenoxyacetamido)-3-cephem-4-carboxylate, mp 118° to 120° C.

(7) 2,2,2-Trichloroethyl 2-methyl-7-(2-phenylacetamido)-3-cephem-4-carboxylate-1-oxide, mp 173° to 175° C.

(8) 2-Methyl-7-[N-(1-cyclopropylethoxy)carbonylphenylglycyl]amino-3-cephem-4-carboxylic acid, mp 168° to 169° C.

(9) 2-Methyl-7-[2-(1H-tetrazol-1-yl)acetamido]-3-cephem-4-carboxylic acid, mp 202° to 203° C. (dec.).

(10) 2-Methyl-7-[2-(2-thienyl)acetamido]-3-cephem-4-carboxylic acid, mp 175° C. (dec.).

(11) 2-Methyl-7-benzyloxycarboxamido-3-cephem-4-carbolic acid, mp 167° to 169° C. (dec.).

(12) 2-Methyl-7-(2-phenylthioacetamido)-3-cephem-4-carboxylic acid, mp 168° to 171° C. (dec.).

(13) 2-Methyl-7-[2-(3-chlorophenyl)acetoamido]-3-cephem-4-carboxylic acid, mp 173° to 174° C. (dec.).

(14) 2-Methyl-7-[3-(N-tert.-butoxycarbonylamino)-3-(2-thienyl)propionamido]-3-cephem-4-carboxylic acid, mp 167° to 170° C. (dec.).

(15) 2-Methyl-7-(2-cyanoacetamido)-3-cephem-4-carboxylic acid, mp 162° to 166° C.

(16) 2-Methyl-7-(3-phenylureido)-3-cephem-4-carboxylic acid, mp 148° to 151° C.

(17) 2-Methyl-7-[2-(1,3,4-thiadiazol-2-ylthio)acetamido]-3-cephem-4-carboxylic acid, mp 197° to 199° C.

(18) 2-Methyl-7-[N-tert.butoxycarbonyl-2-thienylglycyl]amino-3-cephem-4-carboxylic acid, powder.

(19) 2-Methyl-7-[2-(5-methyl-1,3,4-thiadiazol-2-yloxy)acetamido]-3-cephem-4-carboxylic acid, mp 113° to 116° C.

(20) 2-Methyl-7-[3-(2-chlorophenyl)-5-methylisoxazol-4-yl]carboxamido-3-cephem-4-carboxylic acid, mp 202° to 203° C.

(21) 2-Methyl-7-(2-methylthioacetamido)-3-cephem-4-carboxylic acid, mp 181° to 183° C. (dec.).

(22) 2-Methyl-7-(2-allylthioacetamido)-3-cephem-4-carboxylic acid, mp 121° to 123° C.

(23) 2-Methyl-7-(2-formyloxy-2-phenylacetamido)-3-cephem-4-carboxylic acid, powder.

(24) 2-Methyl-7-(1-cyclopropylethoxy)carboxamido-3-cephem-4-carboxylic acid, mp 158.5° to 160° C. (dec.).

(25) 2-Methyl-7-(2-azido-2-phenylacetamido)-3-cephem-4-carboxylic acid, mp 65° to 68° C.

(26) 2,2,2-trichloroethyl 2-methyl-7-[N-tert.-butoxycarbonyl-2-(4-hydroxyphenyl)-D-glycyl]amino-3-cephem-4-carboxylate, mp 130° to 135° C. (dec.).

(27) 2-Methyl-7-[2-(3-pyridyl)acetamido]-3-cephem-4-carboxylic acid, mp 147° to 149° C. (dec.).

(28) 2-Methyl-7-[N-tert.-butoxycarbonyl-2-(2,5-dihydrophenyl)glycyl]amino-3-cephem-4-carboxylic acid, mp 126° to 131° C. (dec.).

(29) 2-Methyl-7-[N-tert.-butoxycarbonyl-2-(4-hydroxyphenyl)-D-glycyl]amino-3-cephem-4-carboxylic acid, powder.

(30) 2-Methyl-7-N-tert.-butoxycarbonyl-2-(4-methylthiophenyl)glycyl amino-3-cephem-4-carboxylic acid, mp 110° to 120° C.

(31) 2-Methyl-7-[N-tert.-butoxycarbonyl-2-(4-methoxyphenyl)glycyl]amino-3-cephem-4-carboxylic acid, mp 81° to 86° C. (dec.)

(32) 2,2,2-Trichloroethyl 2-methyl-7-[N-tert.-butoxycarbonyl-2-(4-methylthiophenyl)-glycyl amino]-3-cephem-4-carboxylate, mp 115° to 120° C.

(33) 2,2,2-Trichloroethyl 2-methyl-7-[N-tert.-butoxycarbonyl-2-(4-methoxyphenyl)-glycyl]amino-3-cephem-4-carboxylate, mp 92° to 95° C. (dec.).

(34) 2,2,2-Trichloroethyl 2-methyl-7-[N-tert.-butoxycarbonyl-2-(2,5-dihydrophenyl)-glycyl]amino-3-cephem-4-carboxylate, mp 104° to 110° C. (dec.).

(35) 2,2,2-Trichloroethyl 2-methyl-7-[N-(1-cyclopropylethoxy)carbonyl-2-(5,6-dihydro-2H-pyran-3-yl)glycyl]amino-3-cephem-4-carboxylate, mp 118° to 126° C. (dec.).

(36) 2,2,2-Trichloroethyl 2-methyl-7-[N-tert.-butoxycarbonyl-2-(4-tert.-butoxycarbonylmethoxyphenyl)glycyl]amino-3-cephem-4-carboxylate, powder.

(37) 2,2,2-Trichloroethyl 2-methyl-7-[N-(1,3,4-thiadiazol-2-yl)thiomethylcarbonyl-2-phenylglycyl]amino-3-cephem-4-carboxylate, mp 148° to 150° C. (dec.).

(38) 2,2,2-Trichloroethyl 2-methyl-7-[N-tert.-butoxycarbonyl-2-(4-methylsulfinylphenylglycyl]amino-3-cephem-4-carboxylate, mp 115° to 125° C.

(39) 2-Methyl-7-(2-isonicotinoyloxy-2-phenylacetamido)-3-cephem-4-carboxylic acid, mp 217° to 219° C.

(40) 2,2,2-Trichloroethyl 2-methyl-7-(2-isonicotinoyloxy-2-phenylacetamido)-3-cephem-4-carboxylate, mp 100° to 115° C. (dec.).

(41) 2,2,2-Trichloroethyl 2-methyl-7-[2-(5-indanyl)oxycarbonyl-2-phenylacetamido]-3-cephem-4-carboxylate, mp 165° to 170° C.

(42) 2-Methyl-7-[N-(1,3,4-thiadiazol-2-yl)thiomethylcarbonyl-2-phenylglycyl]amino-3-cephem-4-carboxylic acid, mp 143° to 145° C. (dec.).

(43) 2-Methyl-7-[N-tert.-butoxycarbonyl-2-(4-tert.-butoxycarbonylmethoxyphenyl)glycyl]amino-3-cephem-4-carboxylic acid, powder.

(44) 2-Methyl-7-[N-(1-cyclopropylethoxy)carbonyl-2-(5,6-dihydro-2H-pyran-3-yl)glycyl]amino-3-cephem-4-carboxylic acid, mp 195° to 197° C.

(45) 2-Methyl-7-[2-(1,2,5-thiadiazol-3-yl)-acetamido]-3-cephem-4-carboxylic acid, mp 188° to 190° C. (dec.).

(46) 2-Methyl-7-[N-tert.-butoxycarbonyl-2-(3-methanesulfonamidophenyl)glycyl]amino-3-cephem-4-carboxylic acid, oil.

(47) 2-Methyl-7-[N-tert.-butoxycarbonyl-2-(4-methylsulfinylphenyl)glycol amino-3-cephem-4-carboxylic acid, mp 110° to 120° C.

(48) 2-Methyl-7-[2-(5-indenyl)oxycarbonyl-2-phenylacetamido]-3-cephem-4-carboxylic acid, 90° to 95° C. (softening), 150° to 160° C. (dec.).

(49) 2,2,2-Trichloroethyl 2-methyl-7-[2-(5,6-dihydro-2H-pyran-3-yl)acetamido]-3-cephem-4-carboxylate, mp 149.5° to 150.5° C.

(50) 2-Methyl-7-[2-(5,6-dihydro-2H-pyran-3-yl)-acetamido]-3-cephem-4-carboxylic acid, mp 172.5° to 173.5° C. (dec.).

(51) 2,2,2-Trichloroethyl 2-methyl-7-[N-tert.-butoxycarbonyl-2-(3-methanesulfonamidophenyl)glycyl]amino-3-cephem-4-carboxylate, amorphous.

(52) 2-Methyl-7-(4-methoxyphenyl)glyoxylamido-3-cephem-4-carboxylic acid, mp 188° to 189° C. (dec.).

(53) 2-Methyl-7-(N-tert.-butoxycarbonylphenyl-D-glycyl)amino-3-cephem-4-carboxylic acid, mp 125° to 127° C. (dec.).

(54) 2-Methyl-7-[N-[2-(2-nitrophenoxy)acetyl]phenylglycyl]amino-3-cephem-4-carboxylic acid, mp 135° to 136° C. (dec.).

(55) 2,2,2-Trichloroethyl 2-methyl-7-(N-tert.-butoxycarbonylphenyl-D-glycyl)amino-3-cephem-4-carboxylate, 115° to 116° C. (dec.).

(56) 2-Methyl-7-[2-(2-aminothiazol-4-yl)acetamido]-3-cephem-4-carboxylic acid, which can be represented as 2-methyl-7-[2-(2-imino-2,3-dihydrothiazol-4-yl)acetamido]-3-cephem-4-carboxylic acid, mp 250° to 255° C. (dec.).

(57) Pivaloyloxymethyl 2-methyl-7-[2-(2-aminothiazol-4-yl)acetamido]-3-cephem-4-carboxylate hydrochloride, which can be represented as pivaloyloxymethyl 2-methyl-7-[2-(2-imino-2,3-dihydrothiazol-4-yl)acetamido]-3-cephem-4-carboxylate hydrochloride, mp 185° to 190° C. (dec.).

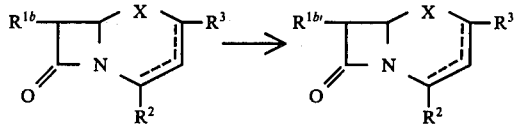

EXAMPLE 38

Pyridine (0.296 g) and phosphorous pentachloride (0.616 g) were added in turn under stirring and cooling at −15° C. to a solution of 2,2,2-trichloroethyl 2-methyl-7-(2-phenylacetamido)-3-cephem-4-carboxylate (1.12 g), mp 175° to 178° C., in dried dichloromethane (20 ml), and the mixture was stirred for 20 minutes at the same temperature and further for 2 hours at room temperature. To the mixture was added absolute methanol (5 ml) under cooling at −15° C., and then the mixture was stirred for 1 hour at the same temperature. To the mixture were dropwise added in turn dimethylaniline (2.2 g) and a solution of 2-thienylacetyl chloride (0.42 g) in dried dichloromethane (5 ml) at the same temperature, and then the mixture was stirred for 2.5 hours at the same temperature. After the reaction, the reaction mixture was in turn washed with 5% hydrochloric acid, water, 5% sodium bicarbonate aqueous solution and water, and then dried. After the solution was concentrated, the obtained oily substance was crystallized by adding ether to give 2,2,2-trichloroethyl 2-methyl-7-[2-(2-thienyl)acetamido]-3-cephem-4-carboxylate (750 mg), mp 161° to 162° C. (dec.).

The following compounds were obtained by using a similar manner as that of the above Example, (1) 2,2,2-Trichloroethyl 2-methyl-7-[2-(3-chlorophenyl)acetamido]-3-cephem-4-carboxylate, mp 144° to 144.5° C. (dec.).

(2) 2,2,2-Trichloroethyl 2-methyl-7-[2-(1,2,5-thiadiazol-3-yl)acetamido]-3-cephem-4-carboxylate, mp 180° to 185° C. (dec.).

(3) Methyl 2-methyl-7-(2-phenoxyacetamido)-3-cephem-4-carboxylate, oil.

(4) 2,2,2-Trichloroethyl 2-methyl-7-(2-phenoxyacetamido)-3-cephem-4-carboxylate, mp 118° to 120° C.

(5) 2-Methyl-7-[N-(1-cyclopropylethoxy)carbonylphenylglycyl]amino-3-cephem-4-carboxylic acid, mp 168° to 169° C.

(6) 2-Methyl-7-[2-(1H-tetrazol-1-yl)acetamido]-3-cephem-4-carboxylic acid, mp 202° to 203° C. (dec.).

(7) 2-Methyl-7-[2-(2-thienyl)acetamido]-3-cephem-4-carboxylic acid, mp 175° C. (dec.).

(8) 2-Methyl-7-(2-phenylthioacetamido)-3-cephem-4-carboxylic acid, mp 168° to 171° C. (dec.).

(9) 2-Methyl-7-[2-(3-chlorophenyl)acetamido]-3-cephem-4-carboxylic acid, mp 173° to 174° C. (dec.).

(10) 2-Methyl-7-[3-(N-tert.-butoxycarbonylamino)-3-(2-thienyl)propionamido]-3-cephem-4-carboxylic acid, mp 167° to 170° C. (dec.).

(11) 2-Methyl-7-(2-cyanoacetamido)-3-cephem-4-carboxylic acid, mp 162° to 166° C.

(12) 2-Methyl-7-[2-(1,3,4-thiadiazol-2-ylthio)acetamido]-3-cephem-4-carboxylic acid, mp 197° to 199° C.

(13) 2-Methyl-7-[N-tert.-butoxycarbonyl-2-thienylglycyl]amino-3-cephem-4-carboxylic acid, powder.

(14) 2-Methyl-7-[2-(5-methyl-1,3,4-thiadiazol-2-yloxy)acetamido]-3-cephem-4-carboxylic acid, mp 113° to 116° C.

(15) 2-Methyl-7-[3-(2-chlorophenyl)-5-methylisoxazol-4-yl]carboxamido-3-cephem-4-carboxylic acid, mp 202° to 203° C.

(16) 2-Methyl-7-(2-methylthioacetamido)-3-cephem-4-carboxylic acid, mp 181° to 183° C. (dec.).

(17) 2-Methyl-7-(2-allylthioacetamido)-3-cephem-4-carboxylic acid, mp 121° to 123° C.

(18) 2-Methyl-7-(2-azido-2-phenylacetamido)-3-cephem-4-carboxylic acid, mp 65° to 68° C.

(19) 2,2,2-trichloroethyl 2-methyl-7-[N-tert.-butoxycarbonyl-2-(4-hydroxyphenyl)-D-glycyl]amino-3-cephem-4-carboxylate, mp 130° to 135° C. (dec.).

(20) 2-Methyl-7-[2-(3-pyridyl)acetamido]-3-cephem-4-carboxylic acid, mp 147° to 149° C. (dec.).

(21) 2-Methyl-7-[N-tert.-butoxycarbonyl-2-(2,5-dihydrophenyl)glycyl]amino-3-cephem-4-carboxylic acid, mp 126° to 131° C. (dec.).

(22) 2-Methyl-7-[N-tert.-butoxycarbonyl-2-(4-hydroxyphenyl)-D-glycyl]amino-3-cephem-4-carboxylic acid, powder.

(23) 2-Methyl-7-[N-tert.-butoxycarbonyl-2-(4-methylthiophenyl)glycyl]amino-3-cephem-4-carboxylic acid, mp 110° to 120° C.

(24) 2-Methyl-7-[N-tert.-butoxycarbonyl-2-(4-methoxyphenyl)glycyl]amino-3-cephem-4-carboxylic acid, mp 81° to 86° C. (dec.).

(25) 2,2,2-Trichloroethyl 2-methyl-7-[N-tert.-butoxycarbonyl-2-(4-methylthiophenyl)glycyl]amino-3-cephem-4-carboxylate, mp 115° to 120° C.

(26) 2,2,2-Trichloroethyl 2-methyl-7-[N-tert.-butoxycarbonyl-2-(4-methoxyphenyl)glycyl]amino-3-cephem-4-carboxylate, mp 92° to 95° C. (dec.).

(27) 2,2,2-Trichloroethyl 2-methyl-7-[N-tert.-butoxycarbonyl-2-(2,5-dihydrophenyl)glycyl]amino-3-cephem-4-carboxylate, mp 104° to 111° C. (dec.).

(28) 2,2,2-Trichloroethyl 2-methyl-7-[N-(1-cyclopropylethoxy)carbonyl-2-(5,6-dihydro-2H-pyran-3-yl)glycyl]amino-3-cephem-4-carboxylate, mp 118° to 126° C. (dec.).

(29) 2,2,2-Trichloroethyl 2-methyl-7-[N-tert.-butoxycarbonyl-2-(4-tert.-butoxycarbonylmethoxyphenyl)glycyl]amino-3-cephem-4-carboxylate, powder.

(30) 2,2,2-Trichloroethyl 2-methyl-7-[N-(1,3,4-thiadiazol-2-yl)thiomethylcarbonyl-2-phenylglycyl]amino-3-cephem-4-carboxylate, mp 148° to 150° C. (dec.).

(31) 2,2,2-Trichloroethyl 2-methyl-7-[N-tert.-butoxycarbonyl-2-(4-methylsulfinylphenyl)glycyl]amino-3-cephem-4-carboxylate, mp 115° to 125° C.

(32) 2-Methyl-7-(2-isonicotinoyloxy-2-phenylacetamido)-3-cephem-4-carboxylic acid, mp 217° to 219° C.

(33) 2,2,2-Trichloroethyl 2-methyl-7-(2-isonicotinoyloxy-2-phenylacetamido)-3-cephem-4-carboxylate, mp 100° to 115° C. (dec.).

(34) 2,2,2-Trichloroethyl 2-methyl-7-[2-(5-indanyl)oxycarbonyl-2-phenylacetamido]-3-cephem-4-carboxylate, mp 165° to 170° C.

(35) 2-Methyl-7-[N-(1,3,4-thiadiazol-2-yl)thiomethylcarbonyl-2-phenylglycyl]amino-3-cephem-4-carboxylic acid, mp 143° to 145° C. (dec.).

(36) 2-Methyl-7-[N-tert.-butoxycarbonyl-2-(4-tert.-butoxycarbonylmethoxyphenyl)glycyl]amino-3-cephem-4-carboxylic acid, powder.

(37) 2-Methyl-7-[N-(1-cyclopropylethoxy)carbonyl-2-(5,6-dihydro-2H-pyran-3-yl)glycyl]amino-3-cephem-4-carbonylic acid, mp 195° to 197° C.

(38) 2-Methyl-7-[2-(1,2,5-thiadiazol-3-yl)acetamido]-3-cephem-4-carboxylic acid, mp 188° to 190° C. (dec.).

(39) 2-Methyl-7-(N-tert.-butoxycarbonyl-2-(3-methanesulfonamidophenyl)glycyl amino-3-cephem-4-carboxylic acid, oil.

(40) 2-Methyl-7-[N-tert.-butoxycarbonyl-2-(4-methylsulfinylphenyl)glycyl]amino-3-cephem-4-carboxylic acid, mp 110° to 120° C.

(41) 2-Methyl-7-[2-(5-indanyl)oxycarbonyl-2-phenylacetamido]-3-cephem-4-carboxylic acid, 90° to 95° C. (softening), 150° to 160° C. (dec.).

(42) 2,2,2-Trichloroethyl 2-methyl-7-[N-(1-cyclopropylethoxy)carbonylphenylglycyl]-amino-3-cephem-4-carboxylate, mp 165° to 167.5° C.

(43) 2,2,2-Trichloroethyl 2-methyl-7-[2-(1H-tetrazol-1-yl)-acetamido]-3-cephem-4-carboxylate, mp 168° to 170° C.

(44) 2,2,2-Trichloroethyl 2-methyl-7-(2-phenylthioacetamido)-3-cephem-4-carboxylate, mp 140° to 142° C.

(45) 2,2,2-Trichloroethyl 2-methyl-7-[3-(N-tert.-butoxycarbonylamino)-3-(2-thienyl)-propionamido]-3-cephem-4-carboxylate, mp 188° to 192° C.

(46) 2,2,2-Trichloroethyl 2-methyl-7-(2-cyanoacetamido)-3-cephem-4-carboxylate, mp 160° to 165° C. (dec.).

(47) 2,2,2-Trichloroethyl 2-methyl-7-[2-(1,3,4-thiadiazol-2-ylthio)acetamido]-3-cephem-4-carboxylate, mp 130° to 140° C. (dec.).

(48) 2,2,2-Trichloroethyl 2-methyl-7-(N-tert.butoxycarbonyl-2-thienylglycyl)amino-3-cephem-4-carboxylate, powder.

(49) 2,2,2-Trichloroethyl 2-methyl-7-[2-(5-methyl-1,3,4-thiadiazol-2-yloxy)acetamido]-3-cephem-4-carboxylate, colorless crystals.

(50) 2,2,2-Trichloroethyl 2-methyl-7-[3-(2-chlorophenyl)-5-methylisoxazol-4-yl]carboxamido-3-cephem-4-carboxylate, amorphous.

(51) 2,2,2-Trichloroethyl 2-methyl-7-(2-methylthioacetamido)-3-cephem-4-carboxylate, mp 151° to 153° C.

(52) 2,2,2-Trichloroethyl 2-methyl-7-(2-allylthioacetamido)-3-cephem-4-carboxylate, mp 96° C.

(53) 2-Methyl-7-(2-sulfo-2-phenylacetamido)-3-cephem-4-carboxylic acid, 115° C. (vesication), 200° to 220° C. (dec.).

(54) 2,2,2-Trichloroethyl 2-methyl-7-(2-sulfo-2-phenylacetamido)-3-cephem-4-carboxylate, amorphous.

(55) 2-Methyl-7-[2-hydroxy-2-(2-thienyl)acetamido]-3-cephem-4-carboxylic acid, mp 91° to 96° C. (dec.).

(56) 2,2,2-Trichloroethyl 2-methyl-7-[2-(5,6-dihydro-2H-pyran-3-yl)acetamido]-3-cephem-4-carboxylate, mp 149.5° to 150.5° C.

(57) 2-Methyl-7-[2-(5,6-dihydro-2H-pyran-3-yl)acetamido]-3-cephem-4-carboxylic acid, mp 172.5° to 173.5° C. (dec.).

(58) 2-Methyl-7-[2-(2-aminothiazol-4-yl)acetamido]-3-cephem-4-carboxylic acid, which can be represented as 2-methyl-7-[2-(2-imino-2,3-dihydrothiazol-4-yl)acetamido]-3-cephem-4-carboxylic acid, mp 250° to 255° C. (dec.).

(59) Pivaloyloxymethyl 2-methyl-7-[2-(2-aminothiazol-4-yl)acetamido]-3-cephem-4-carboxylate hydrochloride, which can be represented as pivaloyloxymethyl 2-methyl-7-[2-(2-imino-2,3-dihydrothiazol-4-yl)acetamido]-3-cephem-4-carboxylate hydrochloride, mp 185° to 190° C. (dec.).

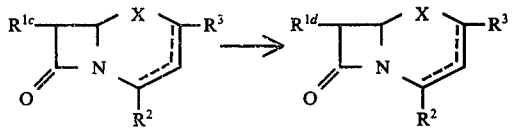

EXAMPLE 39

A solution of 2-methyl-7-[N-(1-cyclopropylethoxy)-carbonyl-2-phenylglycyl]amino-3-cephem-4-carboxylic acid (2.0 g) in formic acid (10 ml) was stirred for 2.5 hours at room temperature. After the reaction was completed, ether (30 ml) was added to the reaction mixture, and the supernatent was removed three times by decantation. Colorless powder was collected by filtration and washed with ether. Thus obtained powder was suspended in a mixture of acetonitrile (15 ml) and water (1 ml), and the suspension was stirred for 1.5 hours under ice-cooling. The precipitate was collected by filtration and dried to give 2-methyl-7-(2-phenylglycyl)amino-3-cephem-4-carboxylic acid (1.13 g), mp 168.5° to 171° C.

EXAMPLE 40

A solution of 2-methyl-7-[3-(tert.-butoxycarbonylamino)-3-(2-thienyl)propionamido]-3-cephem-4-carboxylic acid (310 mg) in formic acid (1.5 ml) was stirred for 4 hours at room temperature. After the reaction was completed, the solvent was distilled off from the reaction mixture, and the residue was pulverized by treating with ethyl acetate. Thus obtained yellow powder was suspended in a mixture of acetonitrile (10 ml) and water (3 ml), and the suspension was stirred for 1 hour. The precipitate was collected by filtration, and dried to give 2-methyl-7-[3-amino-3-(2-thienyl)propionamido]-3-cephem-4-carboxylic acid (180 mg), mp 218° to 221° C. (dec.).

EXAMPLE 41

A solution of 2-methyl-7-[N-(tert.-butoxycarbonyl)-2-(2-thienyl)glycyl]amino-3-cephem-4-carboxylic acid (2.34 g) in formic acid (10 ml) was stirred for 4 hours at room temperature. After the reaction was completed, the solvent was distilled off under reduced pressure from the reaction mixture, and the residue was pulverized by treating with ethyl acetate. The powder (1.79 g) was dissolved in water (40 ml) and the solution was stirred for 30 minutes, and then filtered. The filtrate was lyophilized to give 2-methyl-7-[2-(2-thienyl)glycyl]amino-3-cephem-4-carboxylic acid (1.5 g), mp 145° to 149° C.

EXAMPLE 42

A solution of 2-methyl-7-[D-N-(tert.-butoxycarbonyl)-2-(4-hydroxyphenyl)glycyl]-amino-3-cephem-4-carboxylic acid (2.0 g) in formic acid (40 ml) was stirred for 5 hours at room temperature. After the reaction was completed, the reaction mixture was concentrated under reduced pressure, and the residue was dissolved in a mixture of water and ethyl acetate. The aqueous layer was separated and lyophilized to give powdery 2-methyl-7-[D-2-(4-hydroxyphenyl)glycyl]amino-3-cephem-4-carboxylic acid (1.38 g).

Nuclear Magnetic Resonance Spectrum (D$_2$O+DCl, $\pi$)

| 8.60 | (3H, d, J=7.0Hz) |
| --- | --- |
| 6.1–6.7 | (1H, m) |
| 4.95 | (1H, d, J=4.5Hz) |
| 4.62 | (1H, s) |
| 4.11 | (1H, d, J=4.5Hz) |
| 3.40 | (1H, d, J=6Hz) |
| 2.93 | (2H, d, J=8.5Hz) |
| 2.48 | (2H, d, J=8.5Hz) |

EXAMPLE 43

A mixture of 2-methyl-7-[N-(Cl-cyclopropylethoxy)-carbonyl-2-(5,6-dihydro-2H-pyran-3-yl)glycyl]amino-3-cephem-4-carboxylic acid (3.0 g) and formic acid (20 ml) was stirred for 3 hours at room temperature. After the reaction was completed, formic acid was removed from the reaction mixture under reduced pressure at room temperature. The residue was pulverized with acetonitrile and the powder was collected by filtration. The powder was in turn washed with acetonitrile and water, and dried to give 2-methyl-7-[2-(5,6-dihydro-2H-pyran-3-yl)glycyl]amino-3-cephem-4-carboxylic acid (2.20 g), mp 125° to 128° C. (dec.).

EXAMPLE 44

A solution of 2-methyl-7-[N-tert.-butoxycarbonyl)-2-(3-methanesulfonamidophenyl)glycyl]amino-3-cephem-4-carboxylic acid (2.5 g) in formic acid (45 ml) was stirred for 4 hours at 8° to 15° C. After the reaction was completed, formic acid was removed from the reaction mixture under reduced pressure at 30° C. The residue was pulverized by adding ethyl acetate, and the powder was collected by filtration and then dissolved in water (70 ml). Ethyl acetate was added to the solution, followed by shaking the mixture, and the aqueous layer was separated. The aqueous layer was treated with charcoal and then lyophilized. Methanol (15 ml) and water (3 ml) were added to the residue and the mixture was stirred for 30 minutes at room temperature, filtered and dried to give powdery 2-methyl-7-[2-(3-methanesulfonamidophenyl)glycyl]amino-3-cephem-4-carboxylic acid (1.2 g), mp 192° to 193° C. (dec.).

EXAMPLE 45

A solution of 2-methyl-7-[N-(tert.-butoxycarbonyl)-2-(4-tert.-butoxycarbonylmethyoxyphenyl)glycyl]amino-3-cephem-4-carboxylic acid (3.0 g) in formic acid (50 ml) was stirred for 3 hours at 45° C. After the reaction was completed, formic acid was removed from the reaction mixture under reduced pressure, followed by adding acetonitrile (20 ml) to the residue, and the residue was pulverized by adding water (2 ml) under stirring. The powder was collected by filtration, washed with acetonitrile and dried to give powdery 2-methyl-7-[2-(4-carboxymethoxyphenyl)glycyl]amino-3-cephem-4-carboxylic acid (1.81 g).

Nuclear Magnetic Resonance Spectrum ($D_2O$ + DCl, $\pi$)

| | |
|---|---|
| 8.51, 8.60 | (3H, 2d, J=7.5Hz) |
| 6.3 | (1H, m) |
| 5.20 | (2H, s) |
| 4.95 | (1H, d, J=4.5Hz) |
| 4.69 | (1H, s) |
| 4.15, 4.32 | (1H, 2d, J=4.5Hz) |
| 3.20, 3.32 | (1H, 2s) |
| 2.90 | (2H, d, J=9Hz) |
| 2.46 | (2H, d, J=9Hz) |

EXAMPLE 46

A solution of 2-methyl-7-[N-(tert.-butoxycarbonyl)-2-(4-methylthiophenyl)glycyl]amino-3-cephem-4-carboxylic acid (3.0 g) in formic acid (100 ml) was stirred for 1 hour under anhydrous condition at room temperature. After the reaction was completed, the solvent was removed from the reaction mixture under reduced pressure, and the residue was dissolved in a mixture of water and ethyl acetate, after which the aqueous layer was separated. The aqueous layer was washed with ethyl acetate, and the organic solvent was completely removed under reduced pressure. The insoluble material was collected by filtration and lyophilized to give white powder of 2-methyl-7-[2-(4-methylthiophenyl)glycyl]amino-3-cephem-4-carboxylic acid (1.2 g), mp 165° to 175° C.

EXAMPLE 47

A solution of 2-methyl-7-[N-(tert.-butoxycarbonyl)-2-(4-methoxyphenyl)glycyl]amino-3-cephem-4-carboxylic acid (3.80 g) in formic acid (20 ml) was stirred for 4.5 hours at room temperature. After the reaction was completed, formic acid was removed from the reaction mixture below 35° C. under reduced pressure, and the residue was pulverized by adding acetonitrile, after which the powder was collected by filtration to give 2.9 g of the powder. The powder (2.6 g) was suspended in acetonitrile (50 ml). Water (1.5 ml) was added to the suspension, after which the mixture was stirred for 1 hour at room temperature. The precipitate was collected by filtration and dried to give 2-methyl-7-[2-(4-methoxyphenyl)glycyl]amino-3-cephem-4-carboxylic acid (2.15 g), mp 165° to 168° C. (dec.).

EXAMPLE 48

A mixture of 2-methyl-7-[N-(tert.-butoxycarbonyl)-2-(1,4-cyclohexadienyl)glycyl]amino-3-cephem-4-carboxylic acid (317 mg) and formic acid (3.17 ml) was stirred for 4 hours at room temperature. After the reaction was completed, formic acid was removed under reduced pressure from the reaction mixture and the residue was pulverized by adding ether. The powder was collected by filtration and dissolved in 95% acetonitrile aqueous solution (27 ml), and then the solution was stirred for an hour. Precipitates were collected by filtration and dried to give white crystals of 2-methyl-7-[2-(1,4-cyclohexadienyl)glycyl]amino-3-cephem-4-carboxylic acid (200 mg), mp 168° C. (dec.).

EXAMPLE 49

A solution of 2-methyl-7-[N-(tert.-butoxycarbonyl)-2-(4-methylsulfinylphenyl)glycyl]amino-3-cephem-4-carboxylic acid (2.9 g) in formic acid (7.5 ml) was stirred for 1 hour at room temperature under anhydrous condition. After the reaction was completed, the solvent was removed under reduced pressure from the reaction mixture, and the residue was dissolved in a small amount of water, after which acetonitrile was added to the solution, and the precipitated crystals were collected by filtration. The crystals were dissolved in water and the solution was lyophilized to give powdery 2-methyl-7-[2-(4-methylsulfinylphenyl)glycyl]amino-3-cephem-4-carboxylic acid (1.5 g), mp 178° to 180° C. (dec.).

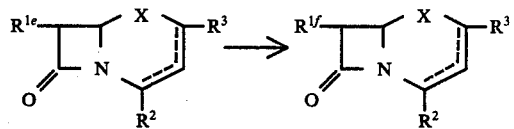

EXAMPLE 50

A 1% solution of phenolphthalein in 95% ethanol (1 drop) was added to a solution of 2-methyl-7-(D-2-phenyl-2-formyloxyacetamido)-3-cephem-4-carboxylic acid (0.43 g) in a mixture of water (5 ml) and methanol (7 ml). After each disappearance of red colour of phenolphthalein, 1N sodium hydroxide aqueous solution was dropwise added under ice-cooling to the solution. This operation was done to the time of disappearance of 2-methyl-7-(D-2-phenyl-2-formyloxyacetamido)-3-cephem-4-carboxylic acid in the reaction mixture, and the solution was adjusted to $pH^3$ with 10% hydrochloric acid. Methanol was removed from the reaction mixture under reduced pressure, and the precipitated gummy material was extracted four times with ethyl acetate (10 ml). The extract was combined, and the combined solution was dried over magnesium sulfate, after which the solvent was removed under reduced pressure. The residue was treated with isopropyl ether to give powder of 2-methyl-7-(D-2-phenyl-2-hydroxyacetamido)-3-cephem-4-carboxylic acid (0.29 g), mp 172° to 173° C. (dec.).

The following compound was obtained by using a similar manner. 2-Methyl-7-[2-(2-thienyl)-2-hydroxyacetamido]-3-cephem-4-carboxylic acid, mp 91° to 96° C. (dec.).

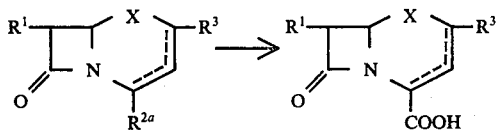

EXAMPLE 51

Zinc powder (3.0 g) was added under stirring at 5° C. to a solution of 2,2,2-trichloroethyl 2-methyl-7-[N-(1-cyclopropylethyoxy)carbonylphenylglycyl]amino-3-cephem-4-carboxylate (2.95 g) in a mixture of anhydrous dimethylformamido (12.5 ml) and acetic acid (3.75 ml), and the mixture was stirred for 1.5 hours. After the reaction, zinc powder was filtered off and washed with dimethylformamide (2 ml). The filtrate and the washings were combined, and the combined solution was extracted by pouring into a mixture of ethyl acetate (50 ml), ice-water (50 ml) and 10% hydrochloric acid (3 ml). The aqueous layer was further extracted with ethyl acetate (20 ml). The extract was combined, and then washed three times with water (20 ml) and once with a saturated sodium chloride aqueous solution and then dried over magnesium sulfate. After drying, the solvent was distilled off and the obtained residue was washed with ether and dried to give colorless crystals of 2-methyl-7-[N-(1-cyclopropylethoxy)-carbonylphenylglycyl]amino-3-cephem-4-carboxylic acid (2.01 g), mp 168° to 169° C.

EXAMPLE 52

Zinc powder (2.4 g) was added under ice-cooling and stirring to a solution of 2,2,2-trichloroethyl 2-methyl-7-[2-(1H-tetrazol-1-yl)acetamido]-3-cephem-4-carboxylate (2.0 g) in a mixture of anhydrous dimethylformamide (10 ml) and acetic acid (3 ml), and the mixture was stirred for 1.5 hours at the same temperature. After the reaction, zinc powder was filtered off, and the filtrate was extracted by pouring into a mixture of ethyl acetate (50 ml), ice-water and 10% hydrochloric acid (5 ml). The aqueous layer was further extracted with ethyl acetate (10 ml) and the ethyl acetate extract was combined, washed twice with water and dried over magnesium sulfate. After the solvent was distilled off, the residue was crystallized by adding a small amount of ether to give colorless crystals of 2-methyl-7-[2-(1H-tetrazol-1-yl)acetamido]-3-cephem-4-carboxylic acid (0.97 g), mp 202° to 203° C. (dec.).

EXAMPLE 53

Acetic acid (3 ml) and zinc powder (2.4 g) were added under stirring and ice-cooling to a solution of 2,2,2-trichloroethyl 2-methyl-7-[2-(2-thienyl)acetamido]-3-cephem-4-carboxylate (1.8 g) in anhydrous dimethyl-formamide (10 ml), and the mixture was stirred for 1 hour at the same temperature. After the reaction, zinc powder was filtered off, and the filtrate was extracted by pouring into a mixture of 5% hydrochloric acid (50 ml) and ethyl acetate (40 ml). The ethyl acetate layer was washed with water and dried. After the solvent was distilled off, the residue was dissolved in ether and allowed to stand, after which the precipitating crystals were collected by filtration and dried to give 2-methyl-7-[2-(2-thienyl)acetamido]-3-cephem-4-carboxylic acid (1.2 g), mp 175° C. (dec.).

EXAMPLE 54

Acetic acid (3 ml) and zinc powder (2.4 g) were added under stirring and ice-cooling to a solution of 2,2,2-trichloroethyl 2-methyl-7-benzyloxycarboxamido-3-cephem-4-carboxylate (1.9 g) in anhydrous dimethylformamide (10 ml), and the mixture was stirred for 1 hour at the same temperature. After the reaction, zinc powder was filtered off, and the filtrate was poured into a mixture of 5% hydrochloric acid (50 ml) and ethyl acetate (40 ml), and extracted. The extract was washed with water and then dried. After the solvent was distilled off, the residue was crystallized by adding ether to give colorless crystals of 2-methyl-7-benzyloxycarboxamido-3-cephem-4-carboxylic acid (1.13 g), mp 167° to 169° C. (dec.).

EXAMPLE 55

Acetic acid (4.5 ml) and zinc powder (3.6 g) were added under stirring and ice-cooling to a solution of 2,2,2-trichloroethyl 2-methyl-7-(2-phenylthioacetamido)-3-cephem-4-carboxylate (2.79 g) in anhydrous dimethylformamide (15 ml), and the mixture was stirred for 2 hours at the same temperature. After the reaction, zinc powder was filtered off, and the filtrate was poured into a mixture of 5% hydrochloric acid (75 ml) and ethyl acetate (50 ml), and extracted. The extract was washed with water and dried. After the solvent was distilled off, the residue was crystalized by adding ether to give colorless crystals of 2-methyl-7-(2-phenylthioacetamido)-3-cephem-4-carboxylic acid (2.0 g), mp 168° to 171° C. (dec.).

EXAMPLE 56

Acetic acid (4.1 ml) and zinc powder (3.4 g) were added under stirring and ice-cooling to a solution of 2,2,2-trichloroethyl 2-methyl-7-[2-(3-chlorophenyl)acetamido]-3-cephem-4-carboxylate (2.6 g) in anhydrous dimethylformamide (30 ml), and the mixture was stirred for 1.5 hours at the same temperature. After the reaction, zinc powder was filtered off, and the filtrate was poured into a mixture of 5% hydrochloric acid (150 ml) and ethyl acetate (75 ml), and then extracted. The extract was washed with water and dried. After the solvent was distilled off, the residue was crystallized by adding acetonitrile. The crystals were collected by filtration, washed with ether and dried to give colorless crystals of 2-methyl-7-[2-(3-chlorophenyl)acetamido]-3-cephem-4-carboxylic acid (1.4 g), mp 173° to 174° C. (dec.).

EXAMPLE 57

Zinc powder (0.6 g) was added under cooling at 0° to 5° C. to a solution of 2,2,2-trichloroethyl 2-methyl-7-[3-(N-tert.-butoxycarbonylamino)-3-(2-thienylpropionamido]-3-cephem-4-carboxylate (0.54 g) in a mixture of anhydrous dimethylformamide (3 ml) and acetic acid (1 ml), and the mixture was stirred for 2 hours. After the reaction, zinc powder was filtered off, and the filtrate was poured into a mixture of ethyl acetate (50 ml) and 5% hydrochloric acid (30 ml), and then extracted. The extract was washed with a saturated sodium chloride aqueous solution, dried over magnesium sulfate, after which the solvent was distilled off to give 2-methyl-7-[3-(N-tert.-butoxycarbonylamino)-3-(2-thienyl)propionamido]-3-cephem-4-carboxylic acid (0.365 g), mp 167° to 170° C. (dec.).

EXAMPLE 58

Acetic acid (4 ml) and zinc powder (3 g) were added under stirring and ice-cooling to a solution of 2,2,2-trichloroethyl 2-methyl-7-(2-cyanoacetamido)-3-cephem-4-carboxylate (3.2 g) in anhydrous dimethylformamide (15 ml), and the mixture was stirred for 1 hour at the same temperature. After the reaction, ethyl acetate (100 ml) was added to the reaction mixture. The insoluble material was filtered off, and the filtrate was washed with 5% hydrochloric acid saturated with sodium chloride, and then extracted with a saturated sodium bicarbonate aqueous solution. The extract was acidified with 10% hydrochloric acid and extracted with ethyl acetate. The extract was washed with a saturated sodium chloride aqueous solution and dried over magnesium sulfate. After the solvent was distilled off, the crystalline residue was recrystallized from a mixture of ethyl acetate and benzene to give 2-methyl-7-(2-cyanoacetamido)-3-cephem-4-carboxylic acid (2.3 g), mp 162° to 166° C.

EXAMPLE 59

Acetic acid (8 ml) and zinc powder (6 g) were added under stirring and ice-cooling to a solution of 2,2,2-trichloroethyl 2-methyl-7-(3-phenylureido)-3-cephem-4-carboxylate (4.1 g) in anhydrous dimethylformamide (30 ml), and the mixture was stirred for 1 hour under ice-cooling and then 3.5 hours at room temperature. After the reaction, 10% hydrochloric acid and ethyl acetate were added to the reaction mixture. The insoluble material was filtered off and the ethyl acetate layer was separated, and then extracted with a sodium bicarbonate aqueous solution. The extract was acidified with 10% hydrochloric acid and extracted with ethyl acetate, after which the extract was dried over magnesium sulfate. After the solvent was distilled off, the residue was crystallized by adding ether to give 2-methyl-7-(3-phenylureido)-3-cephem-4-carboxylic acid (1.0 g), mp 148° to 151° C.

EXAMPLE 60

Acetic acid (8 ml) and zinc powder (6 g) were added under stirring and ice-cooling to a solution of 2,2,2-trichloroethyl 2-methyl-7-[2-(1,3,4-thiadiazol-2-ylthio)acetamido]-3-cephem-4-carboxylate (4.65 g) in anhydrous dimethylformamide (30 ml), and the mixture was stirred for 1 hour at the same temperature. After the reaction, ethyl acetate (150 ml) was added to the reaction mixture. The insoluble material was filtered off, and the filtrate was washed with 5% hydrochloric acid saturated with sodium chloride, and then extracted with a sodium bicarbonate aqueous solution. The extract was acidified with 10% hydrochloric acid and extracted with ethyl acetate, after which the ethyl acetate layer was washed with a saturated sodium chloride aqueous solution and dried over magnesium sulfate. After the solvent was distilled off, the residue was recrystallized from a mixture of ethyl acetate and benzene to give 2-methyl-7-[2-(1,3,4-thiadiazol-2-ylthio)acetamido]-3-cephem-4-carboxylic acid (1.5 g), mp 197° to 199° C.

EXAMPLE 61

Acetic acid (1.6 ml) and zinc powder (1.2 g) were added under stirring and ice-cooling to a solution of 2,2,2-trichloroethyl 2-methyl-7-[N-tert.-butoxycarbonyl-2-(2-thienyl)glycyl]amino-3-cephem-4-carboxylate (1.52 g) in anhydrous dimethylformamide (10 ml), and the mixture was stirred for 1 hour at the same temperature. After the reaction, zinc powder was filtered off, and the filtrate was poured into an ice-cooled mixture of 2 to 3% hydrochloric acid and ethyl acetate and then extracted. The extract was washed with water, extracted with a sodium bicarbonate aqueous solution, after which the aqueous layer was acidified by adding 5% sulfuric acid and ethyl acetate and extracted with ethyl acetate. The extract was washed with water, dried over magnesium sulfate, followed by distilling off the solvent under reduced pressure. The residue was pulverized by adding isopropyl ether, collected by filtration and dried to give amorphous 2-methyl-7-[N-tert.-butoxycarbonyl-2-(2-thienyl)glycyl]amino-3-cephem-4-carboxylic acid (0.7 g).

Infrared Absorption Spectrum (Nujol) 3300, 1789, 1725, 1710, 1690, 1678 cm$^{-1}$

EXAMPLE 62

Acetic acid (8 ml) and zinc powder (6 g) were added under ice-cooling to a solution of 2,2,2-trichloroethyl 2-methyl-7-[2-(5-methyl-1,3,4-thiadiazol-2-yloxy)acetamido]-3-cephem-4-carboxylate (6.60 g) in anhydrous dimethylformamide (40 ml), and the mixture was stirred for 1.5 hours. After the reaction, zinc powder was filtered and washed with dimethylformamide. The filtrate and the washings were combined, and the combined solution was poured into an ice-cooled mixture of ethyl acetate and 2 to 3% hydrochloric acid, and then extracted. The extract was extracted with a sodium bicarbonate aqueous solution and the aqueous solution was acidified with hydrochloric acid, and then extracted with ethyl acetate. The aqueous layer was saturated with sodium chloride, and then extracted, four times with ethylacetate (80 ml), after which the both ethyl acetate extract was combined. After the combined extracted was dried over magnesium sulfate, the solvent was distilled off under reduced pressure. The residue was crystallized by adding ether to give dimethylformamide adduct of 2-methyl-7-[2-(5-methyl-1,3,4-thiadiazol-2-yloxy)acetamido]-3-cephem-4-carboxylic acid (2.0 g), mp 113° to 116° C.

EXAMPLE 63

Zinc powder (0.6 g) was added under stirring and ice-cooling to a solution of 2,2,2-trichloroethyl 2-methyl-7-[3-(2-chlorophenyl)-5-methylisoxazol-4-yl]carboxamido-3-cephem-4-carboxylate (0.6 g) in a mixture of anhydrous dimethylformamide (5 ml) and acetic acid (0.8 ml), and the mixture was stirred for 40 minutes at the same temperature. After the reaction, zinc powder was filtered and washed with dimethylformamide. The filtrate and the washings were combined, and the combined solution was poured into an ice-cooled mixture of ethyl acetate and 2 to 3% hydrochloric acid, and then extracted with ethyl acetate. The extract was extracted with a sodium bicarbonate aqueous solution, and the aqueous layer was acidified with 10% sulfuric acid and then extracted with ethyl acetate, after which the extract was washed with water and dried over magnesium sulfate. After the solvent was distilled off under reduced pressure, the oily substance was crystallized by adding ether, and the crystals were collected by filtration, and then washed with ether to give 2-methyl-7-[3-(2-chlorophenyl)-5-methylisoxazol-4-yl]carboxamido-3-cephem-4-carboxylic acid (0.2 g), mp 202° to 203° C.

EXAMPLE 64

2,2,2-Trichloroethyl 2-methyl-7-(2-methylthioacetamido)-3-cephem-4-carboxylate (0.48 g), glacial acetic acid (0.48 ml) and zinc powder (0.48 g) were added to anhydrous dimethylformamide (5 ml), and the mixture was stirred for 1 hour under ice-cooling. After the reaction, zinc powder was filtered off. The filtrate was poured into a mixture of 3% hydrochloric acid (10 ml) and ethyl acetate (10 ml), and the ethyl acetate layer was separated. The aqueous layer was further extracted three times with ethyl acetate (10 ml). The ethyl acetate layer was combined. The combined extract was washed with a saturated sodium chloride aqueous solution and dried over magnesium sulfate, after which the solvent was distilled off under reduced pressure. The obtained residue was crystallized by adding ether and the crystals were collected by filtration and washed with ether to give 2-methyl-7-(2-methylthioacetamido)-3-cephem-4-carboxylic acid (0.29 g), mp 181° to 183° C. (dec.).

EXAMPLE 65

Zinc powder (5.55 g) was added to a solution of 2,2,2-trichloroethyl 2-methyl-7-(2-allylthioacetamido)-3-cephem-4-carboxylate (5.55 g) in anhydrous dimethylformamide (55.5 ml) and then acetic acid (5.5 ml) was dropwise added to the solution, after which the mixture was stirred for 1 hour. After the reaction, zinc powder was filtered off and washed with ethyl acetate. The filtrate and the washings were combined, after which the solution was poured into a mixture of 5% hydrochloric acid (250 ml) and ethyl acetate (100 ml), and then extracted. The aqueous layer was further extracted twice with ethyl acetate. The ethyl acetate layer was combined, and the combined ethyl acetate layer was washed with a saturated sodium chloride aqueous solution, and then dried over magnesium sulfate. After the solution was concentrated under reduced pressure till the volume of the solution becomes about 40 ml. Crystals precipitated were collected by filtration and washed with isopropyl ether and dried to give colorless crystals of 2-methyl-7-(2-allylthioacetamido)-3-cephem-4-carboxylic acid (3.69 g), mp 121° to 123° C. Moreover the filtrate was concentrated and the obtained crystals were washed with isopropyl ether and then dried to give 2-methyl-7-(2-allylthioacetamido)-3-cephem-4-carboxylic acid (0.75 g).

EXAMPLE 66

2,2,2-Trichloroethyl 2-methyl-7-(2-formyloxy-2-phenylacetamido)-3-cephem-4-carboxylate (1.58 g), zinc powder (1.5 g) and glacial acetic acid (1.5 ml) were added to anhydrous dimethylformamide (15 ml), and the mixture was stirred for 1 hour under ice-cooling. After the reaction, zinc powder was filtered off, and the filtrate was poured into a mixture of 5% hydrochloric acid (30 ml) and ethyl acetate (30 ml) and then extracted. The aqueous layer was further extracted twice with ethyl acetate (30 ml). The ethyl acetate layer was combined, and the combined solution was washed with 5% hydrochloric acid and water, and then dried over magnesium sulfate. After the solvent was distilled off under reduced pressure, the residue was pulverized by adding isopropyl ether, followed by filtration, and dried to give amorphous 2-methyl-7-(2-formyloxy-2-phenylacetamido)-3-cephem-4-carboxylic acid (1.0 g).

Infrared Absorption Spectrum (Nujol) 3280, 1787, 1720, 1678 cm$^{-1}$

EXAMPLE 67

Zinc powder (1.2 g) was added under ice-cooling to a solution of 2,2,2-trichloroethyl 2-methyl-7-(1-cyclopropylethoxy)carboxamido-3-cephem-4-carboxylate (0.92 g) in a mixture of dimethylformamide (5 ml) and acetic acid (1.5 ml), and the mixture was stirred for 1.5 hours at the same temperature. After the reaction, zinc powder was filtered off and washed with dimethylformamide (2 ml). The dimethylformamide layer was poured into a mixture of ethyl acetate (30 ml), water (30 ml) and 10% hydrochloric acid (2 ml) and extracted. The dimethylformamide layer was further extracted with ethyl acetate (10 ml). The ethyl acetate extract was combined, washed in turn with water, a saturated sodium chloride aqueous solution, dried over magnesium sulfate, after which the solvent was distilled off. The residue was pulverized using a small amount of ether to give 2-methyl-7-(1-cyclopropylethoxy)carboxamido-3-cephem-4-carboxylic acid (0.45 g), mp 158.5° to 160° C. (dec.).

EXAMPLE 68

Acetic acid (1 ml) and zinc powder (2.0 g) were added under ice-cooling to a solution of 2,2,2-trichloroethyl 2-methyl-7-amino-3-cephem-4-carboxylate hydrochloride (1.53 g) in dimethylformamide (10 ml) and the mixture was stirred for 1 hour at −5° to 0° C., after which the reaction mixture was filtered. The filtered zinc powder was washed with dimethylformamide and the filtrate and the washings were combined, after which a few mls. of water was added to the solution. The precipitated crystals were collected by filtration and dissolved in a small amount of a sodium bicarbonate aqueous solution and then the insoluble material was filtered off. The filtrate was adjusted to pH$^4$ with 10% hydrochloric acid and the precipitated crystals were collected by filtration, washed with water and acetone and dried to give 2-methyl-7-amino-3-cephem-4-carboxylic acid (0.38 g), mp 222° C. (dec.).

EXAMPLE 69

Zinc powder (2.4 g) was added under ice-cooling to a solution of 2,2,2-trichloroethyl 2-methyl-7-(2-phenylacetamido)-3-cephem-4-carboxylate (1.85 g) in a mixture of dimethylformamide (10 ml) and acetic acid (3 ml), and the mixture was stirred for 2 hours, after which the reaction mixture was filtered. The filtrate was poured into a mixture of ethyl acetate (50 ml), ice-water (50 ml) and 10% hydrochloric acid (2 ml), and then the ethyl acetate layer was separated. The aqueous layer was further extracted with ethyl acetate (10 ml). The ethyl acetate layer was combined, and the combined solution was in turn washed with water and a saturated sodium chloride aqueous solution, dried over magnesium sulfate, after which the solvent was distilled off. The residue was crystallized by adding a small quantity of acetonitrile and the precipitated crystals were collected by filtration and dried to give colorless crystals of 2-methyl-7-(2-phenylacetamido)-3-cephem-4-carboxylic acid (1.2 g), mp 109° C. (dec.).

EXAMPLE 70

Zinc powder (0.9 g) was added under ice-cooling to a solution of 2,2,2-trichloroethyl 2-methyl-7-(2-phenylacetamido)-3-cephem-4-carboxylate (0.69 g), mp 120° to 130° C., in a mixture of dimethylformamide (5 ml) and acetic acid (1 ml), and the mixture was stirred for 1.5 hours, followed by filtration of the reaction mixture, after which the filtered zinc was washed with a small amount of dimethylformamide. The filtrate and the washings were combined and the combined solution was poured into a mixture of ethyl acetate (30 ml), water (30 ml) and 10% hydrochloric acid (2 ml), after which the ethyl acetate layer was separated. The aqueous layer was further extracted with ethyl acetate (10 ml). The ethyl acetate layer was combined, and the combined solution was in turn washed with water, a saturated sodium chloride aqueous solution, dried over magnesium sulfate, after which the solvent was distilled off. The residue was crystallized by adding a small quantity of acetonitrile, and the precipitated crystals were collected by filtration and dried to give 2-methyl-7-(2-phenylacetamido)-3-cephem-4-carboxylic acid (0.34 g), mp 121° C., which is an isomer at 2 position of 2-methyl-7-(2-phenylacetamido)-3-cephem-4-carboxylic acid, mp 109° C. (dec.), which was obtained in Example 19.

EXAMPLE 71

Zinc powder (1.8 g) was added under ice-cooling to a solution of 2,2,2-trichloroethyl 2-methyl-7-(2-phenylacetamido)-2-cephem-4-carboxylate (1.0 g) in a mixture of dimethylformamide (7.5 ml) and acetic acid (2.5 ml), and the mixture was stirred for 1.5 hours, followed by filtration of the reaction mixture, and the filtered zinc was washed with dimethylformamide (2 ml). The filtrate and the washings were combined and the combined solution was poured into a mixture of ethyl acetate (30 ml), ice-water (30 ml) and 10% hydrochloric acid (2 ml), after which the ethyl acetate layer was separated. The aqueous layer was further extracted with ethyl acetate (10 ml). The ethyl acetate layer was combined, and the combined solution was in turn washed with water, a saturated sodium chloride aqueous solution, dried over magnesium sulfate, after which the solvent was distilled off. The residue was crystallized by adding a small quantity of ether, after which the precipitated crystals were collected by filtration and dried to give colorless crystals of 2-methyl-7-(2-phenylacetamido)-2-cephem-4-carboxylic acid (0.45 g), mp 204° C.

The following compounds were obtained by using the similar procedures as those of the above Examples.

(1) 2-Methyl-7-(phenylglycyl)amino-3-cephem-4-carboxylic acid, mp 168.5° to 171° C.
(2) 2-Methyl-7-[3-amino-3-(2-thienyl)propionamido]-3-cephem-4-carboxylic acid, mp 218° to 221° C. (dec.).
(3) 2-Methyl-7-[(2-thienyl)glycyl]-amino-3-cephem-4-carboxylic acid, mp 145° to 149° C. (dec.).
(4) 2-Methyl-7-(2-hydroxy-2-phenylacetamido)-3-cephem-4-carboxylic acid, mp 172° to 173° C.
(5) 2-Methyl-7-[N-tert.-butoxycarbonyl-2-(2,5-dihydrophenyl)glycyl]amino-3-cephem-4-carboxylic acid, mp 126° to 131° C. (dec.).
(6) 2-Methyl-7-[N-tert.-butoxycarbonyl-2-(4-hydroxyphenyl)-D-glycyl]amino-3-cephem-4-carboxylic acid, powder.
(7) 2-Methyl-7-[N-tert.-butoxycarbonyl-2-(4-methylthiophenyl)glycyl]amino-3-cephem-4-carboxylic acid, mp 110° to 120° C.
(8) 2-Methyl-7-[N-tert.-butoxycarbonyl-2-(4-methoxyphenyl)glycyl]amino-3-cephem-4-carboxylic acid, mp 81° to 86° C. (dec.).
(9) 2-Methyl-7-(2-sulfo-2-phenyl-acetamido)-3-cephem-4-carboxylic acid, 115° C. (vesication), 200° to 220° C. (dec.).
(10) 2-Methyl-7-(2-azido-2-phenylacetamido)-3-cephem-4-carboxylic acid, mp 65° to 68° C.
(11) 2-Methyl-7-[2-(3-pyridyl)acetamido]-3-cephem-4-carboxylic acid, mp 147° to 149° C. (dec.).
(12) 2-Methyl-7-[2-hydroxy-2-(2-thienyl)acetamido]-3-cephem-4-carboxylic acid, mp 91° to 96° C. (dec.).
(13) 2-Methyl-7-[N-(1,3,4-thiadiazol-2-yl)thiomethylcarbonyl-2-phenylglycyl]amino-3-cephem-4-carboxylic acid, mp 143° to 145° C. (dec.).
(14) 2-Methyl-7-[N-tert.-butoxycarbonyl-2-(4-tert.-butoxycarbonylmethoxyphenyl)glycyl]-amino-3-cephem-4-carboxylic acid, powder.
(15) 2-Methyl-7-[N-(1-cyclopropylethoxy)carbonyl-2-(5,6-dihydro-2H-pyran-3-yl)glycyl]amino-3-cephem-4-carboxylic acid, mp 195° to 197° C.
(16) 2-Methyl-7-[2-(1,2,5-thiadiazol-3-yl)acetamido]-3-cephem-4-carboxylic acid, mp 188° to 190° C. (dec.).
(17) 2-Methyl-7-[N-tert.-butoxycarbonyl-2-(3-methanesulfonamidophenyl)glycyl]amino-3-cephem-4-carboxylic acid, oil.
(18) 2-Methyl-7-[N-tert.-butoxycarbonyl-2-(4-methylsulfinylphenyl)glycyl]amino-3-cephem-4-carboxylic acid, mp 110° to 120° C.
(19) 2-Methyl-7-[2-(5-indanyl)oxycarbonyl-2-phenylacetamido]-3-cephem-4-carboxylic acid, 90° to 95° C. (softening), 150° to 160° C. (dec.).
(20) 2-Methyl-7-(2-isonicotinoyloxy-2-phenylacetamido)3-cephem-4-carboxylic acid, mp 217° to 219° C.
(21) 2-Methyl-7-[D-2-(4-hydroxyphenyl)glycyl]amino-3-cephem-4-carboxylic acid, powder.
(22) 2-Methyl-7-[2-(5,6-dihydro-2H-pyran-3-yl)glycyl]amino-3-cephem-4-carboxylic acid, mp 125° to 128° C. (dec.).
(23) 2-Methyl-7-[2-(3-methanesulfonamidophenyl)glycyl]amino-3-cephem-4-carboxylic acid, mp 192° to 193° C. (dec.).
(24) 2-Methyl-7-[2-(4-carboxymethoxyphenyl)glycyl]amino-3-cephem-4-carboxylic acid, powder.
(25) 2-Methyl-7-[2-(4-methylthiophenyl)glycyl]amino-3-cephem-4-carboxylic acid, mp 165° to 175° C.
(26) 2-Methyl-7-[2-(4-methoxyphenyl)glycyl]amino-3-cephem-4-carboxylic acid, mp 165° to 168° C.
(27) 2-Methyl-7-[2-(2,5-dihydrophenyl)glycyl]amino-3-cephem-4-carboxylic acid, mp 168° C. (dec.).
(28) 2-Methyl-7-[2-(4-methylsulfinylphenyl)glycyl]amino-3-cephem-4-carboxylic acid, powder.
(29) 2-Methyl-7-[2-(5,6-dihydro-2H-pyran-3-yl)acetamido]-3-cephem-4-carboxylic acid, mp 172.5° to 173.5° C. (dec.).
(30) 2-Methyl-7-(4-methoxyphenyl)glyoxylamido-3-cephem-4-carboxylic acid, mp 188° to 189° C. (dec.).
(31) 2-Methyl-7-(N-tert.-butoxycarbonylphenyl-D-glycyl)amino-3-cephem-4-carboxylic acid, mp 125° to 127° C. (dec.).
(32) 2-Methyl-7-[N-[2-(2-nitrophenoxy)acetyl]phenylglycyl]-amino-3-cephem-4-carboxylic acid, mp 135° to 137° C. (dec.).
(33) 2-Methyl-7-[2-(2-aminothiazol-4-yl)acetamido]-3-cephem-4-carboxylic acid, which can be represented as 2-methyl-7-[2-(2-imino-2,3-dihydrothiazol-4-yl)acetamido]-3-cephem-4-carboxylic acid, mp 250° to 255° C. (dec.).

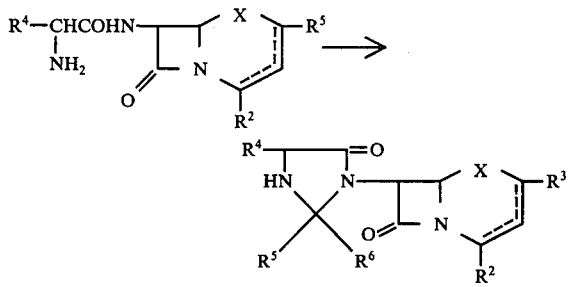

EXAMPLE 72

A suspension of 2-methyl-7-(2-phenylglycyl)amino-3-cephem-4-carboxylic acid (1.0 g) in water (10 ml) was adjusted to pH 8.8 by adding dropwise 10% sodium hydroxide. To the suspension was added acetone (10 ml), and the mixture was stirred for 24 hours in an ice bath. Acetone was removed under reduced pressure, and then the aqueous layer was adjusted to about pH 3.5 with 10% hydrochloric acid, and then extracted three times with ethyl acetate (20 ml). The residue obtained by distilling off ethyl acetate was dissolved in a small amount of acetone, and then a small quantity of insoluble material was filtrated off. A great quantity of ether was added to the filtrate, and then the precipitate was collected by filtration to give 2-methyl-7-(2,2-dimethyl-4-phenyl-5-oxoimidazolidin-1-yl)-3-cephem-4-carboxylic acid (0.30 g), mp 160° to 162° C. (dec.).

EXAMPLE 73

The data in Table 1 below present a comparison between the 2-($C_1$–$C_6$ alkyl)-cephem compounds of the present invention and known cephem compounds structurally analogous to the present compounds, differing only by alkyl substitution in the 3-position. The in vitro tests of antimicrobial activity of the compared compounds were determined by the two-fold agar plate dilution method described as follows:

One loopful of an overnight culture of each test strain in Trypticase-soy broth ($10^8$ viable cells per ml) was streaked on heart agar (HI sugar) containing graded concentration of antibiotics, and the minimum inhibitory concentration (MIC) was expressed in terms of mcg/ml after incubation at 37° C. for 20 hours. The results are given in Table I.

The specific cephem compounds compared in Table I are as follows:

(1) 2-Methyl-7-[N-[2-(1,3,4-thiadiazol-2-ylthio)acetyl]-phenylglycyl]amino-3-cephem-4-carboxylic acid (hereinafter referred to as Applicants' compound (1))

(2) 2-Methyl-7-[2-hydroxy-2-(2-thienyl)acetamido]-3-cephem-4-carboxylic acid (hereinafter referred to as Applicants' compound (2))
   3-Methyl-7-[2-hydroxy-2-(2-thienyl)acetamido]-3-cephem-4-carboxylic acid (sodium salt) (hereinafter referred to as cited compound (2))

(3) 2-Methyl-7-[2-(5-indanyloxy)carbonyl-2-phenylacetamido]-3-cephem-4-carboxylic acid (hereinafter referred to as Applicants' compound (3))

(4) 2-Methyl-7-(2-isonicotinoyloxy-2-phenylacetamido)-3-cephem-4-carboxylic acid (hereinafter referred to as Applicants' compound (4))
   3-Methyl-7-(2-isonicotinoyloxy-2-phenylacetamido-3-cephem-4-carboxylic acid (hereinafter referred to as cited compound (4))

(5) 2-Methyl-7-[2-(2-thienyl)acetamido]-3-cephem-4-carboxylic acid (hereinafter referred to as Applicants' compound (5))
   3-Methyl-7-[2-(2-thienyl)acetamido]-3-cephem-4-carboxylic acid (hereinafter referred to as cited compound (5))

(6) 2-Methyl-7-[2-(3-chlorophenyl)acetamido]-3-cephem-4-carboxylic acid (hereafter referred to as Applicants' compound (6))

(7) 2-Methyl-7-(2-hydroxy-2-phenylacetamido)-3-cephem-4-carboxylic acid (hereafter referred to as Applicants' compound (7))
   3-Methyl-7-(2-hydroxy-2-phenylacetamido)-3-cephem-4-carboxylic acid (hereafter referred to as cited compound (7))

(8) 2-Methyl-7-(2-phenylacetamido)-3-cephem-4-carboxylic acid (hereafter referred to as Applicants' compound (8))
   3-Methyl-7-(2-phenylacetamido)-3-cephem-4-carboxylic acid (hereafter referred to as cited compound (8))

(9) 2-Methyl-7-(2-phenylthioacetamido)-3-cephem-4-carboxylic acid (hereafter referred to as Applicants' compound (9))
   3-Methyl-7-(2-phenylthioacetamido)-3-cephem-4-carboxylic acid (hereafter referred to as cited compound (9))

(10) 2-Methyl-7-(2-azido-2-phenylacetamido)-3-cephem-4-carboxylic acid (hereafter referred to as Applicants' compound (10))

(11) 2-Methyl-7-[2-(1,3,4-thiadiazol-2-ylthio)acetamido]-3-cephem-4-carboxylic acid (hereafter referred to as Applicants' compound (11))
   3-Methyl-7-[2-(1,3,4-thiadiazol-2-ylthio)acetamido]-3-cephem-4-carboxylic acid (hereafter referred to as cited compound (11))

(12) 2-Methyl-7-[2-(1,2,5-thiadiazol-3-yl)acetamido]-3-cephem-4-carboxylic acid (hereafter referred to as Applicants' compound (12)) p1 3-Methyl-7-[2-(1,2,5-thiadiazol-3-yl)acetamido]-3-cephem-4-carboxylic acid (hereafter referred to as cited compound (12))

(13) 2-Methyl-7-(2-cyanoacetamido)-3-cephem-4-carboxylic acid (hereafter referred to as Applicants' compound (13))
   3-Methyl-7-(2-cyanoacetamido)-3-cephem-4-carboxylic acid (hereafter referred to as cited compound (13))

(14) 2-Methyl-7-[2-(allylthio)acetamido]-3-cephem-4-carboxylic acid (hereafter referred to as Applicants' compound (14))
   3-Methyl-7-[2-(allylthio)acetamido]-3-cephem-4-carboxylic acid (hereafter referred to as cited compound (14))

(15) 2-Methyl-7-[2-(3-pyridyl)acetamido]-3-cephem-4-carboxylic acid (hereafter referred to as Applicants' compound (15))
   3-Methyl-7-[2-(3-pyridyl)acetamido]-3-cephem-4-carboxylic acid (hereafter referred to as cited compound (15))

(16) 2-Methyl-7-[2-amino-2-(4-methylthiophenyl)acetamido]-3-cephem-4-carboxylic acid (hereafter referred to as Applicants' compound (16))

(17) 2-Methyl-7-[2-(2-aminothiazol-4-yl)acetamido]-3-cephem-4-carboxylic acid, which can be represented as 2-methyl-7-[2-(2-imino-2,3-dihydrothiazol-4- yl)acetamido]-3-cephem-4-carboxylic acid (hereafter referred to as Applicants' compound (17))

(18) 2-Methyl-7-(2-phenylglycyl)-amino-3-cephem-4-carboxylic acid (hereinafter referred to as Applicants' compound (18))

3-Methyl-7-(2-phenylglycyl)amino-3-cephem-4-carboxylic acid (hereinafter referred to as cited compound (18))

Note: This compound is marketed by Eli Lilly and Company in the U.S.A. under the tradename "Keflex". The Eli Lilly Company is the assignee of U.S. Pat. No. 3,275,626 and U.S. Pat. No. 3,814,754.

Table 1
(Method for estimation of antimicrobial activity in vitro)

| Applicants' compound | (1) | (2) | (3) | (4) | (5) | (6) | (7) | (8) | (9) | (10) |
|---|---|---|---|---|---|---|---|---|---|---|
| *Staphylococcus aureus* | | | | | | | | | | |
| 209 P JC-1 | 1.56 | 0.78 | 1.56 | 0.39 | 0.78 | 0.1 | 0.78 | 0.78 | 0.2 | 1.56 |
| 206 | 3.13 | 0.78 | 0.39 | 0.78 | 1.56 | 0.39 | 1.56 | 1.56 | 0.39 | 1.56 |
| 213 | 3.13 | 3.13 | 0.39 | 1.56 | 1.56 | 0.39 | 1.56 | 1.56 | 0.39 | 1.56 |
| 226 | 1.56 | 3.13 | 0.20 | 0.78 | 1.56 | 0.20 | 1.56 | 1.56 | 0.39 | 1.56 |
| 277 | 12.5 | 3.13 | 0.78 | 6.25 | 1.56 | 0.78 | 6.25 | 3.13 | 1.56 | 12.5 |
| 278 | 3.13 | 3.13 | 0.39 | 1.56 | 1.56 | 0.39 | 1.56 | 1.56 | 0.78 | 1.56 |
| *Bacillus subtilis* ATCC-6633 | 3.13 | 0.78 | 6.25 | 0.78 | 0.39 | 0.2 | 0.39 | 0.2 | 0.2 | 0.39 |
| cited compound | | (2) | | (4) | (5) | | (7) | (8) | (9) | |
| *Staphylococcus aureus* | | | | | | | | | | |
| 209 P JC-1 | | 6.25 | | 1.56 | 3.13 | | 3.13 | 1.56 | 0.39 | |
| 206 | | 6.25 | | 12.5 | 3.13 | | 12.5 | 6.25 | 0.39 | |
| 213 | 25 | | 12.5 | 12.5 | | 25 | 6.25 | 0.78 | | |
| 226 | | 12.5 | | 12.5 | 12.5 | | 12.5 | 3.13 | 1.56 | |
| 277 | | 12.5 | | 12.5 | 12.5 | | 12.5 | 1.56 | 0.39 | |
| 278 | | 12.5 | | 12.5 | 6.25 | | 12.5 | 3.13 | 0.39 | |
| *Bacillus subtilis* ATCC-6633 | | 1.56 | | 0.78 | 0.78 | | 1.56 | 0.78 | 0.39 | |
| Applicants' compound | (11) | (12) | (13) | (14) | (15) | (16) | (17) | (18) | | |
| *Staphylococcus aureus* | | | | | | | | | | |
| 209 P JC-1 | 1.56 | 3.13 | 3.13 | 1.56 | 3.13 | 3.13 | 1.56 | 6.25 | | |
| 206 | 3.13 | 3.13 | 6.25 | 3.13 | 6.25 | 6.25 | 3.13 | 12.5 | | |
| 213 | 6.25 | 6.25 | 12.5 | 6.25 | 6.25 | 25 | 1.56 | 50 | | |
| 226 | 3.13 | 3.13 | 6.25 | 3.13 | 6.25 | 6.25 | 1.56 | 25 | | |
| 277 | 3.13 | 6.25 | 3.13 | 1.56 | 25 | 25 | 1.56 | 12.5 | | |
| 278 | 6.25 | 6.25 | 6.25 | 3.13 | 6.25 | 12.5 | 1.56 | 25 | | |
| *Bacillus subtilis* ATCC-6633 | 0.78 | 1.56 | 3.13 | 1.56 | 0.78 | 6.25 | 3.13 | 1.56 | | |
| cited compound | (11) | (12) | (13) | (14) | (15) | | | (18) Keflex | | |
| *Staphylococcus aureus* | | | | | | | | | | |
| 209 P JC-1 | 3.13 | 12.5 | 6.25 | 6.25 | 6.25 | | | 3.13 | | |
| 206 | 3.13 | 12.5 | 6.25 | 6.25 | 12.5 | | | 6.25 | | |
| 213 | 6.25 | 25 | 12.5 | 12.5 | 25 | | | 12.5 | | |
| 226 | 6.25 | 25 | 12.5 | 6.25 | 12.5 | | | 12.5 | | |
| 277 | 6.25 | 25 | 12.5 | 6.25 | 6.25 | | | 12.5 | | |
| 278 | 3.13 | 25 | 12.5 | 6.25 | 12.5 | | | 3.13 | | |
| *Bacillus subtilis* ATCC-6633 | 1.56 | 3.13 | 3.13 | 3.13 | 1.56 | | | 1.56 | | |

The results of Table I clearly show the superior antimicrobial activity of the present 2-(lower alkyl)-cephem compounds [(1)–(17)] compared to the conventional 3-alkylcephem compounds of the prior art.

The following test describes the method of estimating the protecting effects of Applicants' compound (18) versus cited compound (18), "Keflex", against experimental infections in mice.

Test Method:

Male ICR strain mice aged 4 weeks, each weighing 20–23 g were used in groups of 8 mice. The organisms precultured overnight at 37° C. on HI-agar were suspended in 5% mucin solution to obtain cell concentrations of $8.5 \times 10^2$ cells/mouse. Mice were inoculated intraperitoneally with 0.5 ml of the suspension. Each of the test antibiotics was given subcutaneously to the mice one hour after challenge. The $ED_{50}$ values were found by the probit method from the number of surviving mice after one week of observation. The results are given in Table 2.

Table 2
(Protecting effect against experimental infections in mice)

| | | MIC (µg/ml) | | $ED_{50}$ (mg/mouse) | |
|---|---|---|---|---|---|
| | Inoculum size | Applicants' compound (18) | The cited compound (18) Keflex | Applicants' compound (18) | The cited compound (18) Keflex |
| *E. coli* 327 | $10^8$ | 100 | 100 | | |
| | $10^6$ | 50 | 12.5 | 0.25 | 1.06 |
| | $10^4$ | 12.5 | 6.25 | | |

The results in Table 2 show that antimicrobial activities in vivo of the applicants' compound (18) are superior to those of the cited compound (18) which is marketed under the tradename "Keflex" although antimicrobial activities in vitro of applicants' compound (18) are inferior to those of cited compound (18).

What we claim is:
1. A compound of the general formula:

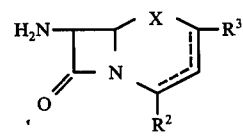

wherein $R^2$ is carboxy or a protected carboxy selected from the group consisting of tri($C_1$-$C_6$) alkylsilyl ester, ($C_1$-$C_{16}$) alkyl ester, ($C_2$-$C_6$) alkenyl ester, ($C_2$-$C_6$) alkynyl ester, ($C_3$-$C_8$) cycloalkyl ester, ($C_1$-$C_6$) alkoxy ($C_1$-$C_6$) alkyl ester, ($C_1$-$C_6$) alkylthio ($C_1$-$C_6$) alkyl ester, di($C_1$-$C_6$) alkylamino ester, ($C_1$-$C_6$) alkylideneamino ester, ($C_1$-$C_6$) alkylsulfenyl ($C_1$-$C_6$) alkyl ester, ($C_1$-$C_6$) alkanoyloxy ($C_1$-$C_6$) alkyl ester, phenyl ester, xylyl ester, naphthyl ester, indanyl ester, dihydroanthryl ester, phenyl ($C_1$-$C_6$) alkyl ester, phenoxy ($C_1$-$C_6$) alkyl ester, phenylthio ($C_1$-$C_6$) alkyl ester, phenylsulfenyl ($C_1$-$C_6$) alkyl ester, benzoyl ($C_1$-$C_6$) alkyl ester, phthalimido ester, pyridyl ester, piperidino ester, 2-pyridon-1-yl ester, tetrahydropyranyl ester, quinolyl ester, pyrazolyl ester, heterocyclic ($C_1$-$C_6$) alkyl ester wherein said heterocyclic moiety is selected from the group consisting of pyridyl, piperidino, 2-pyridon-1-yl, tetrahydropyranyl, quinolyl and pyrazolyl, the above recited ester having from 1 to 10 of the substituents selected from the group consisting of ($C_1$-$C_6$) alkyl, ($C_1$-$C_6$) alkoxy, ($C_1$-$C_6$) alkylthio, ($C_1$-$C_6$) alkylsulfinyl, ($C_1$-$C_6$) alkanesulfonyl, phenylazo, halogen, cyano and nitro; N-($C_1$-$C_6$) alkyl acid amide, N,N-di($C_1$-$C_6$) alkyl acid amide and acid amide formed with pyrazole, imidazole or 4-($C_1$-$C_6$) alkylimidazole; $R^3$ is ($C_1$-$C_6$) alkyl, and X is —S— or

or a pharmaceutically acceptable salt thereof.

2. The compound of claim 1, wherein
$R^2$ is carboxy, ($C_1$-$C_6$) alkoxycarbonyl, trihalo ($C_1$-$C_6$) alkoxycarbonyl; or ($C_1$-$C_6$) alkanoyloxy ($C_1$-$C_6$) alkoxycarbonyl;
$R^3$ is ($C_1$-$C_6$) alkyl and
X is —S—.

3. The compound of claim 2, wherein
$R^2$ is carboxy or 2,2,2-trichloroethoxycarbonyl,
$R^3$ is methyl and
X is —S—.

4. The compound of claim 2, which is 2-methyl-7-amino-3-cephem-4-carboxylic acid.

5. The compound of claim 2, which is 2,2,2-trichloroethyl 2-methyl-7-amino-3-cephem-4-carboxylate.

* * * * *